US010869874B2

(12) United States Patent
Singer et al.

(10) Patent No.: US 10,869,874 B2
(45) **Date of Patent: *Dec. 22, 2020**

(54) METHODS AND COMPOSITIONS FOR TOPICAL DELIVERY OF PROSTAGLANDINS TO SUBCUTANEOUS FAT

(71) Applicant: Topokine Therapeutics, Inc., Parsippany, NJ (US)

(72) Inventors: Michael S. Singer, Newton Center, MA (US); Murat V. Kalayoglu, Silver Spring, MD (US)

(73) Assignee: Topokine Therapeutics, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,253

(22) Filed: Nov. 17, 2017

(65) Prior Publication Data

US 2018/0169111 A1 Jun. 21, 2018

Related U.S. Application Data

(63) Continuation of application No. 14/889,093, filed as application No. PCT/US2014/038067 on May 15, 2014, now Pat. No. 9,820,993.

(60) Provisional application No. 61/823,659, filed on May 15, 2013.

(51) Int. Cl.

| | |
|---|---|
| ***A61K 31/5575*** | (2006.01) |
| ***A61K 8/34*** | (2006.01) |
| ***A61Q 19/06*** | (2006.01) |
| ***A61K 9/00*** | (2006.01) |
| ***A61K 47/10*** | (2017.01) |
| ***A61K 47/12*** | (2006.01) |
| ***A61K 8/69*** | (2006.01) |
| ***A61K 8/36*** | (2006.01) |
| ***A61K 8/37*** | (2006.01) |

(52) U.S. Cl.

CPC ............ *A61K 31/5575* (2013.01); *A61K 8/34* (2013.01); *A61K 8/345* (2013.01); *A61K 8/361* (2013.01); *A61K 8/37* (2013.01); *A61K 8/69* (2013.01); *A61K 9/0014* (2013.01); *A61K 47/10* (2013.01); *A61K 47/12* (2013.01); *A61Q 19/06* (2013.01)

(58) Field of Classification Search

None

See application file for complete search history.

(56) References Cited

U.S. PATENT DOCUMENTS

| | | | |
|---|---|---|---|
| 4,599,353 | A | 7/1986 | Bito |
| 5,296,504 | A | 3/1994 | Stjernschantz et al. |
| 5,422,368 | A | 6/1995 | Stjernschantz et al. |
| 5,520,639 | A | 5/1996 | Peterson et al. |
| 5,631,287 | A | 5/1997 | Schneider |
| 5,688,819 | A | 11/1997 | Woodward et al. |
| 5,849,792 | A | 12/1998 | Schneider |
| 5,886,035 | A | 3/1999 | Shirasawa et al. |
| 5,889,052 | A | 3/1999 | Klimko et al. |
| 5,972,991 | A | 10/1999 | Burk |
| 5,990,139 | A | 11/1999 | Yano et al. |
| 6,232,344 | B1 | 5/2001 | Feng et al. |
| 6,235,781 | B1 | 5/2001 | Weiner et al. |
| 6,262,105 | B1 | 7/2001 | Johnstone |
| 6,403,649 | B1 | 6/2002 | Woodward et al. |
| 6,646,001 | B2 | 11/2003 | Hellberg et al. |
| 6,730,707 | B2 | 5/2004 | Pintor et al. |
| 6,864,282 | B2 | 3/2005 | Ling et al. |
| 6,911,474 | B2 | 6/2005 | Piomelli et al. |
| 6,933,289 | B2 | 8/2005 | Lyons et al. |
| 7,070,768 | B2 | 7/2006 | Krauss |
| 7,125,542 | B2 | 10/2006 | Miller et al. |
| 7,351,404 | B2 | 4/2008 | Woodward et al. |
| 7,622,130 | B2 | 11/2009 | Kolodney et al. |
| 7,666,912 | B2 | 2/2010 | Grosskreutz et al. |
| 8,273,362 | B2 | 9/2012 | Philips et al. |
| 8,318,678 | B2 | 11/2012 | Marini |
| 8,367,606 | B2 | 2/2013 | Tennenbaum et al. |
| 8,426,471 | B1 | 4/2013 | Kalayoglu et al. |
| 8,569,376 | B2 | 10/2013 | Kalayoglu et al. |
| 8,722,097 | B2 | 5/2014 | Chang et al. |
| 8,778,981 | B2 | 7/2014 | Kalayoglu et al. |

(Continued)

FOREIGN PATENT DOCUMENTS

| | | | |
|---|---|---|---|
| CN | 101151034 | A | 3/2008 |
| CN | 101427993 | A | 5/2009 |

(Continued)

OTHER PUBLICATIONS

PCT/US2007/005424, Aug. 10, 2007, Invitation to Pay Additional Fees.

PCT/US2007/005424, Nov. 26, 2007, International Search Report and Written Opinion.

PCT/US2007/005424, Sep. 23, 2008, International Preliminary Report on Patentability.

12859422.3, Jul. 10, 2015, Extended European Search Report.

(Continued)

*Primary Examiner* — Kamal A Saeed

(74) *Attorney, Agent, or Firm* — Wolf, Greenfield & Sacks, P.C.

(57) ABSTRACT

Described herein are compositions comprising a prostaglandin FP receptor agonist (PFPRA) compound and a fatty acid, e.g., oleic acid, that, when topically applied to the skin, locally delivers a therapeutically effective amount of the PFPRA compound or active metabolite thereof to subcutaneous fat under the skin. The therapeutic effect is, for example, reduction of the subcutaneous fat under the skin. Further provided are methods of reducing body fat in a subject comprising topically administering the composition to the subject. The present invention also provides kits comprising the composition and instructions for use.

22 Claims, 2 Drawing Sheets

(56) References Cited

U.S. PATENT DOCUMENTS

| | | | |
|---|---|---|---|
| 8,829,050 | B2 | 9/2014 | Grosskreutz et al. |
| 8,841,345 | B2 | 9/2014 | Lu et al. |
| 8,877,807 | B2 | 11/2014 | Grosskreutz et al. |
| 9,040,584 | B2 | 5/2015 | Singer et al. |
| 9,089,579 | B2 | 7/2015 | Kalayoglu |
| 9,144,574 | B2 | 9/2015 | Grosskreutz |
| 9,180,130 | B2 | 11/2015 | Kalayoglu et al. |
| 9,421,215 | B2 | 8/2016 | Grosskreutz et al. |
| 9,504,695 | B2 | 11/2016 | Kalayoglu |
| 9,795,614 | B2 | 10/2017 | Grosskreutz et al. |
| 9,820,993 | B2 | 11/2017 | Singer et al. |
| 10,188,661 | B2 | 1/2019 | Singer et al. |
| 10,285,995 | B2 | 5/2019 | Grosskreutz et al. |
| 10,335,418 | B2 | 7/2019 | Kalayoglu |
| 10,556,012 | B2 | 2/2020 | Singer et al. |
| 2002/0172693 | A1 | 11/2002 | DeLong et al. |
| 2003/0181354 | A1 | 9/2003 | Abdulrazik |
| 2004/0023954 | A1 | 2/2004 | Ling et al. |
| 2004/0082660 | A1 | 4/2004 | Ueno |
| 2004/0115234 | A1 | 6/2004 | Gewirtz |
| 2004/0180200 | A1 | 9/2004 | Bertamini |
| 2004/0241245 | A1 | 12/2004 | Lu et al. |
| 2005/0058614 | A1 | 3/2005 | Krauss |
| 2005/0117830 | A1 | 6/2005 | Hartog et al. |
| 2005/0261373 | A1 | 11/2005 | Ueno |
| 2005/0261641 | A1 | 11/2005 | Warchol et al. |
| 2006/0034786 | A1 | 2/2006 | Michelet et al. |
| 2006/0246145 | A1 | 11/2006 | Chang et al. |
| 2007/0224246 | A1 | 9/2007 | Hughes et al. |
| 2007/0248658 | A1 | 10/2007 | Zurdo Schroeder et al. |
| 2008/0015257 | A1 | 1/2008 | Grosskreutz et al. |
| 2008/0107738 | A1 | 5/2008 | Philips et al. |
| 2008/0233053 | A1 | 9/2008 | Gross et al. |
| 2009/0042909 | A1 | 2/2009 | Karnik |
| 2010/0104654 | A1 | 4/2010 | Robinson et al. |
| 2010/0105771 | A1 | 4/2010 | deLong et al. |
| 2010/0234466 | A1 | 9/2010 | Grosskreutz et al. |
| 2010/0291226 | A1 | 11/2010 | Mazzone et al. |
| 2011/0124736 | A1 | 5/2011 | Trogden et al. |
| 2012/0046256 | A1 | 2/2012 | Dobak |
| 2012/0129789 | A1 | 5/2012 | Yoelin |
| 2012/0251613 | A1 | 10/2012 | Jain |
| 2012/0295972 | A1 | 11/2012 | Woodward et al. |
| 2013/0023536 | A1 | 1/2013 | Graham et al. |
| 2013/0178525 | A1 | 7/2013 | Kalayoglu et al. |
| 2014/0045933 | A1 | 2/2014 | Kalayoglu |
| 2014/0163098 | A1 | 6/2014 | Grosskreutz et al. |
| 2014/0350104 | A1 | 11/2014 | Kalayoglu et al. |
| 2015/0025150 | A1 | 1/2015 | Kalayoglu |
| 2015/0025151 | A1 | 1/2015 | Grosskreutz et al. |
| 2015/0105462 | A1 | 4/2015 | Singer et al. |
| 2015/0164765 | A1 | 6/2015 | Yoelin |
| 2015/0231251 | A1 | 8/2015 | Singer et al. |
| 2015/0359801 | A1 | 12/2015 | Grosskreutz et al. |
| 2016/0051562 | A1 | 2/2016 | Kalayoglu et al. |
| 2016/0067263 | A1 | 3/2016 | Singer et al. |
| 2016/0354386 | A1 | 12/2016 | Grosskreutz et al. |
| 2017/0136032 | A1 | 5/2017 | Kalayoglu |
| 2017/0202852 | A1 | 7/2017 | Singer et al. |
| 2018/0104255 | A1 | 4/2018 | Grosskreutz et al. |
| 2018/0200372 | A1 | 7/2018 | Singer et al. |
| 2018/0353517 | A1 | 12/2018 | Kalayoglu et al. |
| 2020/0069699 | A1 | 3/2020 | Grosskreutz et al. |

FOREIGN PATENT DOCUMENTS

| | | | |
|---|---|---|---|
| EA | 006556 | B1 | 2/2006 |
| EP | 302147 | A1 | 2/1989 |
| EP | 1 864 666 | A1 | 12/2007 |
| EP | 2 228 058 | A1 | 9/2010 |
| EP | 3 124 015 | A1 | 2/2017 |
| KR | 20140043562 | A | 10/2014 |
| RU | 2157689 | C2 | 10/2000 |
| RU | 2325912 | C1 | 6/2008 |
| RU | 2009140073 | A | 5/2011 |
| WO | WO 1997/13537 | A1 | 4/1997 |
| WO | WO 2003/066008 | A1 | 8/2003 |
| WO | WO 2005/034889 | A2 | 4/2005 |
| WO | WO 2005/034890 | A2 | 4/2005 |
| WO | WO 2006/048750 | A2 | 5/2006 |
| WO | WO 2007/111806 | A2 | 10/2007 |
| WO | WO 2010/039535 | A1 | 4/2010 |
| WO | WO 2010/100217 | A1 | 9/2010 |
| WO | WO 2011/057129 | A2 | 5/2011 |
| WO | WO 2012/068515 | A2 | 5/2012 |
| WO | WO 2012/099942 | A2 | 7/2012 |
| WO | WO 2012/131734 | A1 | 10/2012 |

OTHER PUBLICATIONS

PCT/US2012/070581, May 30, 2013, International Search Report and Written Opinion.

PCT/US2012/070581, Jul. 3, 2014, International Preliminary Report Report on Patentability.

PCT/US2014/038067, Sep. 29, 2014, International Search Report and Written Opinion.

PCT/US2014/038067, Nov. 26, 2015, International Preliminary Report on Patentability.

16177742.0, Dec. 6, 2016, Extended European Search Report.

PCT/US2014/037512, Aug. 21, 2014, Invitation to Pay Additional Fees.

PCT/US2014/037512, Dec. 4, 2014, International Search Report and Written Opinion.

PCT/US2014/037512, Nov. 19, 2015, International Preliminary Report on Patentability.

12736090.7, Jul. 8, 2014, Extended European Search Report.

15180363.2, Dec. 21, 2015, Extended European Search Report.

PCT/US2012/021692, Feb. 21, 2013, Invitation to Pay Additional Fees.

PCT/US2012/021692, May 3, 2013, International Search Report and Written Opinion.

PCT/US2012/021692, Aug. 1, 2013, International Preliminary Report on Patentability.

PCT/US2015/037323, Aug. 12, 2015, International Search Report and Written Opinion.

PCT/US2015/037323, Jun. 17, 2016, Second Written Opinion.

[No Author Listed], Allergan Announces FDA Approval of Lumigan as First-Line Treatment for Elevated Eye Pressure in Open-Angle Glaucoma; Indication Expands Approved Uses of Lumigan in the Management of Glaucoma. Business Wire. Jun. 23, 2006. Available at http://findarticles.com/p/articles/mi_m0EIN/is_2006June_23/ai_n26905641. Last visited Aug. 7, 2008. 2 pages.

[No Author Listed], Allergan Announces FDA Approval of Lumigan® as First-Line Treatment for Elevated Eye Pressure in Open-Angle Glaucoma; Indication Expands Approved Uses of Lumigan(R) in the Management of Glaucoma. Allergan Press Release. Jun. 23, 2006. Avaiable at http://agn360.client.shareholder.com/releasedetail.cfm?ReleaseID=201809. Last visited Sep. 9, 2008. 3 pages.

[No Author Listed], Chapter 42. Pharmacology of Eicosanoids. In: Principles of Pharmacology. The Pathophysiologic Basis of Drug Therapy. 3rd ed. Golan et al., eds. 2012: 743.

[No Author Listed], Excerpts from BodybuildingForYou—Bodybuilding Forums: Anabolic Steroids/Prohormones, and Testosterone Enhancers <http://www.bodybuildingforyou.com/forums/anabolic-steroids- prohormones-testosterone-enhancers/>/ Anabolic Steroids & Anabolic Chemistry & Testosterone Enhancers <http://www.bodybuildingforyou.com/forums/anabolic-steroids- anabolic-chemistry-testosterone-enhancers/>/ Anabolic Steroid, HGH, IGF, Insulin and Ancillary Profiles, pgf2a parts 3-5, post Nos. 35-37 by RRAdam on Jul. 12, 2005, http://www.bodybuildingforyou.com/forums/anabolic-steroids-anabolic-chemistry-testosterone-enhancers/22591-anabolic-steroid-hgh-igf-insulin-ancillary profiles-2.html (14 pages).

[No Author Listed], Excerpts from Wanna Be Big Bodybuilding and Weightlifting Forums: Community Central <http://www.wannabebigforums.com/archive/index.php/f-20.html>/ General Chat <http://www.wannabebigforums.com/archive/index.php/f-12.html>/

(56) References Cited

OTHER PUBLICATIONS

The Myostatin Gene, posted at 4:22pm, Feb. 5, 2001, by Cackerot69, http://www.wannabebiciforums.com/archive/index.php/t-359.html (4 pages).
[No Author Listed], FDA CDER Approval Letter (3 pages) and Toxicology Study #5 from CDER Pharmacology Review (cover page and pp. 43-44 of 107 included) for Lumigan (Bimatoprost Ophthalmic Solution), NDA Application No. 21-275 (FDA Approval Date: Mar. 16, 2001), available at http://www.fda.gov/cder/foi/nda/2001/21275_Lumigan.htm (last visited May 23, 2008).
[No Author Listed], FDA CDER Toxicology Study #18 from CDER Pharmacology Review (cover page and pp. 67-69 of 107 included) for Lumigan (Bimatoprost Ophthalmic Solution), NDA Application No. 21-275 (FDA Approval Date: Mar. 16, 2001), available at http://www.fda.gov/cdergoi/nda/2001/21275_Lumigan.htm (last visited Dec. 22, 2008).
[No Author Listed], KEGG Database, Eicosanoids—Reference Pathway, available at http://www.genome.jp/kegg/pathway/map/map07034.html (last visited Jun. 10, 2008, 1 page).
[No Author Listed], Kegg Drug: D02724, [online] retrieved on Nov. 30, 2007, (2007), retrieved from http://www.genome.ad.jp/dbget-bin/www_bget?drug+D02724 and http://www.genome.ad.jp/dbget-bin/www_bget?pathway+map07035, printed p. 1 and printed pp. 1-3, respectively.
[No Author Listed], Latisse and Safety. Last accessed on Jul. 24, 2012 at http://www.latisseonline.com/latisse-safety/ 2 pages.
[No Author Listed], Material Safety Data Sheet for Lutalyse® Sterile Solution, dated Jun. 23, 1997, available at httplApfww.lutelysacomipahirnageslmsde...usiLutalvse.pdf (last visited Dec. 22, 2006).
[No Author Listed], Ointments: Preparation and Evaluation of Drug Release. The Pharmaceutics and Compounding Laboratory. Mar. 4, 2013. http://pharmlabs.unc.edu/ointments/bases.htm. 2 pages.
[No Author Listed], Original New Animal Drug Application for ProstaMateTm (dinoprost tromethamine injection) Sterile Solution (ANADA No. 200-253). Dated Feb. 12, 1999. Available at http://www.fdagovlohrmsidockets/98fr1200253fi.pdf. Last visited Dec. 22, 2008.
[No Author Listed], Pfizer Inc., Citizen Petition to the Food and Drug Administration: Revoke Approval of Allergan's Supplemental NDA #21-257/S-013 for Lumigan (Bimatoprost Ophthalmic Solution 0.03%) and Deny Alcon's Supplemental NDA for Travatan (Travoprost Ophthalmic Solution 0.004%), submitted on Nov. 1, 2006, available at http://www.fda.gov/ohrms/dockets/dockets/06p0450/06p-0450-cp00001-toc.htm.
[No Author Listed], Prescribing Information for Saflutan® 15 micrograms/ml eye drops, solution, single-dose container (tafluprost), dated Aug. 2009.
[No Author Listed], Product Label of Lumigan (bimatoprost ophthalmic solution) 0.03%, label for Jun. 22, 2006 approval of new or modified indication, available at http://www.fda.gov/cder/foi/label/2006/021275s013lbl.pdf (last visited Sep. 9, 2008).
[No Author Listed], Product Label of Travatan® (travoprost ophthalmic solution) 0.004%, label for Feb. 13, 2003 approval of efficacy supplement with clinical data to support, available at http://www.fda.gov/cder/foUlabel/2003/021257s0061bl.pdf (last visited Sep. 9, 2008).
[No Author Listed], Product Label of Xalatan® (latanoprost ophthalmic solution), label for Dec. 20, 2002 approval of new or modified indication, available at http://www.fda.gov/cder/foi/label/2002/20597SE1-010_Xalatan_lbl.pdf (last visited Sep. 9, 2008).
[No Author Listed], Prostaglandin analogues. Entrepreneur.com. 2008. Available at http://www.entrepreneur.com/tradejournals/article/print/166777491.html. 2 pages.
[No Author Listed], Travatan™ (travoprost ophthalmic solution) 0.004% Sterile. NDA 21-257. Alcon Laboratories Inc. 2001. 7 pages.
Aihara et al., Incidence of deepening of the upper eyelid sulcus after switching from latanoprost to bimatoprost. Jpn J Ophthalmol. Nov. 2011;55(6):600-4. Epub Sep. 28, 2011.
Aydin et al., Recovery of orbital fat pad prolapsus and deepening of the lid sulcus from topical bimatoprost therapy: 2 case reports and review of the literature. Cutan Ocul Toxicol. Sep. 2010;29(3):212-6.
Berenson et al., Changes in weight, total fat, percent body fat, and central-to-peripheral fat ratio associated with injectable and oral contraceptive use. Am J Obstet Gynecol. Mar. 2009;200(3):329.e1-8.
Blank et al., Mechanism of percutaneous absorption. 3. The effect of temperature on the transport of non-electrolytes across the skin. J Invest Dermatol. Dec. 1967;49(6):582-9.
Casimir et al., Preadipocyte differentiation blocked by prostaglandin stimulation of prostanoid FP2 receptor in murine 3T3-L1 cells. Differentiation. Jul. 1996;60(4):203-10.
Casimir, Regulation of early preadipocyte differentiation: cAMP and prostaglandin F-2-alpha. ProQuest Dissertations and Theses; 1996; ProQuest Dissertations & Theses (PQDT). UMI No. 9634889. 162 pages.
Choi et al., In vitro study of antiadipogenic profile of latanoprost, travoprost, bimatoprost, and tafluprost in human orbital preadiopocytes. J Ocul Pharmacol Ther. Apr. 2012;28(2):146-52. Epub Nov. 22, 2011. E-pub version.
Database WPI, Week 201434. Thomson Scientific, London, GB; An 2014-G76718 XP002729483 & KR 2014 0043562. Apr. 10, 2014. 3 pages.
Dayan et al., Delivery System Design in Topically Applied Formulations: An Overview. In: Delivery System Handbook for Personal Care and Cosmetic Products. Rosen, ed. William Andrew. 2005:103-104.
Email from Dr. Louis Pasquale to Lisa Putukian sent at 10:16 am, May 20, 2008, and forwarded to Daniel Wilson at 10:22 am, May 20, 2008, and related e-mail thread (3 pages).
E-mail from Dr. Michael Singer to Randall Morin sent at 1:57 pm, Jun. 4, 2008, and attached letter (8 pages) and Exhibits 1-10 from Dr. Singer to Mr. Morin dated Jun. 4, 2004.
Extended European Search Report, dated Dec. 6, 2016, in connection with Application No. EP 16177742.0.
Extended European Search Report, dated Dec. 21, 2015, in connection with Application No. EP 15180363.2.
Extended European Search Report, dated Jul. 10, 2015, in connection with Application No. EP 12859422.3.
Extended European Search Report, dated Jul. 8, 2014, in connection with Application No. EP 12736090.7.
Filippopoulos et al., Periorbital changes associated with topical bimatoprost. Ophthal Plast Reconstr Surg. Jul.-Aug. 2008;24(4):302-7.
Fricke et al, The PGF(2alpha) receptor FP is lost in nevi and melanoma. Pigment Cell Melanoma Res. Feb. 2010;23(1):141-3. Epub Dec. 11, 2009.
Gregoire et al., Understanding adipocyte differentiation. Physiol Rev. Jul. 1998;78(3):783-809.
Grosskreutz et al., Periorbital Fat Loss and Eyelid Sulcus Deepening after Bimatoprost Therapy. Final Program and Abstract Book, pp. 49 and 53, distributed at The American Glaucoma Society 2006 Annual Meeting, Mar. 2-5, 2006.
Grosskreutz et al., Periorbital Fat Loss and Eyelid Sulcus Deepening after Bimatoprost Therapy. Poster presented at The American Glaucoma Society 2006 Annual Meeting, Charleston, South Carolina. Mar. 2-5, 2006. 1 page.
Grosskreutz, Abstract submitted on Nov. 1, 2005 to the American Glaucoma Society for the American Glaucoma Society 2006 Annual Meeting. 1 page.
Hata et al., Pharmacology and signaling of prostaglandin receptors: multiple roles in inflammation and immune modulation. Pharmacol Ther. Aug. 2004;103(2):147-66.
Hellberg et al., The hydrolysis of the prostaglandin analog prodrug bimatoprost to 17-phenyl-trinor PGF2alpha by human and rabbit ocular tissue. J Ocul Pharmacol Ther. Apr. 2003;19(2):97-103.
Holmstrom et al., Analytic review of bimatoprost, latanoprost and travoprost in primary open angle glaucoma. Curr Med Res Opin. Nov. 2005;21(11):1875-83.
Husain et al., Acute effects of PGF2alpha on MMP-2 secretion from human ciliary muscle cells: a PKC- and ERK-dependent process. Invest Ophthalmol Vis Sci. May 2005;46(5):1706-13.

(56) References Cited

OTHER PUBLICATIONS

Ichhpujani et al., Comparison of human ocular distribution of bimatoprost and latanoprost. J Ocul Pharmacol Ther. Apr. 2012;28(2):134-45. doi: 10.1089/jop.2011.0097. Epub Dec. 2, 2011.
Initial Information Disclosure Statement for U.S. Appl. No. 11/712,839, May 19, 2008 (4 pages).
Inoue et al., Deepening of the Upper Eyelid Sulcus Caused by 5 Types of Prostaglandin Analogs. J Glaucoma. Aug. 29, 2012. [Epub ahead of print] E-pub version. 6 pages.
International Preliminary Report on Patentability, dated Aug. 1, 2013, in connection with Application for PCT/US2012/021692.
International Preliminary Report on Patentability, dated Jul. 3, 2014, in connection with Application for PCT/US2012/070581.
International Preliminary Report on Patentability, dated Nov. 19, 2015, in connection with Application No. PCT/US2014/037512.
International Preliminary Report on Patentability, dated Nov. 26, 2015, in connection with Application No. PCT/US2014/038067.
International Preliminary Report on Patentability, dated Sep. 23, 2008, in connection with Application No. PCT/US2007/005424.
International Search Report and Written Opinion, dated Aug. 12, 2015, in connection with Application No. PCT/US2015/037323.
International Search Report and Written Opinion, dated Dec. 4, 2014, in connection with Application No. PCT/US2014/037512.
International Search Report and Written Opinion, dated May 3, 2013, in connection with Application for PCT/US2012/021692.
International Search Report and Written Opinion, dated May 30, 2013, in connection with Application No. PCT/US2012/070581.
International Search Report and Written Opinion, dated Nov. 26, 2007, in connection with Application No. PCT/US2007/005424.
International Search Report and Written Opinion, dated Sep. 29, 2014, in connection with Application No. PCT/US2014/038067.
Invitation to Pay Additional Fees, dated Aug. 10, 2007, in connection with PCT/U52007/005424.
Invitation to Pay Additional Fees, dated Aug. 21, 2014, in connection with Application No. PCT/US2014/037512.
Invitation to Pay Additional Fees, dated Feb. 21, 2013, in connection with PCT/US2012/021692.
Izumi et al., Short-term effects of topical tafluprost on retinal blood flow in cats. J Ocul Pharmacol Ther. Oct. 2008;24(5):521-6. doi: 10.1089/jop.2007.0065.
Jabbour et al., A positive feedback loop that regulates cyclooxygenase-2 expression and prostaglandin F2alpha synthesis via the F-series-prostanoid receptor and extracellular signal-regulated kinase 1/2 signaling pathway. Endocrinology. Nov. 2005;146(11):4657-64. Epub Aug. 4, 2005.
Kuenzli et al., Effect of topical PPARbeta/delta and PPARgamma agonists on plaque psoriasis. A pilot study. Dermatology. 2003;206(3):252-6.
Kumar et al., Lecithin organogels as a potential phospholipid-structured system for topical drug delivery: a review. AAPS PharmSciTech. Oct. 6, 2005;6(2):E298-310.
Lepak et al., Inhibition of adipose differentiation by 9 alpha, 11 beta-prostaglandin F2 alpha. Prostaglandins. Dec. 1993;46(6):511-7.
Lepak et al., Prostaglandin F2 alpha stimulates transforming growth factor-alpha expression in adipocyte precursors. Endocrinology. Aug. 1995;136(8):3222-9.
Lesser et al., Modification of subcutaneous adipose tissue by a methylxanthine formulation: a double-blind controlled study. Dermatol Surg. Jun. 1999;25(6):455-62.
Letter from Dr. Michael Singer to Lisa Putukian dated Sep. 22, 2008 (1 page—email correspondence attachment and MEEI Patent Policy and Procedures attachment omitted).
Letter from Dr. Michael Singer to Lisa Putukian dated Sep. 26, 2007 (3 pages and facsimile cover sheet).
Letter from Lisa Putukian to Dr. Michael Singer dated Sep. 22, 2008 (1 page.).
Letter from Lisa Putukian to Dr. Michael Singer dated Sep. 28, 2007 (2 pages), and attached Preliminary Amendment (3 pages).
Liu et al., Postaglandin F2alpha inhibits adipocyte differentiation via a G alpha q-calcium-calcineurin-dependent signaling pathway. J Cell Biochem. Jan. 1, 2007;100(1):161-73.
Löffler et al., Adipose tissue development: the role of precursor cells and adipogenic factors. Part II: The regulation of the adipogenic conversion by hormones and serum factors. Klin Wochenschr. Sep. 1, 1987;65(17):812-7.
Maxey et al., The hydrolysis of bimatoprost in corneal tissue generates a potent prostanoid FP receptor agonist. Surv Ophthalmol. Aug. 2002;47 Suppl 1:S34-40.
Miller et al., The mechanism of inhibition of 3T3-L1 preadipocyte differentiation by prostaglandin F2alpha. Endocrinology. Dec. 1996;137(12):5641-50.
Nakajima et al., New fluoroprostaglandin F(2alpha) derivatives with prostanoid FP-receptor agonistic activity as potent ocular-hypotensive agents. Biol Pharm Bull. Dec. 2003;26(12):1691-5.
Nakakura et al., Latanoprost therapy after sunken eyes caused by travoprost or bimatoprost. Optom Vis Sci. Sep. 2011;88(9):1140-4.
Ota et al., The IOP-lowering effects and mechanism of action of tafluprost in prostanoid receptor-deficient mice. Br J Ophthalmol. May 2007;91(5):673-6. Epub Nov. 23, 2006.
Pantoja et al., Glucocorticoid signaling defines a novel commitment state during adipogenesis in vitro. Mol Biol Cell. Oct. 2008;19(10):4032-41. Epub Jul. 23, 2008.
Park et al., Changes to upper eyelid orbital fat from use of topical bimatoprost, travoprost, and latanoprost. Jpn J Ophthalmol. Jan. 2011;55(1):22-7. Epub Feb. 18, 2011.
Park et al., In vitro skin penetration and pharmacodynamic evaluation of prostaglandin E1 ethyl ester, a vasoactive prodrug of prostaglandin E1, formulated into alcoholic hydrogels. Pharmazie. Nov. 2006;61(11):933-7.
Paula et al., Periorbital Fat Loss and Eyelid Sulcus Deepening after Bimatoprost Therapy. Manuscript submitted to Archives of Ophthalmology, Oct. 21, 2005 (10 pages).
Peplinski et al., Deepening of lid sulcus from topical bimatoprost therapy. Optom Vis Sci. Aug. 2004;81(8):574-7.
Porter et al., Abdominal subcutaneous adipose tissue: a protective fat depot? Diabetes Care. Jun. 2009;32(6):1068-75. doi: 10.2337/dc08-2280. Epub Feb. 24, 2009.
Reginato et al., Prostaglandins promote and block adipogenesis through opposing effects on peroxisome proliferator-activated receptor gamma. J Biol Chem. Jan. 23, 1998;273(4):1855-8.
Robin, An accurate comparison of bimatoprost's efficacy and adverse effects. Arch Ophthalmol. Jul. 2002;120(7):999-1000; author reply 1000.
Rundle, Drug That Lengthens Eyelashes Sets Off Flutter. Wall Street J. Nov. 19, 2007 (2 pages).
Sales et al., Expression, localization, and signaling of prostaglandin F2 alpha receptor in human endometrial adenocarcinoma: regulation of proliferation by activation of the epidermal growth factor receptor and mitogen-activated protein kinase signaling pathways. J Clin Endocrinol Metab. Feb. 2004;89(2):986-93.
Sales et al., F-prostanoid receptor regulation of fibroblast growth factor 2 signaling in endometrial adenocarcinoma cells. Endocrinology. Aug. 2007;148(8):3635-44. Epub May 3, 2007.
Schiwek et al., Glucocorticoid hormones contribute to the adipogenic activity of human serum. Endocrinology. Feb. 1987;120(2):469-74. Abstract only.
Second Written Opinion, dated Jun. 17, 2016, in connection with Application No. PCT/US2015/037323.
Selliah et al., AL-12182, a novel 11-oxa prostaglandin analog with topical ocular hypotensive activity in the monkey. Bioorg Med Chem Lett. Sep. 6, 2004;14(17):4525-8.
Serrero et al., Prostaglandin F2 alpha inhibits epidermal growth factor binding to cellular receptors on adipocyte precursors in primary culture. Biochem Biophys Res Commun, Jul. 26, 1995;212(3):1125-32.
Serrero et al., Prostaglandin F2 alpha inhibits the differentiation of adipocyte precursors in primary culture. Biochem Biophys Res Commun. Mar. 16, 1992;183(2):438-42.
Serrero et al., Prostaglandin F2alpha receptor (FP receptor) agonists are potent adipose differentiation inhibitors for primary culture of

(56) References Cited

OTHER PUBLICATIONS adipocyte precursors in defined medium. Biochem Biophys Res Commun. Apr. 7, 1997;233(1):200-2.

Shah et al., A cross-sectional survey of the association between bilateral topical prostaglandin analogue use and ocular adnexal features. PLoS One. May 1, 2013;8(5):e61638. doi: 10.1371/journal.pone.0061638. Print 2013. 7 pages.

Sharif et al., Agonist activity of bimatoprost, travoprost, latanoprost, unoprostone isopropyl ester and other prostaglandin analogs at the cloned human ciliary body FP prostaglandin receptor. J Ocul Pharmacol Ther. Aug. 2002;18(4):313-24.

Singh et al., Local deep tissue penetration of compounds after dermal application: structure-tissue penetration relationships. J Pharmacol Exp Ther. Nov. 1996;279(2):908-17.

Sjoquist et al., The pharmacokinetics of a new antiglaucoma drug, latanoprost, in the rabbit. Drug Metab Dispos. Aug. 1998;26(8):745-54.

Sjoquist et al., Ocular and systemic pharmacokinetics of latanoprost in humans. Surv Ophthalmol. Aug. 2002;47 Suppl 1:S6-12.

Tappeiner et al., [Orbital fat atrophy in glaucoma patients treated with topical bimatoprost—can bimatoprost cause enophthalmos?]. Klin Monbl Augenheilkd. May 2008;225(5):443-5. English abstract only.

Tong et al., Heightened expression of cyclooxygenase-2 and peroxisome proliferator-activated receptor-delta in human endometrial adenocarcinoma. Neoplasia. Nov.-Dec. 2000;2(6):483-90.

Tornqvist et al., Purification and some properties of a monoacylglycerol-hydrolyzing enzyme of rat adipose tissue. J Biol Chem. Feb. 10, 1976;251(3):813-9.

Tsuboi et al., Prostanoid EP4 receptor is involved in suppression of 3T3-L1 adipocyte differentiation. Biochem Biophys Res Commun. Sep. 24, 2004;322(3):1066-72.

Woodward et al., Prostamides (prostaglandin-ethanolamides) and their pharmacology. Br J Pharmacol. Feb. 2008;153(3):410-9. Epub Aug. 27, 2007.

Woodward et al., The pharmacology of bimatoprost (Lumigan™). Surv Ophthalmol. May 2001;45 Suppl 4:S337-45.

Yam et al., Bilateral deepening of upper lid sulcus from topical bimatoprost therapy. J Ocul Pharmacol Ther. Oct. 2009;25(5):471-2.

Ziegler, FDA Approves Latisse Eyelash Growth Product. Last accessed Jul. 24, 2012 at http://voices.yahoo.com/fda-approves-latisse-eyelash-growth-product-3520905.html?cat=39. 3 pages.

International Preliminary Report on Patentability, dated Oct. 4, 2016, in connection with Application No. PCT/US2015/037323.

Jordan, Tamoxifen: a most unlikely pioneering medicine. Nat Rev Drug Discov. Mar. 2003;2(3):205-13.

U.S. Appl. No. 11/712,839, filed Mar. 1, 2007, Grosskreutz et al.

U.S. Appl. No. 12/652,968, filed Jan. 6, 2010, Grosskreutz et al.

U.S. Appl. No. 14/180,074, filed Feb. 13, 2014, Grosskreutz et al.

U.S. Appl. No. 14/504,788, filed Oct. 2, 2014, Grosskreutz et al.

U.S. Appl. No. 14/838,049, filed Aug. 27, 2015, Grosskreutz et al.

U.S. Appl. No. 15/243,641, filed Aug. 22, 2016, Grosskreutz et al.

U.S. Appl. No. 15/790,630, filed Oct. 23, 2017, Grosskreutz et al.

U.S. Appl. No. 16/381,767, filed Apr. 11, 2019, Grosskreutz et al.

U.S. Appl. No. 13/548,482, filed Jul. 13, 2012, Kalayoglu et al.

U.S. Appl. No. 13/782,659, filed Mar. 1, 2013, Kalayoglu et al.

U.S. Appl. No. 14/363,923, filed Jun. 9, 2014, Kalayoglu et al.

U.S. Appl. No. 14/932,445, filed Nov. 4, 2015, Kalayoglu et al.

U.S. Appl. No. 15/864,980, filed Jan. 8, 2018, Kalayoglu et al.

U.S. Appl. No. 14/889,093, filed Nov. 4, 2015, Singer et al.

U.S. Appl. No. 14/575,873, filed Dec. 18, 2014, Kalayoglu et al.

U.S. Appl. No. 14/702,365, filed May 1, 2015 Kalayoglu et al.

U.S. Appl. No. 15/843,272, filed Dec. 15, 2017, Singer et al.

U.S. Appl. No. 16/785,892, filed Feb. 10, 2020, Singer et al.

U.S. Appl. No. 13/980,179, filed Oct. 18, 2013, Kalayoglu.

U.S. Appl. No. 14/509,680, filed Oct. 8, 2014, Kalayoglu.

U.S. Appl. No. 15/359,061, filed Nov. 22, 2016, Kalayoglu.

U.S. Appl. No. 15/321,241, filed Dec. 22, 2016, Singer et al.

PCT/US2015/037323, Oct. 4, 2016, International Preliminary Report on Patentability.

Latanoprost free acid
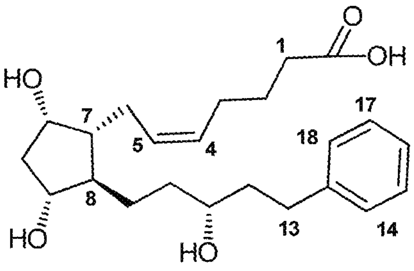
*carboxylic acid*
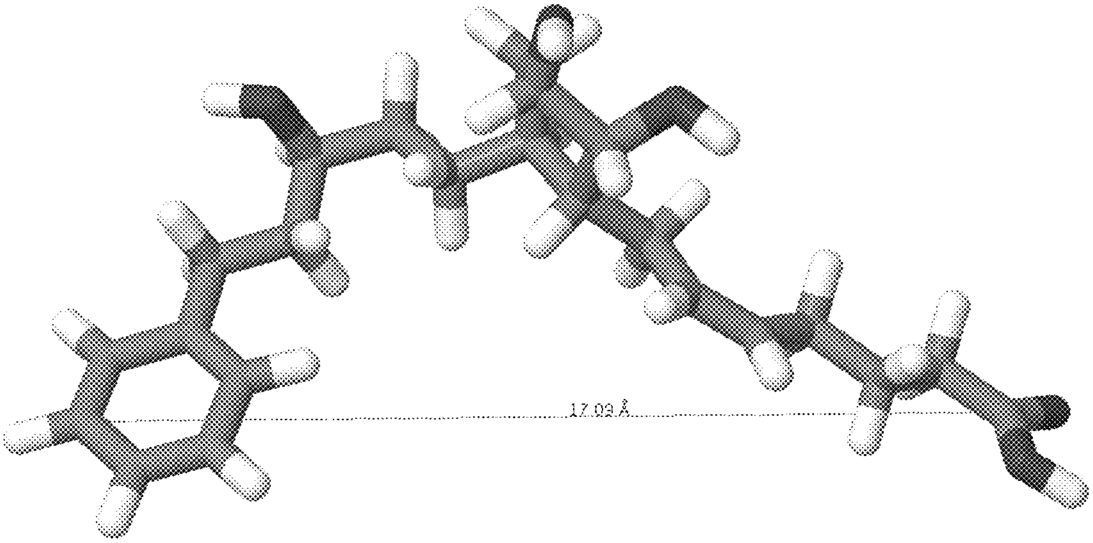

(continued)
Oleic acid
*overlaps with the northern aliphatic chain of latanoprost free acid*
*carboxylic acid*
*cis bond overlaps with the 1,2 substituted cyclopentyl ring of latanoprost free acid*
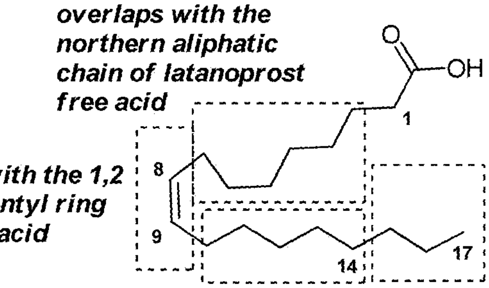
*overlaps with the phenyl ring of latanoprost free acid*
*overlaps with the southern aliphatic chain of latanoprost free acid*
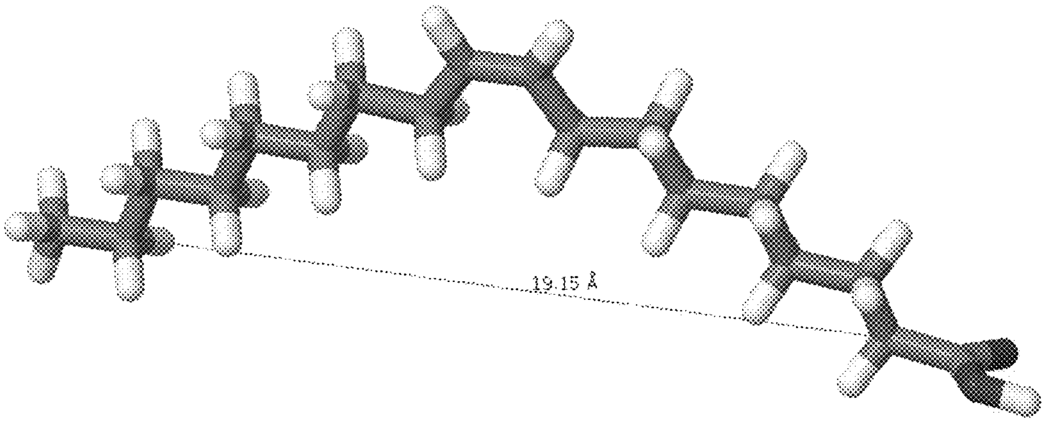

METHODS AND COMPOSITIONS FOR TOPICAL DELIVERY OF PROSTAGLANDINS TO SUBCUTANEOUS FAT

RELATED APPLICATIONS

This application is a continuation of and claims priority under 35 U.S.C. § 120 to U.S. Application, U.S. Ser. No. 14/889,093, filed Nov. 4, 2015; which is a national stage filing under 35 U.S.C. § 371 of international PCT application, PCT/US2014/038067, filed May 15, 2014; which claims priority under 35 U.S.C. § 119(e) to U.S. provisional patent application, U.S. Ser. No. 61/823,659, filed May 15, 2013; the entire contents of each of which is incorporated herein by reference.

FIELD OF THE INVENTION

The present invention relates to methods and compositions for topically delivering a therapeutically effective amount of a prostaglandin FP receptor agonist (a PFPRA compound) to adipocytes under the skin. The PFPRA compound can be, for example, an analog of prostaglandin F2α. The therapeutic effect is, for example, reduction of excess fat under the skin, for example, excess subcutaneous fat of the face, neck, chin, submental region, limbs, breast, abdomen, hips, etc. More specifically, the invention relates to new compositions comprising a PFPRA compound and a fatty acid (e.g., oleic acid) and optionally further comprising one or more organic alcohols (e.g., ethanol and/or propylene glycol), and methods comprising applying the composition(s) to the skin.

Experimentally, in comparison to a wide array of other compositions tested, the compositions disclosed herein demonstrate exceptional efficiency in delivering certain PFPRA compounds across skin in vitro, in delivering a therapeutically effective amount to adipose tissue in vivo, and/or in reducing subcutaneous fat in vivo. In theory, this efficiency may owe to the similar structure and polarity between the PFPRA compound (e.g., latanoprost) or an active metabolite thereof (e.g., latanoprost free acid) and the fatty acid (e.g., oleic acid), as described herein. The compositions are well-tolerated, non-irritating, and aesthetically pleasing. Furthermore, the compositions are physically and chemically stable and readily manufactured.

BACKGROUND OF THE INVENTION

Excess body fat is an important cause of human disease, disability, and cosmetic disturbance. For many people excess body fat is also a source of psychosocial distress and reduced self-esteem.

Excess body fat may be diffuse or concentrated on particular portion(s) of the body. Of particular importance is excess body fat of the face, for example, of the eyelids, chin, or jowls. Other important sites of excess body fat can include, for example, the arms, abdomen, buttocks, hips, chest, thighs, and neck. Excess body fat can also involve excessive breast tissue on a woman or on a man, i.e., gynecomastia. Excess body fat can be located within or near the eyelids, and topical treatment of such fat requires a composition that is safe for application near the eyes, i.e. an ophthalmic and/or ophthalmically compatible formulation. Local accumulations of body fat may result from constitutional factors, disease, hormonal status, or as side effects of medication or other substances. Even in the absence of disease, cosmetic considerations apply to individuals who nevertheless perceive an excess of fat and wish to have it corrected. For example, excess submental fat, commonly known as "double chin," is not considered a disease; however, people with excess submental fat often appear less attractive and less youthful, and can have lower self-esteem as a result. Likewise, an individual may have excess subcutaneous fat on the anterior abdomen, excess subcutaneous fat on the oblique abdomen, e.g. above the iliac crests ("love handles"), excess chest fat, excess breast fat, excess buttocks fat, excess hip fat, excess thigh fat, excess leg fat, excess upper arm fat, excess check fat, excess neck fat, etc.

A number of medical conditions are considered to be causes of excess body fat. Examples include drug-induced obesity, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, and leptin deficiency or resistance. Disfiguring excess regional fat deposits, for example excess dorsocervical fat, may be found in conditions such as HIV lipodystrophy, Cushing syndrome and pseudo-Cushing syndrome (i.e., characteristic syndrome of excess body fat and other findings due to excessive endogenous or exogenous corticosteroid levels), other acquired lipodystrophies, familial lipodystrophies, lipoma, lipomatosis, and Madelung disease.

Medications known to cause excess body fat include cortisol and analogs, other corticosteroids, megace, sulfonylureas, antiretrovirals, tricyclic antidepressants, monoamine oxidase inhibitors, selective serotonin reuptake inhibitors, oral contraceptives, insulin, risperidone, clozapine, and thiazolidinediones.

Changes in hormonal status, including physiologic changes such as pregnancy or menopause, may result in excess body fat in a subject. Smoking cessation commonly leads to weight gain and excess body fat. Trauma may favor the accumulation of excess body fat by virtue of immobility or disuse of an extremity. Similar problems may affect a subject who is immobilized, for example due to an injury. Some tumors, for example lipomas and liposarcomas, are characterized by local collections of fat cells. Lipomatosis is any condition characterized by the formation of multiple lipomas on the body, e.g., familial multiple lipomatosis, adiposis dolorosis (Dercum's disease), pelvic lipomatosis, etc.

Even in the absence of underlying pathology, an individual may have cosmetic concerns about local or diffuse deposits of body fat. These can usually be attributed to constitutional or hereditary factors, developmental history, age, gender, diet, alcohol use, or other components of lifestyle. Individuals in such circumstances commonly wish to reduce the amount of fat on the face, eyelids, chin, arms, neck, abdomen, chest, breast, buttocks, hips, thighs, and/or legs. In some cases a local excess of fat can be due to fat prolapse, displacement, and/or migration, as in age-related orbital fat prolapse or descent of malar fat pads. Grave's ophthalmopathy (thyroid-related eye disease) is a condition that can be treated by reducing the volume of orbital fat.

A number of methods have been developed to reduce or remove excess body fat. It is helpful to classify these methods as extractive, metabolic, or adipolytic. Extractive methods, such as lipoplasty (e.g., liposuction) or local excision, are methods whereby fat is physically removed from areas of interest. Such methods are costly and may involve scars, postsurgical deformity or regression, discomfort, infection, and other adverse reactions.

In contrast to extractive methods, metabolic methods, which include systemic medications, nutritional supplements, devices, and exercise or other body treatment, seek to modify the subject's metabolism (e.g., whether caloric consumption, expenditure, or both) such that the subject incurs a net loss of fat. A disadvantage is that these methods typically cannot be directed to a particular part of the body. Another drawback is potential concomitant loss of water, carbohydrates, protein, vitamins, minerals, and other nutrients. Furthermore, traditional diet medications may have undesired side effects, for example palpitations, tremor, insomnia, and/or irritability in a subject who uses stimulants as appetite suppressants. Despite salubrious value, the traditional metabolic methods of diet and exercise are not practical for everybody.

Adipolytic methods aim to cause breakdown of adipocytes and/or their lipid contents. For example, fat deposits can be reduced by exposure to cold temperature or to deoxycholate, a solubilizer that lyses cell membranes and results in local necrosis. Drawbacks of these methods can include poor discrimination between adipose and other nearby tissues, barriers to delivery that require hypodermic needles or special equipment, and adverse effects such as necrosis, inflammation, and pain.

Compounds of the prostaglandin FP receptor agonist (PFPRA compound) class, e.g., latanoprost and tafluprost, can be administered to the skin to locally reduce adipose tissue under the skin, i.e., subcutaneous fat. See, e.g., U.S. Pat. No. 8,426,471 and U.S. Publication No. 2010/0234466, incorporated herein by reference. Developing topical delivery of the PFPRA compound poses significant challenges, since delivery to subcutaneous fat comprises delivery across the stratum corneum, epidermis, dermis, and dermal microcirculation, and into the fat below.

For example, the skin, in particular the stratum corneum, presents a formidable physical barrier to drug penetration. See, e.g., Dayan N, Delivery System Design in Topically Applied Formulations: An Overview, in Rosen M, Delivery System Handbook for Personal Care and Cosmetic Products, William Andrew, 2005, pp. 103-104. For any particular drug, the formulation must be selected empirically. The formulation must be physically and chemically compatible with the drug.

Furthermore, provided that a formulation enables a drug to cross the skin, to reach the subcutaneous fat it must also circumvent what is known as the "sink condition" of the dermal circulation. See, e.g., Dayan N, Delivery System Design in Topically Applied Formulations: An Overview, in Rosen M, Delivery System Handbook for Personal Care and Cosmetic Products, William Andrew, 2005, pp. 103-104; Kao J, In Vitro Assessment of Dermal Absorption, in Hobson D W, Dermal and Ocular Toxicology: Fundamentals and Methods, CRC Press, 1991, pp. 272-273. Because the dermis is invested by a network of capillaries with rapid blood flow, for any solute (e.g., drug) that penetrates the dermis, a wide concentration gradient is created between the skin and bloodstream. Thus, there is a strong tendency for drugs that penetrate into the dermis to diffuse rapidly down this gradient into the bloodstream. This sink phenomenon favors systemic delivery (e.g., to the bloodstream, as with a nicotine patch), but undermines attempts at local delivery (e.g., to subcutaneous fat, as in the present invention). No method of reasoning or prediction is available in the art to suggest which formulations, if any, can circumvent the sink condition. Therefore, the artisan must search for such formulations empirically, and without prior knowledge that such formulation even exists.

The formulation must also have a favorable systemic drug exposure profile, e.g., that avoids excessive levels of drug in the bloodstream. This requirement is rendered more difficult by the sink condition.

Additionally, the formulation should deliver the active ingredient with reasonable efficiency. One measure of efficiency is the ability to minimize the concentration of active ingredient in the finished product and still maintain the desired therapeutic effect. This has implications for manufacturability, cost of goods, and local safety and tolerability. Another measure of efficiency is the ability to minimize the dose frequency and still maintain the desired therapeutic effect, which has implications for patient convenience and product marketability.

As well, the formulation must cause little or no skin irritation. If applied to skin near the eye, e.g., the eyelid, the formulation is considered an ophthalmic formulation. Generally, an ophthalmic formulation must be sterile, e.g., according to Chapter <71> of the U.S. Pharmacopeia. Preferably, an ophthalmic formulation must also be free or essentially free of bacterial endotoxin, e.g. according to Chapter <85> of the U.S. Pharmacopeia, e.g., an endotoxin level of <10 EU (endotoxin units) per gram of composition. If applied to skin near the eye, the formulation must be ophthalmically compatible, i.e, the formulation must not cause clinically significant eye irritation, and must not be toxic to the eye, e.g., the ocular surface, e.g. the cornea. Irritation potential and ocular toxicity are studied empirically by standard preclinical models, or in human trials. Although the skin or eye irritation potential of individual inactive ingredients is generally known, combinations of inactive and active ingredients can cause unexpected irritation, which must be tested empirically.

Furthermore, the formulation must possess other qualities necessary to make a topical formulation and market it to consumers: ease of manufacture, physical and chemical stability, and commercially acceptable appearance, odor, and tactile qualities.

Therefore, there is a need for new compositions for topically delivering a PFPRA compound to adipose tissue under the skin.

SUMMARY OF THE INVENTION

It has now been discovered experimentally that certain compositions comprising, e.g., latanoprost and a fatty acid (e.g., oleic acid) provide exceptionally efficient delivery of the latanoprost and its active metabolite into subcutaneous fat, and thus have particular uses and advantages, as described herein. In theory, this efficiency may owe to the similar structure and polarity between the PFPRA compound (e.g., latanoprost) or active metabolite thereof (e.g., latanoprost free acid) and the fatty acid (e.g., oleic acid), as described herein. For example, it has been discovered that compositions comprising latanoprost in combination with oleic acid provide efficient delivery of the active metabolite of latanoprost (latanoprost free acid) into the subcutaneous fat. This may relate to the fact that latanoprost hydrolyzes to the active metabolite (latanoprost free acid) in the skin. See, e.g., Example 4. The therapeutic effect of this delivery is reduction of subcutaneous fat.

Thus, in one aspect, provided is a composition comprising a PFPRA compound, e.g., latanoprost or tafluprost and a fatty acid, e.g., oleic acid, e.g., useful in the reduction of subcutaneous fat. In certain embodiments, the concentration of the PFPRA compound in the composition is between about 0.0001 percent to about 1 percent by weight, inclusive, e.g., between about 0.05 percent and about 0.5 percent by weight, or between about 0.01 percent and about 0.1 percent by weight, of the total weight of the composition. In some embodiments, the final concentration of the fatty acid is between about 1 percent to about 20 percent by weight, inclusive, e.g., between about 1 percent and about 5 percent by weight, or between about 2 percent and about 4 percent by weight, of the total weight of the composition. In some embodiments, the composition further comprises one or more organic alcohols (e.g., ethanol and/or propylene glycol). In some embodiments, the final concentration of an organic alcohol is between about 5 percent and about 99 percent, inclusive, by weight of the total weight of the composition. In certain embodiments, the final concentration of an organic alcohol (e.g., propylene glycol) between about 5 percent and about 50 percent, inclusive, by weight of the total weight of the composition, e.g., between about 20 percent and about 30 percent by weight, or between about 25 percent and about 30 percent by weight, of the total weight of the composition. In certain embodiments, the final concentration of an organic alcohol (e.g., ethanol) between about 60 percent and about 80 percent, inclusive, by weight of the total weight of the composition. In certain embodiments, the composition comprises about 3 percent of a fatty acid (e.g., oleic acid) and one or more organic alcohols (e.g., 27% of propylene glycol and/or 65%-70% of ethanol) by weight of the total weight of the composition. In some embodiments, the composition further comprises water. In some embodiments, the composition further comprises glycerin. In certain embodiments, the composition is for use in reducing body fat in a subject. In certain embodiments, the composition is used in the manufacture of a medicament for reducing body fat in a subject.

In another aspect, provided is a method of reducing body fat in a subject, comprising topically administering a composition as described herein to a subject in need thereof. In yet another aspect, provided is a kit comprising a composition as described herein and instructions for use.

Other objects and advantages will become apparent to those skilled in the art from consideration of the ensuing Detailed Description, Examples, and Claims.

DESCRIPTION OF THE DRAWINGS

FIG. 1 depicts three-dimensional molecular models of oleic acid and latanoprost free acid in energy-minimized conformations (solved in vacuo). Carbon atoms are shown in gray and oxygen atoms in red; hydrogens are not shown. Measured end-to-end distances (between heavy atom centers) are 19.1 Å for oleic acid and 17.1 Å for latanoprost free acid.

DEFINITIONS

Chemical Definitions

Definitions of specific functional groups and chemical terms are described in more detail below. The chemical elements are identified in accordance with the Periodic Table of the Elements, CAS version, Handbook of chemistry and physics, 75$^{th}$ ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Certain compounds as described herein can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds as described herein are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre. Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_1$-6, $C_1$-5, $C_1$-4, $C_1$-3, $C_1$-2, $C_2$-6, $C_2$-5, $C_2$-4, $C_2$-3, $C_3$-6, $C_{3-5}$, $C_3$-4, $C_4$-6, $C_{4-5}$, and $C_{5-6}$ alkyl.

As used herein, "aliphatic" refers to an alkyl, alkenyl, alkynyl, or carbocyclyl group, as defined herein.

As used herein, alone or as part of another group, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently unsubstituted (an "unsubstituted alkyl") or substituted (a "substituted alkyl") are substituted with one or more substituents. In certain embodiments, the alkyl group is an unsubstituted $C_{1-6}$ alkyl (e.g., $—CH_3$). In certain embodiments, the alkyl group is a substituted $C_{1-6}$ alkyl.

As used herein "perhaloalkyl" or "halosubstituted alkyl" as defined herein refers to an alkyl group having from 1 to 10 carbon atoms wherein all of the hydrogen atoms are each independently replaced halogen, e.g., selected from fluoro, bromo, chloro or iodo ("$C_{1-10}$ perhaloalkyl"). In some embodiments, the alkyl moiety has 1 to 6 carbon atoms ("$C_{1-6}$ perhaloalkyl"). In some embodiments, the alkyl moiety has 1 to 5 carbon atoms ("$C_{1-5}$ perhaloalkyl 1"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include $—CF_3$, $—CF_2CF_3$, $—CF_2CF_2CF_3$, $—CCl_3$, $—CFCl_2$, $—CF_2Cl$ and the like.

As used herein, "alkyloxy" refers to an alkyl group, as defined herein, substituted with an oxygen atom, wherein the point of attachment is the oxygen atom. In certain embodiments, the alkyl group has 1 to 6 carbon atoms ("$C_{1-6}$ alkyloxy"). In some embodiments, the alkyl group has 1 to 4 carbon atoms ("$C_{1-4}$ alkyloxy"). Examples of $C_{1-4}$ alkyloxy groups include methoxy ($C_1$), ethoxy ($C_2$), propoxy ($C_3$), isopropoxy ($C_3$), butoxy ($C_4$), tert-butoxy ($C_5$) and the like. Examples of $C_{1-6}$ alkyloxy groups include the aforementioned $C_{1-4}$ alkyloxy groups as well as pentyloxy ($C_5$), isopentyloxy ($C_5$), neopentyloxy ($C_5$), hexyloxy ($C_6$) and the like. Unless otherwise specified, each instance of the alkyl moiety of the alkyloxy group is independently unsubstituted (an "unsubstituted alkyloxy") or substituted (a "substituted alkyloxy") with one or more substituents. In certain embodiments, the alkyloxy group is an unsubstituted $C_{1-6}$ alkyloxy. In certain embodiments, the alkyloxy group is a substituted $C_{1-6}$ alkyloxy.

As used herein, "alkylcarboxy" refers to a group of the formula $—C(═O)OR^a$ wherein $R^a$ is an alkyl group as defined herein. In certain embodiments, the alkyl of the alkylcarboxy group has 1 to 6 carbon atoms ("$C_{1-6}$ alkylcarboxy"). In some embodiments, the alkyl of the alkylcarboxy group has 1 to 5 carbon atoms ("$C_{1-5}$ alkylcarboxy"). In some embodiments, the alkyl of the alkylcarboxy group has 1 to 4 carbon atoms ("$C_{1-4}$ alkylcarboxy"). In some embodiments, the alkyl of the alkylcarboxy group has 1 to 3 carbon atoms ("$C_{1-3}$ alkylcarboxy"). In some embodiments, the alkyl of the alkylcarboxy group has 1 to 2 carbon atoms ("$C_{1-2}$ alkylcarboxy"). Unless otherwise specified, each instance of the alkyl of the alkylcarboxy group is independently unsubstituted (an "unsubstituted alkylcarboxy") or substituted (a "substituted alkylcarboxy") with one or more substituents. In certain embodiments, the alkylcarboxy group is an unsubstituted $C_{1-6}$ alkylcarboxy. In certain embodiments, the alkylcarboxy group is a substituted $C_{1-6}$ alkylcarboxy.

As used herein, alone or as part of another group, "alkenyl" refers to a radical of a straight-chain or branched hydrocarbon group having from 2 to 20 carbon atoms and one or more carbon-carbon double bonds ("$C_{2-20}$ alkenyl"). In some embodiments, an alkenyl group has 2 to 10 carbon atoms ("$C_{2-10}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-6}$ alkenyl. In certain embodiments, the alkenyl group is a substituted $C_{2-6}$ alkenyl.

As used herein, alone or as part of another group, "alkynyl" refers to a radical of a straight-chain or branched hydrocarbon group having from 2 to 20 carbon atoms and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atom ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$) and the like. Examples of $C_{2-6}$ alkenyl groups include the aforementioned $C_{2-4}$ alkynyl groups as well as pentynyl ($C_5$), hexynyl ($C_6$) and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-6}$ alkynyl. In certain embodiments, the alkynyl group is a substituted $C_{2-6}$ alkynyl.

As used herein, a "saturated or unsaturated acyclic hydrocarbon" refers to radical of a saturated or unsaturated, straight-chain or branched, hydrocarbon group having from 1 to 20 carbon atoms and optionally one or more carbon-carbon double or triple bonds. In certain embodiments, the hydrocarbon group is saturated. In some embodiments, the hydrocarbon group is unsaturated, and contains one or more carbon-carbon double or triple bonds. In some embodiments, the hydrocarbon group contains 1-10 carbon atoms. In certain embodiments, the hydrocarbon group contains 1-5 carbon atoms. In some embodiments, the hydrocarbon group contains 1-4 carbon atoms. In some embodiments, the hydrocarbon group contains 1-3 carbon atoms. In some embodiments, the hydrocarbon group contains 1-2 carbon atoms.

As used herein, "carbocyclyl" refers to a radical of a non-aromatic cyclic hydrocarbon group having from 3 to 7 ring carbon atoms ("$C_{3-7}$ carbocyclyl") and zero heteroatoms in the non-aromatic ring system. In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). Exemplary $C_{3-7}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), and the like. As the foregoing examples illustrate, in certain embodiments, the carbocyclyl group is either monocyclic ("monocyclic carbocyclyl") or polycyclic (e.g., containing a fused, bridged or Spiro ring system such as a bicyclic system ("bicyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with 1, 2, 3, 4, or 5 substituents as described herein. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-7}$ cycloalkyl groups include the aforementioned $C_{3-6}$ cycloalkyl groups as well as cycloheptyl ($C_7$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-7}$ cycloalkyl. In certain embodiments, the cycloalkyl group is a substituted $C_{3-7}$ cycloalkyl.

As used herein, alone or as part of another group, "heterocyclyl" refers to a radical of a 3- to 8-membered non-aromatic ring system having ring carbon atoms and 1 to 4 ring heteroatoms, wherein each heteroatom is independently selected from nitrogen, oxygen and sulfur ("3-8-membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-8 membered non-aromatic ring system having ring carbon atoms and 1-4 ring heteroatoms, wherein each heteroatom is independently selected from nitrogen, oxygen and sulfur ("5-8-membered heterocyclyl"). In some embodiments, a heterocyclyl group is a 5-6-membered non-aromatic ring system having ring carbon atoms and 1-4 ring heteroatoms, wherein each heteroatom is independently selected from nitrogen, oxygen and sulfur ("5-6-membered heterocyclyl"). In some embodiments, the 5-6-membered heterocyclyl has 1-3 ring heteroatoms selected from nitrogen, oxygen and sulfur. In some embodiments, the 5-6-membered heterocyclyl has 1-2 ring heteroatoms selected from nitrogen, oxygen and sulfur. In some embodiments, the 5-6-membered heterocyclyl has 1 ring heteroatom selected from nitrogen, oxygen and sulfur. Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-8-membered heterocyclyl. In certain embodiments, the heterocyclyl group is a substituted 3-8-membered heterocyclyl.

As used herein, alone or as part of another group, "aryl" refers to a radical of a monocyclic or polycyclic (e.g., bicyclic or tricyclic) 4n+2 aromatic ring system having 6-10 ring carbon atoms and zero heteroatoms provided in the aromatic ring system ("$C_{6-10}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as described herein. In certain embodiments, the aryl group is an unsubstituted $C_{6-10}$ aryl. In certain embodiments, the aryl group is a substituted $C_{6-10}$ aryl.

As used herein, alone or as part of another group, "heteroaryl" refers to a radical of a 5-14-membered monocyclic or polycyclic (e.g., bicyclic) 4n+2 aromatic ring system having 4-10 ring carbon atoms and 1-4 ring heteroatoms provided in the aromatic ring system, wherein each heteroatom is independently selected from nitrogen, oxygen and sulfur ("5-10-membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10-membered aromatic ring system having ring carbon atoms and 1-4 ring heteroatoms provided in the aromatic ring system, wherein each heteroatom is independently selected from nitrogen, oxygen and sulfur ("5-10-membered heteroaryl"). In some embodiments, a heteroaryl group is a 5-8-membered aromatic ring system having ring carbon atoms and 1-4 ring heteroatoms provided in the aromatic ring system, wherein each heteroatom is independently selected from nitrogen, oxygen and sulfur ("5-8-membered heteroaryl"). In some embodiments, a heteroaryl group is a 5-6-membered aromatic ring system having ring carbon atoms and 1-4 ring heteroatoms provided in the aromatic ring system, wherein each heteroatom is independently selected from nitrogen, oxygen and sulfur ("5-6-membered heteroaryl"). In some embodiments, the 5-6-membered heteroaryl has 1-3 ring heteroatoms selected from nitrogen, oxygen and sulfur. In some embodiments, the 5-6-membered heteroaryl has 1-2 ring heteroatoms selected from nitrogen, oxygen and sulfur. In some embodiments, the 5-6-membered heteroaryl has 1 ring heteroatom selected from nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-10-membered heteroaryl. In certain embodiments, the heteroaryl group is a substituted 5-10-membered heteroaryl.

Alkyl, alkenyl, alkynyl, carbocyclyl, heterocyclyl, aryl, and heteroaryl, referred to without the suffix "-ene," describe a monoradical of alkyl, alkenyl, alkynyl, carbocyclyl, heterocyclyl, aryl, or heteroaryl, respectively, and as defined herein, wherein the monoradical is directly attached to a parent molecule or to another group by one bond (e.g., one single or double bond). Monoradical groups, as defined herein, may also be optionally substituted. Groups referred to with the suffix "-ene", such as alkylene, alkenylene, alkynylene, carbocyclylene, heterocyclylene, arylene and heteroarylene groups, describe a diradical of alkyl, alkenyl, alkynyl, carbocyclyl, heterocyclyl, aryl, or heteroaryl, respectively, and as defined herein, wherein the diradical is between and directly attached to two groups (e.g., between the parent molecule and another group) by two bonds (e.g., single or double bonds). Diradical groups may also be optionally substituted.

Alkyl, alkenyl, alkynyl, carbocyclyl, heterocyclyl, aryl and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group (e.g., 1, 2, 3, 4, or 5 positions), and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(OR$^{cc}$)R$^{bb}$, —SH, —SR$^{aa}$, —SSR$^{cc}$, —C(═O)R$^{aa}$, —CO$_2$H, —CHO, —C(OR$^{cc}$)$_2$, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —C(═NR$^{bb}$)R$^{aa}$, —C(═NR$^{bb}$)OR$^{aa}$, —OC(═NR$^{bb}$)R$^{aa}$, —OC(═NR$^{bb}$)OR$^{aa}$, (═NR$^{bb}$)N(R$^{bb}$)$_2$, OC(═NR$^{bb}$)N(R$^{bb}$)$_2$, —NR$^{bb}$C(═NR$^{bb}$)N(R$^{bb}$)$_2$, —C(═O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(═O)R$^{aa}$, —OS(═O)R$^{aa}$, —Si(R$^{aa}$)$_3$, —OSi(R$^{aa}$)$_3$—C(═S)N(R$^{bb}$)C(═O)SR$^{aa}$, —C(═S)SR$^{aa}$, —SC(═S)SR$^{aa}$, —SC(═O)SR$^{aa}$, —SC(═O)OR$^{aa}$, —OC(═O)SR$^{aa}$, —SC(═O)R$^{aa}$, —P(═O)$_2$R$^{aa}$, —OP(═O)$_2$R$^{aa}$, —P(═O)(R$^{aa}$)$_2$, —OP(═O)(R$^{aa}$)$_2$, —OP(═O)(OR$^{cc}$)$_2$, —P(═O)$_2$N(R$^{bb}$)$_2$, —OP(═O)$_2$N(R$^{bb}$)$_2$, —P(═O)(NR$^{bb}$)$_2$, —OP(═O)(NR$^{bb}$)$_2$, —NR$^{bb}$P(═O)(OR$^{cc}$)$_2$, —NR$^{bb}$P(═O)(NR$^{bb}$)$_2$, —P(R$^{cc}$)$_2$, —P(R$^{cc}$)$_3$, OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group ═O, ═S, ═NN(R$^{bb}$)$_2$, ═NNR$^{bb}$C(═O)R$^{aa}$, ═NNR$^{bb}$C(═O)OR$^{aa}$, ═NNR$^{bb}$S(═O)$_2$R$^{aa}$, ═NR$^{bb}$, or ═NOR$^{aa}$;

each instance of R$^{aa}$ is, independently, selected from C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{aa}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, C$_{1-6}$ alkyl, C$_{2-45}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{bb}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from hydrogen, C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{cc}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(OR$^{ee}$)R$^{ff}$, —SH, —SR$^{ee}$, —SSR$^{ee}$, —C(═O)R$^{ee}$, —CO$_2$H, —C(═O)OR$^{ee}$, —OC(═O)R$^{ee}$, —OC(═O)OR$^{ee}$, —C(═O)N(R$^{ff}$)$_2$, —OC(═O)N(R$^{ff}$)$_2$, —NR$^{ff}$C(═O)R$^{ee}$, —NR$^{ff}$CO$_2$R$^{ee}$, —NR$^{ff}$C(═O)N(R$^{ff}$)$_2$, —C(═NR$^{ff}$)OR$^{ee}$, —OC(═NR$^{ff}$)R$^{ee}$, —OC(═NR$^{ff}$)OR$^{ee}$, —C(═NR$^{ff}$)N(R$^{ff}$)$_2$, —OC(═NR$^{ff}$)N(R$^{ff}$)$_2$, —NR$^{ff}$C(═NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(═O)R$^{ee}$, —Si(R$^{ee}$)$_3$, —OSi(R$^{ee}$)$_3$, —C(═S)N(R$^{ff}$)$_2$, —C(═O)SR$^{ee}$, —C(═S)SR$^{ee}$, —SC(═S)SR$^{ee}$, —P(═O)$_2$R$^{ee}$, —P(═O)(R$^{ee}$)$_2$, —OP(═O)(R$^{ee}$)$_2$, —OP(═O)(OR$^{ee}$)$_2$, C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form ═O or ═S;

each instance of R$^{ee}$ is, independently, selected from C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{2-6}$ alkenyl, C$_{2-6}$ alkynyl, C$_{3-7}$ carbocyclyl, 3-8-membered heterocyclyl, C$_{6-10}$ aryl, and 5-10-membered heteroaryl, or two R$^{ff}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(═O)(C$_{1-6}$ alkyl), —CO$_2$H, —CO$_2$(C$_{1-6}$ alkyl), —OC(═O)(C$_{1-6}$ alkyl), —OCO$_2$(C$_{1-6}$ alkyl), —C(═O)NH$_2$, —C(═O)N(C$_{1-6}$ alkyl)$_2$, —OC(═O)NH(C$_{1-6}$ alkyl), —NHC(═O)(C$_{1-6}$ alkyl), —N(C$_{1-6}$ alkyl)C(═O)(C$_{1-6}$ alkyl), —NHCO$_2$(C$_{1-6}$ alkyl), —NHC(═O)N(C$_{1-6}$ alkyl)$_2$, —NHC(═O)NH(C$_{1-6}$ alkyl), —NHC(═O)NH$_2$, —C(═NH)O(C$_{1-6}$ alkyl), —OC(═NH)(C$_{1-6}$ alkyl), —OC(═NH)OC$_{1-6}$ alkyl, —C(═NH)N(C$_{1-6}$ alkyl)$_2$, —C(═NH)NH(C$_{1-6}$ alkyl), —C(═NH)NH$_2$, —OC(═NH)N(C$_{1-6}$ alkyl), —OC(NH)NH(C$_{1-6}$ alkyl), —OC(NH)NH$_2$, —NHC(NH)N(C$_{1-6}$ alkyl), —NHC(═NH)NH$_2$, —NHSO$_2$ ($C_{1-6}$ alkyl), —$SO_2N(C_{1-6}$ alkyl), —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$, —C(=S)N($C_{1-6}$ alkyl$)_2$, C(=S)NH ($C_{1-6}$ alkyl), C(=S)$NH_2$, —C(=O)S($C_{1-6}$ alkyl), —C(=S) $SC_{1-6}$ alkyl, —SC(=S)$SC_{1-6}$ alkyl, —P(=O$)_2$($C_{1-6}$ alkyl), —P(=O)($C_{1-6}$ alkyl), —OP(=O)($C_{1-6}$ alkyl), —OP(=O) ($OC_{1-6}$ alkyl), $C_{1-6}$ alkyl, $C_{2-6}$ alkenyl, $C_{2-6}$ alkynyl, $C_{3-7}$ carbocyclyl, 3-8-membered-heterocyclyl, $C_{6-10}$ aryl, and 5-10-membered heteroaryl; or two geminal $R^{gg}$ substituents can be joined to form =O or =S.

In certain embodiments, the carbon atom substituent is selected from the group consisting of halogen, —CN, —$NO_2$, —$N_3$, —$SO_2H$, —$SO_3H$, —OH, —$OR^{aa}$, —N($R^{bb}$)$_2$, —SH, —$SR^{aa}$, —C(=O)$R^{aa}$, —$CO_2H$, —CHO, —$CO_2R^{ss}$, —OC(=O)$R^{ss}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —S(=O)$R^{aa}$, —OS(=O)$R^{aa}$, —$Si(R^{aa})_3$, $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

As used herein, the term "hydroxyl" or "hydroxy" refers to the group —OH. The term "substituted hydroxyl" or "substituted hydroxy," by extension, refers to a hydroxyl group wherein the oxygen atom is substituted with a group other than hydrogen, e.g., selected from —$OR^{aa}$, —ON($R^{bb}$)$_2$, —OC(=O)$R^{aa}$, —OC(=O)$SR^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —$OSi(R^{aa})_3$, —$OP(R^{cc})_2$, —$OP(R^{cc})_3$, —OP(=O)$_2R^{aa}$, —OP(=O)($R^{aa}$)$_2$, —OP(=O)($OR^{aa}$)$_2$, —OP(=O)$_2$N($R^{bb}$)$_2$, and —OP(=O)($NR^{bb}$)$_2$, wherein $R^{aa}$, $R^{bb}$, and $R^{cc}$ are as defined herein.

As used herein, the term "thiol" or "thio" refers to the group —SH. The term "substituted thiol" or "substituted thio," by extension, refers to a thiol group wherein the sulfur atom is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

As used herein, the term, "amino" refers to the group —$NH_2$.

As used herein, the term "substituted amino" refers to a monosubstituted, disubstituted, or trisubstituted amino group, as defined herein.

As used herein, the term "monosubstituted amino" refers to an amino group substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)($OR^{cc}$)$_2$, and —NHP(=O)($NR^{bb}$)$_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group substituted with two groups other than hydrogen, and includes groups selected from —N($R^{bb}$)$_2$, —$NR^{bb}$ C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)($OR^{cc}$)$_2$, and —$NR^{bb}$P(=O)($NR^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "sulfonyl" refers to a group selected from —S(=O)$_2$OH, —S(=O)$_2$N($R^{bb}$)$_2$, —S(=O)$_2$ $R^{aa}$, and —S(=O)$_2OR^{aa}$, wherein $R^{aa}$ and $R^{bb}$ are as defined herein.

As used herein, the term "sulfinyl" refers to —S(=O)OH and —S(=O)$R^{aa}$, wherein $R^{aa}$ is as defined herein.

As used herein, the term "carbonyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2H$), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)$NR^{bb}SO_2R^{aa}$, —C(=S)N($R^{bb}$)$_2$), and imines (—C(=$NR^{bb}$)$R^{aa}$, —C(=$NR^{bb}$)$OR^{aa}$), —C(=$NR^{bb}$)N($R^{bb}$)$_2$), wherein $R^{aa}$ and $R^{bb}$ are as defined herein.

As used herein, the term "silyl" refers to the group —$Si(R^{aa})_3$, wherein $R^{aa}$ is as defined herein.

As used herein, the term "boronyl" refers to boranes, boronic acids, boronic esters, borinic acids, and borinic esters, e.g., boronyl groups of the formula —B($R^{aa}$)$_2$, —B($OR^{cc}$)$_2$, and —$BR^{aa}$($OR^{cc}$), wherein $R^{aa}$ and $R^{cc}$ are as defined herein.

As used herein, the term "phosphino" refers to the group —P($R^{cc}$)$_3$, wherein $R^{cc}$ is as defined herein. An exemplary phosphino group is triphenylphosphine.

As used herein, the term "halo" or "halogen" refers to fluorine (fluoro, —F), chlorine (chloro, —Cl), bromine (bromo, —Br), or iodine (iodo, —I).

As used herein, "nitro" refers to the group —$NO_2$.

As used herein, "cyano" refers to the group —CN.

As used herein, "azido" refers to the group —$N_3$.

As used herein, "oxo" refers to the group =O.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —N($R^{cc}$)$_2$, —CN, —C(=O)$R^{aa}$, —C(=O)N($R^{aa}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)$_2R^{aa}$, —P(=O)($R^{aa}$)$_2$, —P(=O)$_2$N($R^{cc}$)$_2$, —P(=O)($NR^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an "amino protecting group". Amino protecting groups include, but are not limited to, —OH, —$OR^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc}$)$_2$, —$SO_2N(R^{cc})_2$, —$SO_2$12", —$SO_2OR^{cc}$, —$SOR^{aa}$, —C(=S)N($R^{cc}$)$_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in*

*Organic Synthesis*, T. W. Greene and P. G. M. Wuts, 3rd edition, John Wiley & Sons, 1999, incorporated herein by reference.

For example, amino protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(═O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylypethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), in-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl) methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyeethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(═O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STAB ASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on the oxygen atom is an "oxygen protecting group". Oxygen protecting groups include, but are not limited to —$R^{aa}$, —N($R^{bb}$)$_2$, —C(═O)$R^{aa}$, —C(═O)O$R^{aa}$, —C(═O)S$R^{aa}$, —C(═O)N($R^{bb}$)$_2$, —C(═N$R^{bb}$)$R^{aa}$, —C(═N$R^{bb}$)O$R^{aa}$, —C(═N$R^{bb}$)N($R^{bb}$)$_2$, —S(═O)$R^{aa}$, —SO$_2R^{aa}$, —Si($R^{aa}$)$_3$, —P($R^{cc}$)$_2$, —P($R^{cc}$)$_3$, —P(═O)$_2R^{aa}$, —P(═O)

$(R^{aa})_2$, —P(=O)($OR^{cc}$)$_2$, —P(=O)$_2$N($R^{bb}$)$_2$, and —P(=O)($NR^{bb}$)$_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester; 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, a-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, the substituent present on an sulfur atom is an sulfur protecting group (also referred to as a thiol protecting group). Sulfur protecting groups include, but are not limited to, —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$) $R^{aa}$, N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, the Examples and in the Claims. The invention is not intended to be limited in any manner by the above exemplary listing of substituents.

As used herein, the terms "salt", "acceptable salt", or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "prodrug" means a compound that can hydrolyze, oxidize, or otherwise react under biological conditions (e.g., in vitro or in vivo enzymatic conditions) to provide a pharmacologically active compound. In certain cases, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

Other Definitions

"Disease", "disorder," and "condition" are used interchangeably herein.

As used herein, an "individual" or "subject" to which administration is contemplated includes, but is not limited to, humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the mammal is a human.

As used herein, "local administration" or "administering locally" or "local effect" means administration/application of the active ingredient or active metabolite thereof directly, or in proximity to, a part of the body, tissue, or lesion where said active substance is intended to exert its action. This may include, for example, topical administration to a part of the skin.

As used herein, unless otherwise specified, "topical administration" or "topically" means application to the surface of the skin, e.g., in a non-invasive manner.

As used herein, and unless otherwise specified, a "therapeutically effective amount" "an amount sufficient" or "sufficient amount" of a compound means the level, amount or concentration of the compound needed to treat a disease, disorder or condition, or to reduce or lower a particular parameter (e.g., body fat) in the body of a subject, without causing significant negative or adverse side effects to body or the treated tissue. The term "therapeutically effective amount" can encompass an amount that improves overall therapy, reduces or avoids symptoms or causes of disease or condition, or enhances the therapeutic efficacy of another therapeutically active agent.

As used herein, the terms "reduce", "reduction", "reducing", "lower", or "lowering" means to diminish or lessen the volume, size, mass, bulk, density, amount, and/or quantity of a substance (e.g., body fat, adipose tissue) in the body of a subject.

As used herein, the term "eliminate" means to completely remove any unwanted or undesired volume, size, mass, bulk, density, amount, and/or quantity of a substance (e.g., excess body fat, excess adipose tissue) in the body of a subject.

As used herein, "suffer", "suffers" or "suffering from" refers to a subject diagnosed with a particular disease or condition. As used herein, "likely to suffer" refers to a subject who has not been diagnosed with a particular disease or condition by a medical practitioner, but has a predisposition (e.g., genetic and/or physiologic predisposition), or exhibits signs or symptoms of the disease or condition.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition.

As used herein, unless otherwise specified, the terms "prevent," "preventing" and "prevention" contemplate an action that occurs before a subject begins to suffer from the specified disease or condition, which inhibits or reduces the severity of the disease or condition.

Conditions for which treatment and prevention are contemplated may be further classified as a medical condition or a cosmetic condition. A "medical condition," as used herein, refers to an abnormal condition that affects the body. A "cosmetic condition," as used herein, refers to a condition other than a medical condition that affects the physical appearance of the body. A cosmetic condition can occur, for example, due to normal processes in a body, such as aging, pregnancy, puberty, and exposure to the sun or the elements, or due to normal features of a body, such as inherited facial features or body shapes that are found in healthy individuals. Various medical and cosmetic conditions are described herein. A "cosmetic method" refers to a method or procedure intended to ameliorate a cosmetic condition in the subject, e.g., for the beautification of the subject's body or a part thereof, and a "cosmetic composition" is contemplated useful for such purpose. A "therapeutic method" refers to a method or procedure intended to treat or prevent a medical condition, and a "pharmaceutical composition" is contemplated useful for such purpose. However, while pharmaceutical compositions are contemplated useful for therapeutic and prophylactic purposes, and cosmetic compositions are contemplated useful for cosmetic purposes, there is overlap between the two compositions in terms of use of the composition. For example, a pharmaceutical composition is also contemplated useful for beautification purposes.

As used herein, unless otherwise specified, "excess submental fat" means excess fat on the body region including the mentum, the underside of the jaw, and the anterior neck, for example to the level of the inferior border of the cricoid.

As used herein, unless otherwise specified, "steatoblepharon" refers to a condition characterized by excess fat of the eyelids and/or periorbital tissue. The excess fat can be due to prolapse of orbital or periorbital fat. Steatoblepharon can occur in the lower or upper eyelid, or both. Steatoblepharon can be considered a cause of "eye bags."

The presence, amount, or severity of excess fat can be assessed objectively, e.g., by magnetic resonance imaging, computed tomography, biopsy, or skin calipers, or subjectively, e.g., by a clinician, a patient, or other observer, optionally with reference to a photonumeric, verbal, or descriptive scale or classification system, e.g., a five-step severity scale.

DETAILED DESCRIPTION OF CERTAIN EMBODIMENTS OF THE INVENTION

The present invention relates to new stable, manufacturable, well-tolerated, aesthetically pleasing compositions that, when applied to the skin, deliver a therapeutically effective amount of a prostaglandin FP receptor agonist (PFPRA compound), e.g., a prostaglandin F2α analog, e.g., latanoprost or tafluprost, to subcutaneous fat. More specifically, the invention relates to compositions for delivery of a PFPRA compound to subcutaneous fat, comprising a PFPRA compound and a fatty acid, e.g., oleic acid. The formulations are useful for local reduction of subcutaneous fat, and for other therapeutic uses as described herein. The invention also relates to methods for locally reducing body fat, comprising administering the inventive compositions to the skin.

As described herein, no theoretical framework was available to the inventors to select or improve a topical composition for delivering a PFPRA compound to subcutaneous fat. Rather, the inventors found it necessary to test a wide range of conditions both in vitro and in vivo, with different formulation components at different concentrations and in different combinations. This testing led to the discovery that inclusion of oleic acid in the composition conferred exceptionally better performance for delivery of a PFPRA compound and reduction of subcutaneous fat compared to, for example, use of 1,3-butanediol, diethylene glycol monoethyl ether, dimethylsulfoxide, ethanol, glycerol monooleate, hydroxypropyl cellulose, lauryl lactate, methyl laurate, oleyl alcohol, polysorbate 80, propylene glycol, and combinations thereof.

Without wishing to be bound by any particular theory, the special properties conferred by combining oleic acid and a PFPRA may owe to certain similarities between oleic acid and the PFPRA compound or active metabolites thereof, i.e., similar structure and similar polarity. For example, the active metabolite of latanoprost, latanoprost free acid, and oleic acid are both carboxylic acids of similar structure and polarity. As shown in FIG. 1, in their energy-minimized conformations, both compounds have a similar three-dimensional structure. Furthermore, according to this structural hypothesis, latanoprost free acid per se could serve as a penetration enhancer in this context, in that its 5-cis double bond (likewise present in most other PFPRA compounds) may improve the penetration characteristics of oleic acid, as the structural kink of unsaturated molecules is known to interfere with close packing of the phospholipid bilayer and can thereby improve penetration.

In some embodiments, the composition comprises a PRPRA compound carboxylic acid and a fatty acid, wherein both acids comprise the same aliphatic (—$R^{FA1}$) tail. In some embodiments, the composition comprises a PRPRA compound carboxylic acid and a fatty acid, wherein both acids comprise aliphatic tails ($R^{FA1}$) of similar chain length.

Furthermore, according to the above theory, the skilled artisan will appreciate that in certain embodiments, oleic acid can be substituted by one or more fatty acids of similar structure, e.g., wherein the aliphatic moiety of the fatty acid ($R^{FA1}$) is optionally substituted $C_{10}$-$C_{20}$ alkyl or optionally substituted $C_{10}$-$C_{20}$ alkenyl.

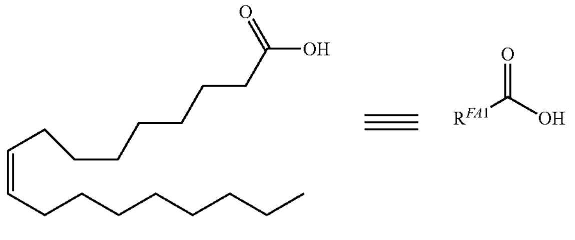

oleic acid

In certain embodiments, $R^{FA1}$ is an optionally substituted $C_{10}$-$C_{19}$ alkyl, $C_{10}$-$C_{18}$ alkyl, $C_{10}$-$C_{17}$ alkyl, $C_{10}$-$C_{16}$ alkyl, $C_{10}$-$C_{15}$ alkyl, $C_{10}$-$C_{14}$ alkyl, $C_{10}$-$C_{13}$ alkyl, $C_{11}$-$C_{20}$ alkyl, $C_{11}$-$C_{19}$ alkyl, $C_{11}$-$C_{18}$ alkyl, $C_{11}$-$C_{17}$ alkyl, $C_{11}$-$C_{16}$ alkyl, $C_{11}$-$C_{15}$ alkyl, $C_{11}$-$C_{14}$ alkyl, $C_{11}$-$C_{13}$ alkyl, $C_{12}$-$C_{19}$ alkyl, $C_{12}$-$C_{18}$ alkyl, $C_{12}$-$C_{17}$ alkyl, $C_{12}$-$C_{16}$ alkyl, $C_{12}$-$C_{15}$ alkyl, $C_{12}$-$C_{14}$ alkyl, $C_{12}$-$C_{13}$ alkyl, $C_{13}$-$C_{20}$ alkyl, $C_{13}$-$C_{19}$ alkyl, $C_{13}$-$C_{18}$ alkyl, $C_{13}$-$C_{17}$ alkyl, $C_{13}$-$C_{16}$ alkyl, $C_{13}$-$C_{15}$ alkyl, $C_{13}$-$C_{14}$ alkyl, $C_{14}$-$C_{20}$ alkyl, $C_{14}$-$C_{19}$ alkyl, $C_{14}$-$C_{18}$ alkyl, $C_{14}$-$C_{17}$ alkyl, $C_{14}$-$C_{16}$ alkyl, $C_{14}$-$C_{15}$ alkyl, $C_{15}$-$C_{20}$ alkyl, $C_{15}$-$C_{19}$ alkyl, $C_{15}$-$C_{18}$ alkyl, $C_{15}$-$C_{17}$ alkyl, or $C_{15}$-$C_{16}$ alkyl. In certain embodiments, $R^{FA1}$ is a straight chain (unbranched) alkyl group. In certain embodiments, $R^{FA1}$ is an unsubstituted alkyl group, i.e., comprising only carbon and hydrogen atoms. In certain embodiments, $R^{FA1}$ is a substituted alkyl group, e.g., substituted by halogen atoms.

In certain embodiments, $R^{FA1}$ is an optionally substituted $C_{10}$-$C_{19}$ alkenyl, $C_{10}$-$C_{18}$ alkenyl, $C_{10}$-$C_{17}$ alkenyl, $C_{10}$-$C_{16}$ alkenyl, $C_{10}$-$C_{15}$ alkenyl, $C_{10}$-$C_{14}$ alkenyl, $C_{10}$-$C_{13}$ alkenyl, $C_{11}$-$C_{20}$ alkenyl, $C_{11}$-$C_{19}$ alkenyl, $C_{11}$-$C_{18}$ alkenyl, $C_{11}$-$C_{17}$ alkenyl, $C_{11}$-$C_{16}$ alkenyl, $C_{11}$-$C_{15}$ alkenyl, $C_{11}$-$C_{14}$ alkenyl, $C_{11}$-$C_{13}$ alkenyl, $C_{12}$-$C_{19}$ alkenyl, $C_{12}$-$C_{18}$ alkenyl, $C_{12}$-$C_{17}$ alkenyl, $C_{12}$-$C_{16}$ alkenyl, $C_{12}$-$C_{15}$ alkenyl, $C_{12}$-$C_{14}$ alkenyl, $C_{12}$-$C_{13}$ alkenyl, $C_{13}$-$C_{20}$ alkenyl, $C_{13}$-$C_{19}$ alkenyl, $C_{13}$-$C_{18}$ alkenyl, $C_{13}$-$C_{17}$ alkenyl, $C_{13}$-$C_{16}$ alkenyl, $C_{13}$-$C_{15}$ alkenyl, $C_{13}$-$C_{14}$ alkenyl, $C_{14}$-$C_{20}$ alkenyl, $C_{14}$-$C_{19}$ alkenyl, $C_{14}$-$C_{18}$ alkenyl, $C_{14}$-$C_{17}$ alkenyl, $C_{14}$-$C_{16}$ alkenyl, $C_{14}$-$C_{15}$ alkenyl, $C_{15}$-$C_{20}$ alkenyl, $C_{15}$-$C_{19}$ alkenyl, $C_{15}$-$C_{18}$ alkenyl, $C_{15}$-$C_{17}$ alkenyl, $C_{15}$-$C_{16}$ alkenyl. In certain embodiments, $R^{FA1}$ is a unbranched alkenyl group. In certain embodiments, $R^{FA1}$ is an unsubstituted alkenyl group, i.e., comprising only carbon and hydrogen atoms. In certain embodiments, $R^{FA1}$ is a substituted alkenyl group, e.g., substituted by halogen atoms. In certain embodiments, $R^{FA1}$ is an alkenyl group comprising 1, 2, 3, or 4 double bonds, each independently cis or trans.

In certain embodiments, $R^{FA1}$ is an alkenyl group comprising at least one cis double bond, e.g., 1, 2, 3, or 4 cis double bonds. In certain embodiments, $R^{FA1}$ is an alkenyl group of formula (a):

(a)

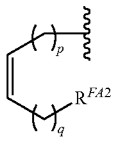

wherein:

p is an integer between 2 and 8, inclusive;

q is an integer between 1 and 8, inclusive; and $R^{FA2}$ is an optionally substituted $C_1$-$C_{10}$ alkyl, or an optionally substituted $C_2$-$C_{10}$alkenyl, provided the sum of carbons of formula (a) does not exceed 20.

In certain embodiments, $R^{FA2}$ is an optionally substituted $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_{10}$ alkyl, $C_2$-$C_9$ alkyl, $C_2$-$C_8$ alkyl, $C_2$-$C_7$ alkyl, $C_2$-$C_6$ alkyl, $C_2$-$C_5$ alkyl, $C_2$-$C_4$ alkyl, $C_2$-$C_3$ alkyl, $C_3$-$C_{10}$ alkyl, $C_3$-$C_9$ alkyl, $C_3$-$C_8$ alkyl, $C_3$-$C_7$ alkyl, $C_3$-$C_6$ alkyl, $C_3$-$C_5$ alkyl, $C_3$-$C_4$ alkyl, $C_4$-$C_{10}$ alkyl, $C_4$-$C_9$ alkyl, $C_4$-$C_8$ alkyl, $C_4$-$C_7$ alkyl, $C_4$-$C_6$ alkyl, $C_4$-$C_5$ alkyl, $C_5$-$C_{10}$ alkyl, $C_5$-$C_9$ alkyl, $C_5$-$C_8$ alkyl, $C_5$-$C_7$ alkyl, $C_5$-$C_6$ alkyl, $C_6$-$C_{10}$ alkyl, $C_6$-$C_9$ alkyl, $C_6$-$C_8$ alkyl, $C_6$-$C_7$ alkyl, $C_7$-$C_{10}$ alkyl, $C_7$-$C_9$ alkyl, $C_7$-$C_8$ alkyl, $C_8$-$C_{10}$ alkyl, $C_8$-$C_9$ alkyl, or $C_9$-$C_{10}$ alkyl. In certain embodiments, $R^{FA2}$ is a straight chain (unbranched) alkyl group. In certain embodiments, $R^{FA2}$ is an unsubstituted alkyl group, i.e., comprising only carbon and hydrogen atoms. In certain embodiments, $R^{FA2}$ is a substituted alkyl group, e.g., substituted by halogen atoms.

In certain embodiments, $R^{FA2}$ is an optionally substituted $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl, $C_3$-$C_{10}$ alkenyl, $C_3$-$C_9$ alkenyl, $C_3$-$C_8$ alkenyl, $C_3$-$C_7$ alkenyl, $C_3$-$C_6$ alkenyl, $C_3$-$C_5$ alkenyl, $C_3$-$C_4$ alkenyl, $C_4$-$C_{10}$ alkenyl, $C_4$-$C_9$ alkenyl, $C_4$-$C_8$ alkenyl, $C_4$-$C_7$ alkenyl, $C_4$-$C_6$ alkenyl, $C_4$-$C_5$ alkenyl, $C_5$-$C_{10}$ alkenyl, $C_5$-$C_9$ alkenyl, $C_5$-$C_8$ alkenyl, $C_5$-$C_7$ alkenyl, $C_5$-$C_6$ alkenyl, $C_6$-$C_{10}$ alkenyl, $C_6$-$C_9$ alkenyl, $C_6$-$C_8$ alkenyl, $C_6$-$C_7$ alkenyl, $C_7$-$C_{10}$ alkenyl, $C_7$-$C_9$ alkenyl, $C_7$-$C_8$ alkenyl, $C_8$-$C_{10}$ alkenyl, $C_8$-$C_9$ alkenyl, or $C_9$-$C_{10}$ alkenyl. In certain embodiments, $R^{FA2}$ is a straight chain (unbranched) alkenyl group. In certain embodiments, $R^{FA2}$ is an unsubstituted alkenyl group, i.e., comprising only carbon and hydrogen atoms. In certain embodiments, $R^{FA2}$ is a substituted alkenyl group, e.g., substituted by halogen atoms. In certain embodiments, $R^{FA2}$ is a substituted alkenyl group, e.g., substituted by halogen atoms. In certain embodiments, $R^{FA2}$ is an alkenyl group comprising 1 or 2 double bonds, each independently cis or trans.

In certain embodiments, p is 2, 3, 4, 5, 6, 7, or 8. In certain embodiments, q is 1, 2, 3, 4, 5, 6, 7, or 8. In certain embodiments, p is 4, 5, 6, or 7. In certain embodiments, q is 1. In certain embodiments, q is 3, 4, or 5. In certain embodiments, q is 6, 7, or 8.

In certain embodiments, $R^{FA1}$ is selected from any one of the following saturated or unsaturated fatty acyl moieties:

Laurie —$(CH_2)_{10}CH_3$ (11 aliphatic carbons),

Myristic —$(CH_2)_{12}CH_3$ (13 aliphatic carbons),

Palmitic —$(CH_2)_{14}CH_3$ (15 aliphatic carbons),

Stearic —$(CH_2)_{16}CH_3$ (17 aliphatic carbons),

Myristoleic —$(CH_2)_7CH{=}CH(CH_2)_3CH_3$, i.e., of formula

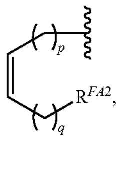

wherein p=7, q=3, $R^{FA2}$=—$CH_3$ (13 aliphatic carbons)

Palmitoleic* —$(CH_2)_7CH{=}CH(CH_2)_5CH_3$, i.e., of formula

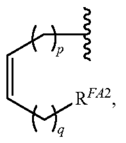

wherein p=7, q=5, $R^{FA2}$=—$CH_3$ (15 aliphatic carbons)

Sapienic* —$(CH_2)_4CH{=}CH(CH_2)_8CH_3$, i.e., of formula

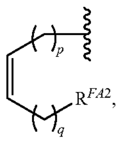

wherein p=4, q=8, $R^{FA2}$=—$CH_3$ (15 aliphatic carbons)

Oleic —$(CH_2)_7CH{=}CH(CH_2)_7CH_3$, i.e., of formula

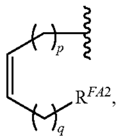

wherein p=7, q=7, $R^{FA2}$=—$CH_3$ (17 aliphatic carbons)

Linoleic* —$(CH_2)_7CH{=}CHCH_2CH{=}CH(CH_2)_4CH_3$, i.e., of formula

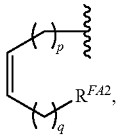

wherein p=7, q=1, $R^{FA2}$=$C_7$-alkenyl (17 aliphatic carbons)

α-Linolenic** —$(CH_2)_7CH{=}CHCH_2CH{=}CHCH_2CH{=}CHCH_2CH_3$, i.e., of formula

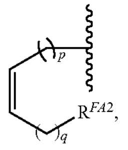

wherein p=7, q=1, $R^{FA2}$=$C_7$-alkenyl (17 aliphatic carbons)

In certain embodiments, the total number of aliphatic carbons atoms in the fatty acid is between 11 and 19, inclusive, i.e., 11, 12, 13, 14, 15, 16, 17, 18, or 19 aliphatic carbon atoms total.

In certain embodiments, the total number of aliphatic carbons in the fatty acid is selected to approximate the aliphatic chain length of the PFPRA compound (e.g., latanoprost has 13 aliphatic carbons if the cyclizing carbons 9 through 11 of the cyclopentyl ring are not counted).

For example, in certain embodiments, the PFPRA compound has between 11 and 19 total carbon atoms in the aliphatic chain of the PFPRA compound, i.e., 11, 12, 13, 14, 15, 16, 17, 18, or 19 aliphatic carbon atoms total.

In some embodiments, fatty acid is selected such that its predicted length (e.g., by molecular modeling) is similar (e.g., within ±3 Å) to the predicted length of the PFPRA compound. For example, oleic acid has a predicted length (between the two most distant heavy atoms) of about 19 Å, which compares favorably with a length of about 17 Å for latanoprost free acid, tafluprost free acid, and bimatoprost free acid; 18 Å for latanoprost and tafluprost; about 19 Å for bimatoprost and travoprost free acid (i.e., fluprostenol), and about 20 Å for travoprost. In some embodiments, the predicted length is in an energy-minimized conformation. In some embodiments, the predicted length is of a conformation whereby freely rotating bonds are rotated as to provide a maximal length.

In some embodiments, the composition further comprises one or more organic alcohols, e.g., ethanol, propylene glycol, methanol, propanol, isopropanol, 1,3-butanediol, or ethylene glycol. In certain embodiments, the organic alcohol is propylene glycol and/or ethanol. However, in certain embodiments, 1,3,-butanediol is excluded.

PFPRA Compounds

As used herein, a "PFPRA compound" can be any therapeutically relevant, naturally occurring or synthetic prostaglandin or prostaglandin analog, provided that it or its active metabolite (e.g., if an ester, the parent acid) suitably agonizes a prostaglandin FP receptor in a suitable functional assay. As used herein, a suitable degree of agonism can be defined, for example, as a half maximal effective concentration ($EC_{50}$) of 1 micromolar or less, preferably 100 nanomolar or less. A suitable functional assay can be, for example, assessment of phosphoinositide turnover in HEK293 cells expressing a cloned FP prostaglandin receptor. See, e.g., Sharif et al., *J. Ocular Pharmacol. Ther.* 2002; 18:313-324. Many PFPRA compounds can be classified as pro staglandins, prostanoids, or prostamides. Naturally occurring prostaglandins are a class of structurally related eicosanoid hormones that are derived enzymatically from arachidonic acid. An example of a naturally occurring prostaglandin PFPRA compound is prostaglandin F2α. Exemplary synthetic prostaglandins, which are prostaglandin F2α analogs, include, but are not limited to, latanoprost, latanoprost free acid, bimatoprost, bimatoprost free acid, tafluprost, tafluprost free acid, travoprost, travoprost free acid (a.k.a. fluprostenol), and prodrugs (e.g., 9-, 11-, and/or 15-ester derivatives) thereof.

In certain embodiments, the PFPRA compound is a compound of Formula (I) or (II):

(I)

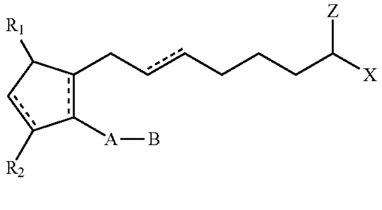

-continued (II)

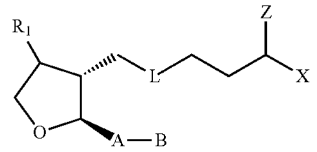

or a pharmaceutically acceptable salt, hydrate, solvate, stereoisomer, polymorph, tautomer, isotopically enriched derivative, or prodrug thereof;

wherein:

L is a group of the formula

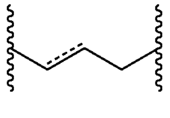 or 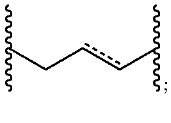;

each instance of  independently represents a single bond or a double bond which can be in the cis or trans configuration;

A is optionally substituted $C_{1-10}$alkylene, optionally substituted $C_{2-10}$alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl;

X is $—OR_4$, $—SR_4$, or $—N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, $—C(=O)R_5$, or $—C(=O)OR_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring;

Z is =O, =S, or $=NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms;

with regard to the compound of Formula (I), one of $R_1$ and $R_2$ is =O, —OH, or a $—O(CO)R_6$ group and the other one is —OH or $—O(CO)R_6$, or $R_1$ is =O and $R_2$ is H, wherein $R_6$ is an optionally substituted $C_{1-20}$alkyl, optionally substituted $C_{2-20}$alkenyl, optionally substituted $C_{7-20}$ alkynyl, or $—(CH_2)_mR_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl; and with regard to the compound of Formula (II), $R_1$ is =O, —OH, or $—O(CO)R_6$, wherein $R_6$ is a an optionally substituted $C_{1-20}$alkyl, optionally substituted $C_{2-20}$alkenyl, optionally substituted $C_{2-20}$ alkynyl, or $—(CH_2)_mR_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

In certain embodiments, the endocyclic dotted lines of Formula (I) (i.e., depicted in the 5-membered ring) each represent a single bond.

For example, in certain embodiments, wherein the endocyclic dotted lines of Formula (I) each represent a single bond, provided is a compound having any one of the following stereochemistry:

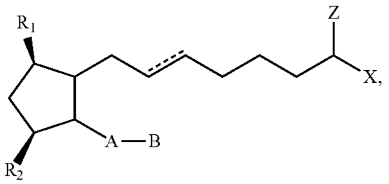

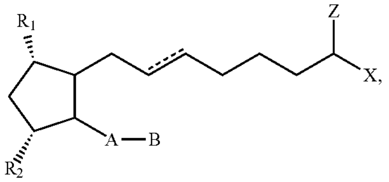

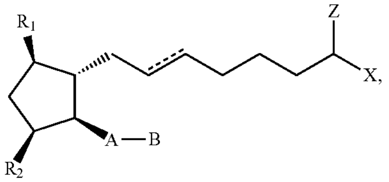

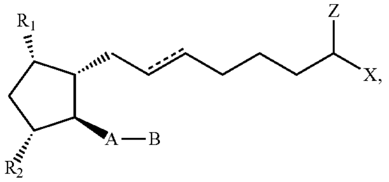

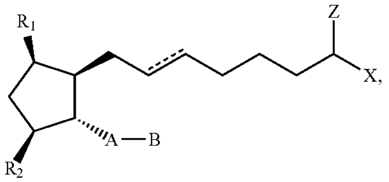

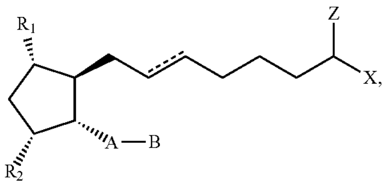

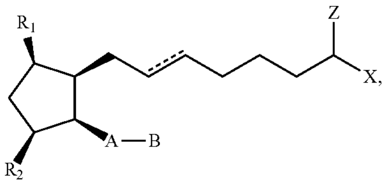

-continued

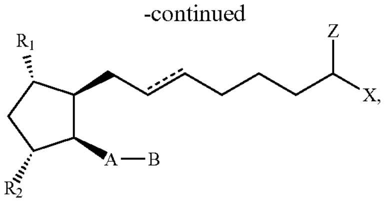

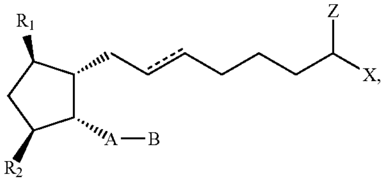

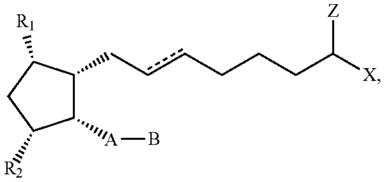

pharmaceutically acceptable salt, hydrate, solvate, stereoisomer, polymorph, tautomer, isotopically enriched derivative, or prodrug thereof, wherein - - - - - - , $R_1$, $R_2$, A, B, Z and X are as defined herein.

In certain embodiments, the exocyclic dotted line - - - - - - (i.e., depicted outside of the 5-membered ring) of Formula (I) or (II) or a subset thereof represents a double bond in the cis or trans configuration. In certain embodiments, the exocyclic dotted line - - - - - - represents a double bond in the cis configuration.

In certain embodiments, each instance of - - - - - - independently represents a single bond or a double bond which can be in the cis or trans configuration.

As generally defined above, one of $R_1$ and $R_2$ is =O, —OH, or a —O(CO)$R_6$ group and the other one is —OH or —O(CO)$R_6$, or $R_1$ is =O and $R_2$ is H, wherein $R_6$ is an optionally substituted $C_{1-20}$alkyl, optionally substituted $C_{2-20}$alkenyl, optionally substituted $C_{2-20}$ alkynyl, or —$(CH_2)_mR_7$ wherein m is 0 or an integer of between 1-10, inclusive- and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

In certain embodiments, $R_1$ is =O and $R_2$ is H.

In certain embodiments, one of $R_1$ and $R_2$ is —OH, substituted hydroxyl, or —O(CO)$R_6$, and the other one is —OH, substituted hydroxyl, or —O(CO)$R_6$.

In certain embodiments, both $R_1$ and $R_2$ are —OH.

In certain embodiments, one of $R_1$ and $R_2$ is —OH, and the other one is —O(CO)$R_6$. In certain embodiments, $R_1$ is —OH, and $R_2$ is —O(CO)$R_6$. In certain embodiments, $R_2$ is —OH, and $R_1$ is —O(CO)$R_6$. In certain embodiments, $R_6$ is an optionally substituted $C_{1-20}$alkyl, e.g., optionally substituted $C_{1-15}$alkyl, optionally substituted $C_{1-10}$alkyl, optionally substituted $C_{1-8}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_6$ is —$(CH_2)_r$-$CH_3$ wherein r is 0, 1, 2, 3, 4, 5, or 6, —$CH(CH_3)_2$, —$CH_2CH(CH_3)_2$, —$CH_2C(CH_3)_3$, or —$C(CH_3)_3$.

As generally defined above, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one or more —O— or —S— groups.

In certain embodiments, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one —O— group.

In certain embodiments, A is optionally substituted $C_{4-6}$alkylene, optionally substituted $C_{4-6}$alkenylene or optionally substituted $C_{4-6}$alkynylene, wherein the alkylene, alkenylene, or alkynylene group is optionally interrupted by one —O— group.

In certain embodiments, A is optionally substituted $C_{4-6}$alkylene optionally interrupted by one —O— group. In certain embodiments, A is optionally substituted $C_4$-6alkenylene optionally interrupted by one —O— group. In certain embodiments, A is optionally substituted $C_{4-6}$alkynylene optionally interrupted by one —O— group.

In certain embodiments, A is substituted with one or more groups selected from the group consisting of halogen, —OH, substituted hydroxyl, or —O(CO)$R_5$, wherein $R_8$ is optionally substituted $C_{1-20}$alkyl, optionally substituted $C_{2-20}$alkenyl, optionally substituted $C_{2-20}$alkynyl, or —$(CH_2)_mR_9$ wherein m is 0 or an integer between 1-10, inclusive, and $R_9$ is optionally substituted $C_{3-7}$carbocyclyl, optionally substituted $C_{6-10}$aryl, and optionally substituted 5-14-membered-heteroaryl.

In certain embodiments, A is substituted with =O.

In certain embodiments, A is substituted with —OC(=O)$R_5$, wherein $R_8$ is optionally substituted $C_{1-20}$alkyl, optionally substituted $C_{2-20}$alkenyl, optionally substituted $C_{2-20}$alkynyl, or —$(CH_2)_mR_9$, wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl.

In certain embodiments, A is substituted with —OH or substituted hydroxyl.

In certain embodiments, A is substituted with substituted hydroxyl.

In certain embodiments, A is substituted with —OH.

In certain embodiments, A is a group of the Formula (i), (ii), (iii), (iv), (v), or (vi):

(i)

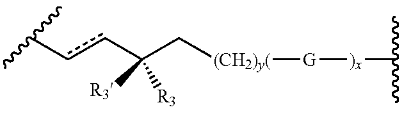

(ii)

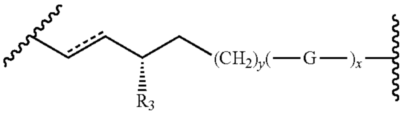

(iii)

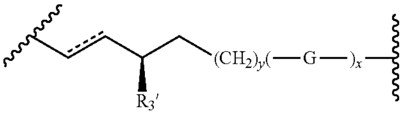

(iv)

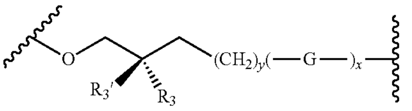

-continued (v)

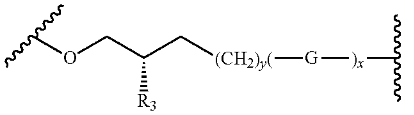

(vi)

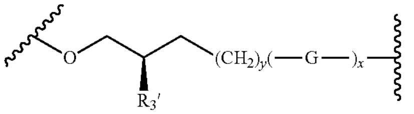

wherein each instance of ------ independently represents a single bond or a double bond which can be in the cis or trans configuration;

each instance of $R_3$ and $R_3$' is hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —$(CH_2)_mR_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3$' are joined to form =O;

G is —O— or —S—;

y is 0, 1, or 2; and x is 0 or 1.

In certain embodiments, G is —O—. In certain embodiments, G is —S—.

In certain embodiments, ------ of Formula (i), (ii), or (iii) represents a double bond in the cis configuration.

In certain embodiments, ------ of Formula (i), (ii), or (iii) represents a double bond in the trans configuration.

In certain embodiments, the group of the Formula (i) is of the formula:

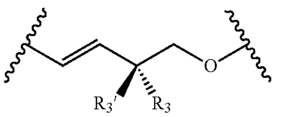

or

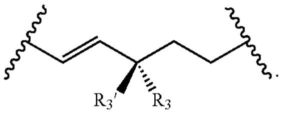

.

In certain embodiments, the group of the Formula (ii) is of the formula:

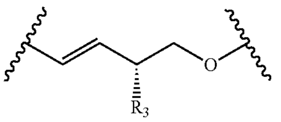

or

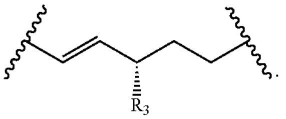

.

In certain embodiments, ------ of Formula (i), (ii), or (iii) represents a single bond.

In certain embodiments, the group of the Formula (i) is of the formula:

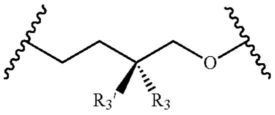 or

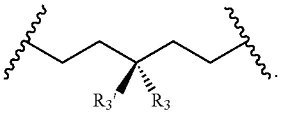.

In certain embodiments, the group of the Formula (ii) is of the formula:

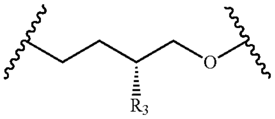 or

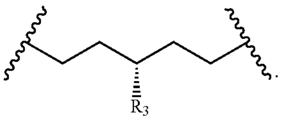.

As generally defined above, each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —$(CH_2)_m R_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl; or $R_3$ and $R_3'$ are joined to form ═O.

In certain embodiments, $R_3$ is hydrogen. In certain embodiments, $R_3'$ is hydrogen. In certain embodiments, $R_3$ is hydrogen and $R_3'$ is a non-hydrogen group. In certain embodiments, $R_3'$ is hydrogen and $R_3$ is a non-hydrogen group. In certain embodiments, however, neither $R_3$ nor $R_3'$ is hydrogen.

In certain embodiments, $R_3$ and $R_3'$ are joined to form ═O.

In certain embodiments, $R_3$ and $R_3'$ are the same group. In certain embodiments, $R_3$ and $R_3'$ are different groups.

In certain embodiments, $R_3$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —$(CH_2)_m R_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3$ is —O(CO)$R_8$. In certain embodiments, $R_3$ is —O(CO)$R_8$, and $R_8$ is optionally substituted $C_{1-20}$alkyl, e.g., optionally substituted $C_{1-15}$alkyl, optionally substituted $C_{1-10}$alkyl, optionally substituted $C_{1-8}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_3$ is —O(CO)$R_8$, and $R_8$ is —$(CH_2)_q CH_3$ wherein q is 0,1, 2, 3, 4, 5, or 6, —$CH(CH_3)_2$, —$CH_2CH(CH_3)_2$, —$CH_2C(CH_3)_3$, or —$C(CH_3)_3$. In certain embodiments, $R_3$ is —OH or substituted hydroxyl. In certain embodiments, $R_3$ is substituted hydroxyl. In certain embodiments, $R_3$ is —OH.

In certain embodiments, $R_3'$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —$(CH_2)_m R_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3'$ is —O(CO)$R_8$. In certain embodiments, $R_3'$ is —O(CO)$R_8$, and $R_8$ is optionally substituted $C_{1-20}$alkyl, e.g., optionally substituted $C_{1-15}$alkyl, optionally substituted $C_{1-10}$alkyl, optionally substituted $C_{1-5}$alkyl, optionally substituted $C_{1-6}$alkyl, optionally substituted $C_{1-5}$alkyl, optionally substituted $C_{1-4}$alkyl, optionally substituted $C_{1-3}$ alkyl, or optionally substituted $C_{1-2}$alkyl. In certain embodiments, $R_3'$ is —O(CO)$R_8$, and $R_8$ is —$(CH_2)_q CH_3$ wherein q is 0, 1, 2, 3, 4, 5, or 6, —$CH(CH_3)_2$, —$CH_2CH(CH_3)_2$, —$CH_2C(CH_3)_3$, or —$C(CH_3)_3$. In certain embodiments, $R_3'$ is —OH or substituted hydroxyl. In certain embodiments, $R_3'$ is substituted hydroxyl. In certain embodiments, $R_3'$ is —OH.

In certain embodiments, $R_3$ is halogen, e.g., selected from fluoro, chloro, bromo, and iodo. In certain embodiments, $R_3'$ is halogen, e.g., selected from fluoro, chloro, bromo, and iodo. In certain embodiments, $R_3$ is halogen and $R_3'$ is halogen, e.g., each independently selected from fluoro, chloro, bromo, and iodo. In certain embodiments, both $R_3$ and $R_3'$ are fluoro.

In certain embodiments, y is 0; and x is 1. In certain embodiments, y is 0; and x is 0. In certain embodiments, y is 1; and x is 1. In certain embodiments, y is 1; and x is 0. In certain embodiments, y is 2; and x is 0. In certain embodiments, y is 2; and x is 1.

As defined generally above, B is hydrogen, optionally substituted $C_3$-7carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl.

In certain embodiments, B is hydrogen.

In certain embodiments, B is optionally substituted $C_{1-30}$alkyl. In certain embodiments, B is optionally substituted $C_{2-30}$alkenyl. In certain embodiments, B is optionally substituted $C_{2-30}$alkynyl.

In certain embodiments, B is optionally substituted $C_{3-7}$carbocyclyl, e.g., optionally substituted cyclohexyl. In certain embodiments, B is optionally substituted 3-8-membered-heterocyclyl. In certain embodiments, B is optionally substituted 5-14-membered-heteroaryl. In certain embodiments, B is optionally substituted $C_{6-10}$aryl. In certain embodiments, B is optionally substituted $C_6$aryl (i.e., phenyl). In certain embodiments, B is optionally substituted $C_{10}$aryl (i.e., napthyl).

For example, in certain embodiments, B is an optionally substituted phenyl of the Formula (viii):

(viii)

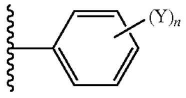

wherein:

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino; and n is 0 or an integer of from 1 to 5, inclusive.

In certain embodiments, n is 0 or an integer from 1 to 3, inclusive. In certain embodiments, n is 0 or an integer from 1 to 2, inclusive. In certain embodiments, n is 0. In certain embodiments, n is 1. In certain embodiments, n is 2. In certain embodiments, n is 3.

For example, in certain embodiments, wherein n is 1, the group of the Formula (viii) is of the formula:

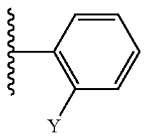
,
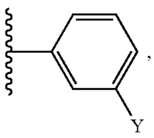
, or
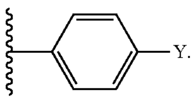

In certain embodiments, wherein n is 2, the group of the Formula (viii) is of the formula:

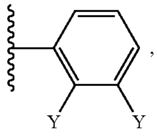
,
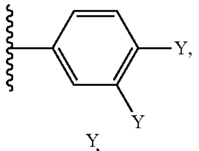

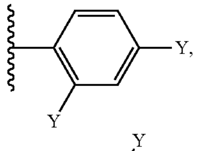

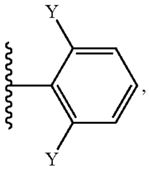
, or

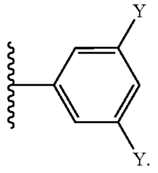

In certain embodiments, Y is halo, i.e. selected from fluoro, iodo, bromo, or chloro. In certain embodiments Y is chloro. In certain embodiments Y is fluoro.

In certain embodiments, Y is optionally substituted $C_{1-10}$alkyl or $C_{1-10}$perhaloalkyl.

In certain embodiments, Y is optionally substituted $C_{1-10}$alkyl. In certain embodiments, Y is optionally substituted $C_{1-6}$alkyl. In certain embodiments, Y is optionally substituted $C_{1-4}$alkyl. In certain embodiments, Y is optionally substituted $C_{1-3}$alkyl. In certain embodiments, Y is optionally substituted $C_{1-2}$alkyl. In certain embodiments, Y is —$CH_3$, —$CH_2F$, or —$CHF_2$.

In certain embodiments, Y is $C_{1-10}$perhaloalkyl. In certain embodiments, Y is $C_{1-6}$perhaloalkyl. In certain embodiments, Y is $C_{1-4}$perhaloalkyl. In certain embodiments, Y is $C_{1-3}$perhaloalkyl. In certain embodiments, Y is $C_{1-2}$erhaloalkyl. In certain embodiments, Y is —$CF_3$, —$CF_2C_1$, or —$CFCl_2$.

As generally defined above, Z is ═O, ═S, or ═$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms.

In certain embodiments, Z is ═O.

In certain embodiments, Z is ═S.

In certain embodiments, Z is ═$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl. In certain embodiments, Z is ═$NR_Z$ and $R_Z$ is hydrogen.

In certain embodiments, Z represents two hydrogen atoms.

As generally defined above, X is —$OR_4$, —$SR_4$, or —$N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, —C(═O)$R_5$, or —C(═O)$OR_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring.

In certain embodiments, X is —$OR_4$. In certain embodiments, X is —$OR_4$, and $R_4$ is hydrogen. In certain embodiments, X is —$OR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$OR_4$, wherein $R_4$ is —C(═O)$R_5$, or —C(═O)$OR_5$.

In certain embodiments, X is —$OR_4$, and $R_4$ is —C(═O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$OR_4$, and $R_4$ is —C(═O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$. In certain embodiments, X is —$SR_4$, and $R_4$ is hydrogen. In certain embodiments, X is —$SR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, wherein $R_4$ is —C(=O)$R_5$, or —C(=O)$OR_5$.

In certain embodiments, X is —$SR_4$, and $R_4$ is —C(=O)$R_5$, and $R_5$ is optionally substituted $C_{1-10}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_4$-6alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, and $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$N(R_4)_2$. In certain embodiments, X is —$N(R_4)_2$ and at least one $R_4$ group is hydrogen. In certain embodiments, X is —$N(R_4)_2$ and neither of the two $R_4$ groups are hydrogen. In certain embodiments, X is —$N(R_4)_2$ and at least one $R_4$ is optionally substituted $C_{1-20}$alkyl, optionally substituted $C_{2-20}$alkenyl, or optionally substituted $C_{2-20}$alkynyl. In certain embodiments, X is —$N(R_4)_2$ and at least one $R_4$ is optionally substituted $C_{1-10}$alkyl, optionally substituted $C_{2-10}$alkenyl, or optionally substituted $C_{2-10}$alkynyl. In certain embodiments, X is —$N(R_4)_2$ and at least one $R_4$ is optionally substituted $C_{1-6}$alkyl, e.g., $C_{1-3}$alkyl, $C_{3-4}$alkyl, or $C_{4-6}$alkyl In certain embodiments, X is —$N(R_4)_2$ and at least one $R_4$ is optionally substituted $C_{2-6}$alkenyl, e.g., $C_{2-3}$alkenyl, $C_{3-4}$alkenyl, or $C_{4-6}$alkenyl. In certain embodiments, X is —$N(R_4)_2$ and at least one $R_4$ is optionally substituted $C_{2-6}$alkynyl, e.g., $C_{2-3}$alkynyl, $C_{3-4}$alkynyl, or $C_{4-6}$alkynyl. However, in certain embodiments, X is not —NH(iPr).

In certain embodiments, X is —$N(R_4)_2$ and at least one $R_4$ is —C(=O)$R_5$, or —C(=O)$OR_5$.

In certain embodiments, X is —$N(R_4)_2$ and at least one $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_3$-4alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$N(R_4)_2$ and at least one $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In other embodiments, X is —$N(R_4)_2$ and the two $R_4$ groups are joined to form an optionally substituted 3-8-membered-heterocyclyl or optionally substituted 5-14-membered-heteroaryl ring.

In certain embodiments, wherein X is —$OR_4$, —$SR_4$, or —$N(R_4)_2$, any one of $R_4$ or $R_5$ is optionally substituted $C_{1-30}$alkyl (e.g., $C_{1-10}$alkyl, $C_{1-6}$alkyl, $C_{1-3}$alkyl, $C_{7-30}$alkyl, $C_{10-30}$alkyl, $C_{7-25}$alkyl, $C_{10-25}$alkyl, $C_{15-25}$alkyl). In certain embodiments, any one of $R_4$ or $R_5$ is optionally substituted $C_{2-30}$alkenyl (e.g., $C_{2-10}$alkenyl, $C_{2-6}$alkenyl, $C_{1-3}$alkenyl, $C_{7-30}$alkenyl, $C_{10-30}$alkenyl, $C_{7-25}$alkenyl, $C_{10-25}$alkenyl, $C_{15-25}$ alkenyl). In certain embodiments, any one of $R_4$ or $R_5$ is optionally substituted $C_{2-30}$alkynyl (e.g., $C_{2-10}$alkynyl, $C_{2-6}$alkynyl, $C_{1-30}$alkynyl, $C_{7-30}$alkynyl, $C_{10-30}$alkynyl, $C_{7-25}$alkynyl, $C_{10-25}$alkynyl, $C_{15-25}$alkynyl).

In any of the above embodiments, when $R_4$ or $R_5$ are defined as a $C_{7-30}$alkyl or $C_{7-30}$alkenyl groups, such groups may also be referred to as "lipid tails." Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$ alkyl or $C_{13-22}$ alkenyl), or very long (i.e., with tails greater than 22 carbons, e.g., $C_{23-30}$ alkyl or $C_{23-30}$ alkenyl).

Exemplary unsaturated lipid tails include, but are not limited to:

Myristoleic —$(CH_2)_7CH{=}CH(CH_2)_3CH_3$,

Palmitoliec —$(CH_2)_7CH{=}CH(CH_2)_5CH_3$,

Sapienic —$(CH_2)_4CH{=}CH(CH_2)_8CH_3$,

Oleic —$(CH_2)_7CH{=}CH(CH_2)_7CH_3$,

Linoleic —$(CH_2)_7CH{=}CHCH_2CH{=}CH(CH_2)_4CH_3$,

α-Linolenic —$(CH_2)_7CH{=}CHCH_2CH{=}CHCH_2CH{=}CHCH_2CH_3$,

Arachinodonic —$(CH_2)_3CH{=}CHCH_2CH{=}CHCH_2CH{=}CHCH_2CH{=}CH(CH_2)_4CH_3$,

Eicosapentaenoic —$(CH_2)_3CH{=}CHCH_2CH{=}CHCH_2CH{=}CHCH_2CH{=}CHCH_2CH{=}CHCH_2CH_3$, Erucic —$(CH_2)_{11}CH{=}CH(CH_2)_7CH_3$, and Docosahexaenoic —$(CH_2)_2CH{=}CHCH_2CH{=}CHCH_2CH{=}CHCH_2CH{=}CHCH_2CH{=}CHCH_2CH{=}CH$—$CH_2CH_3$.

Exemplary saturated lipid tails include, but are not limited to:

Laurie —$(CH_2)_{10}CH_3$,

Myristic —$(CH_2)_{12}CH_3$,

Palmitic —$(CH_2)_{14}CH_3$,

Stearic —$(CH_2)_{16}CH_3$,

Arachidic —$(CH_2)_{18}CH_3$,

Behenic —$(CH_2)_{20}CH_3$,

Lignoceric —$(CH_2)_{22}CH_3$, and

Cerotic —$(CH_2)_{24}CH_3$.

In certain embodiments of Formula (I), the compound is of Formula (I-a):

(I-a)

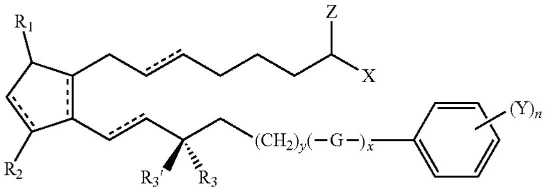

or a pharmaceutically acceptable salt, hydrate, solvate, stereoisomer, polymorph, tautomer, isotopically enriched derivative, or prodrug thereof; wherein $R_1$, $R_2$, Z, and X are as defined herein;

each instance of ------ independently represents a single bond or a double bond which can be in the cis or trans configuration;

each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —$(CH_2)_mR_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3'$ are joined to form =O;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino;

G is —O— or —S—;

y is 0, 1, or 2;

x is 0 or 1; and n is 0 or an integer of from 1 to 5, inclusive.

In certain embodiments of Formula (I-a), wherein $R_3'$ is hydrogen, the compound is of Formula (I-b):

(I-b)

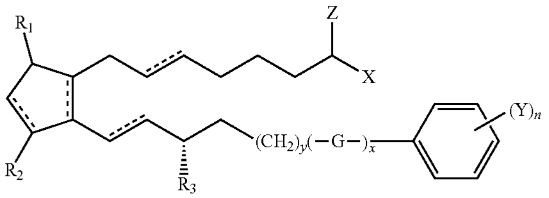

or a pharmaceutically acceptable salt, hydrate, solvate, stereoisomer, polymorph, tautomer, isotopically enriched derivative, or prodrug thereof; wherein ------ , $R_1$, $R_2$, $R_3$, Z, X, Y, G, y, x, and n are as defined herein.

In certain embodiments of Formula (I-a), wherein $R_3$ is hydrogen, the compound is of Formula (I-c):

(I-c)

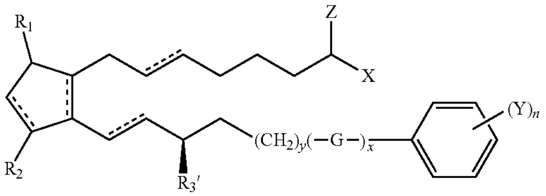

or a pharmaceutically acceptable salt, hydrate, solvate, stereoisomer, polymorph, tautomer, isotopically enriched derivative, or prodrug thereof; wherein ------ , $R_1$, $R_2$, $R_3'$, Z, X, Y, G, y, x, and n are as defined herein.

In certain embodiments, G is —O—. In certain embodiments, G is —S—.

In certain embodiments of Formula (I-a), wherein G is —O—, provided is a compound of Formula (I-a1):

(I-a1)

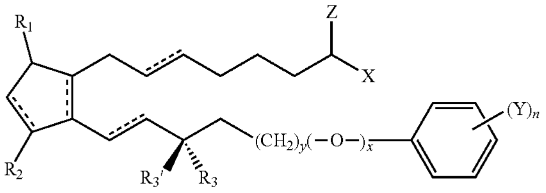

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ------ , $R_1$, $R_2$, $R_3$, Z, X, Y, y, x, and n are as defined herein.

In certain embodiments of Formula (I-b), wherein G is —O—, the compound is of Formula (I-b1):

(I-b1)

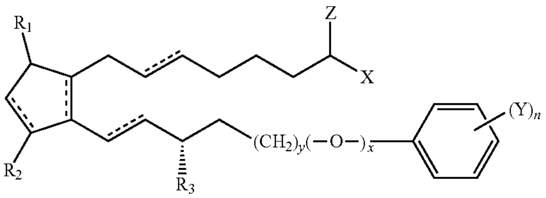

or a pharmaceutically acceptable salt, hydrate, solvate, stereoisomer, polymorph, tautomer, isotopically enriched derivative, or prodrug thereof; wherein ------ , $R_1$, $R_2$, $R_3$, Z, X, Y, y, x, and n are as defined herein.

In certain embodiments of Formula (I-c), wherein G is —O—, the compound is of Formula (I-c1):

(I-c1)

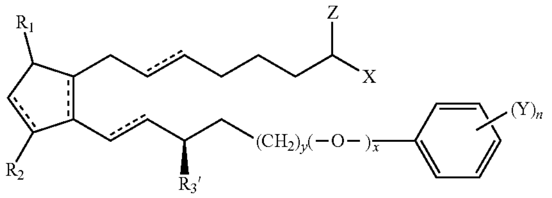

or a pharmaceutically acceptable salt, hydrate, solvate, stereoisomer, polymorph, tautomer, isotopically enriched derivative, or prodrug thereof; wherein ====== , $R_1$, $R_2$, $R_3'$, Z, X, Y, y, x, and n are as defined herein.

In certain embodiments of Formula (I-a), wherein G is —S—, provided is a compound of Formula (I-a2):

(I-a2)

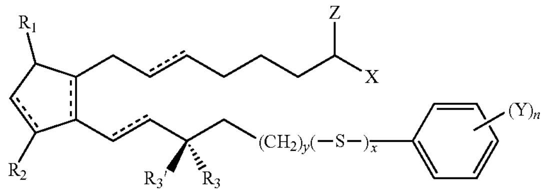

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ====== , $R_1$, $R_2$, $R_3$, $R_3'$, Z, X, Y, y, x, and n are as defined herein.

In certain embodiments of Formula (I-b), wherein G is —S—, the compound is of Formula (I-b2):

(I-b2)

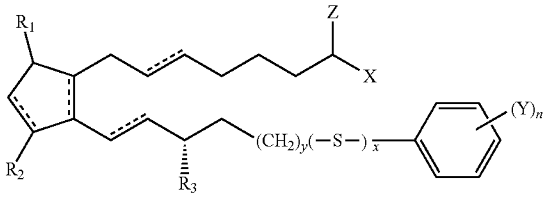

or a pharmaceutically acceptable salt, hydrate, solvate, stereoisomer, polymorph, tautomer, isotopically enriched derivative, or prodrug thereof; wherein ====== , $R_1$, $R_2$, $R_3$, Z, X, Y, y, x, and n are as defined herein.

In certain embodiments of Formula (I-c), wherein G is —S—, the compound is of Formula (I-c2):

(I-c2)

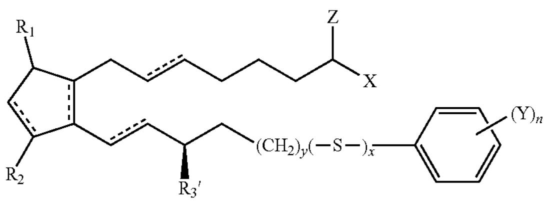

or a pharmaceutically acceptable salt, hydrate, solvate, stereoisomer, polymorph, tautomer, isotopically enriched derivative, or prodrug thereof; wherein ====== , $R_1$, $R_2$, $R_3'$, Z, X, Y, y, x, and n are as defined herein.

In certain embodiments, the compound of Formula (I-a) has the following stereochemistry, also referred to herein as a compound of Formula (I-d):

(I-d)

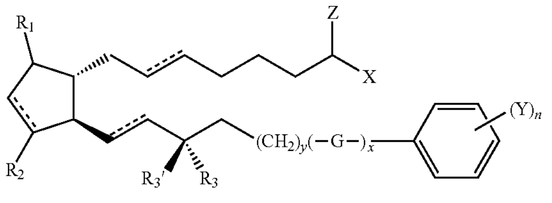

or a pharmaceutically acceptable salt, hydrate, solvate, stereoisomer, polymorph, tautomer, isotopically enriched derivative, or prodrug thereof; wherein ====== , $R_1$, $R_2$, $R_3$, $R_3'$, Z, Y, G, X, y, x, and n are as defined herein.

In certain embodiments of Formula (I-d), wherein $R_3'$ is hydrogen, the compound is of Formula (I-e):

(I-e)

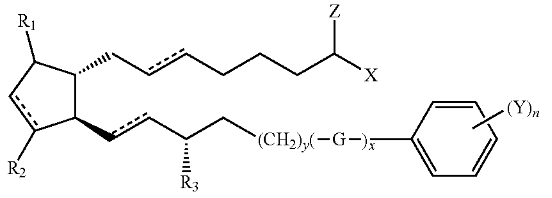

or a pharmaceutically acceptable salt, hydrate, solvate, stereoisomer, polymorph, tautomer, isotopically enriched derivative, or prodrug thereof; wherein ====== , $R_1$, $R_2$, $R_3$, Z, X, Y, G, y, x, and n are as defined herein.

In certain embodiments of Formula (I-d), wherein $R_3$ is hydrogen, the compound is of Formula (I-f):

(I-f)

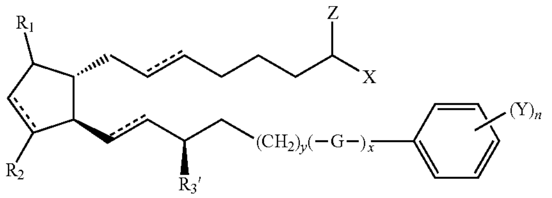

or a pharmaceutically acceptable salt, hydrate, solvate, stereoisomer, polymorph, tautomer, isotopically enriched derivative, or prodrug thereof; wherein ====== , $R_1$, $R_2$, $R_3'$ Z, X, Y, G, y, x, and n are as defined herein.

In certain embodiments, G is —O—. In certain embodiments, G is —S—.

In certain embodiments of Formula (I-d), wherein G is —O—, the compound is of Formula (I-411):

(I-d1)

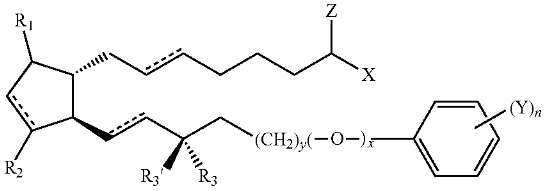

or a pharmaceutically acceptable salt, hydrate, solvate, stereoisomer, polymorph, tautomer, isotopically enriched derivative, or prodrug thereof; wherein ------ , $R_1$, $R_2$, $R_3$, $R_3'$, Z, Y, X, y, x, and n are as defined herein.

In certain embodiments of Formula (I-e), wherein G is —O—, the compound is of Formula (I-e1):

(I-e1)

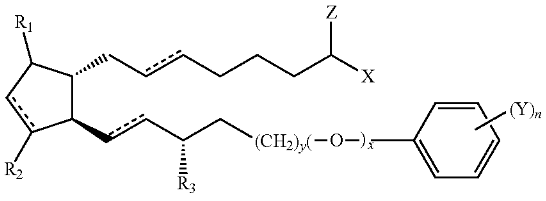

or a pharmaceutically acceptable salt, hydrate, solvate, stereoisomer, polymorph, tautomer, isotopically enriched derivative, or prodrug thereof; wherein ------ , $R_1$, $R_2$, $R_3$, Z, X, Y, y, x, and n are as defined herein.

In certain embodiments of Formula (I-f), wherein G is —O—, the compound is of Formula (I-f1):

(I-f1)

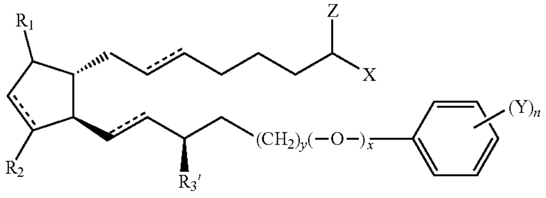

or a pharmaceutically acceptable salt, hydrate, solvate, stereoisomer, polymorph, tautomer, isotopically enriched derivative, or prodrug thereof; wherein ------ , $R_1$, $R_2$, $R_3^1$, Z, X, Y, y, x, and n are as defined herein.

In certain embodiments of Formula (I-d), wherein G is —S—, the compound is of Formula (I-d2):

(I-d2)

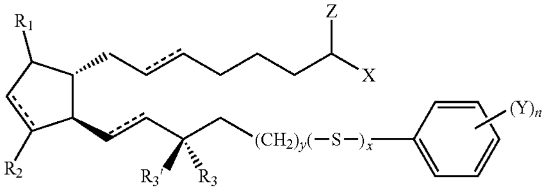

or a pharmaceutically acceptable salt, hydrate, solvate, stereoisomer, polymorph, tautomer, isotopically enriched derivative, or prodrug thereof; wherein ------ , $R_1$, $R_2$, $R_3$, $R_3'$, Z, Y, X, y, x, and n are as defined herein.

In certain embodiments of Formula (I-e), wherein G is —S—, the compound is of Formula (I-e2):

(I-e2)

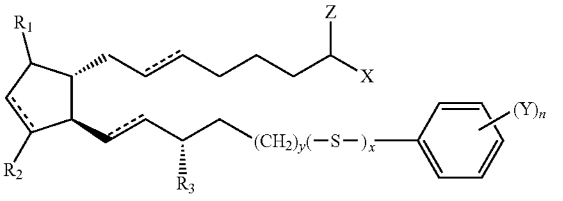

or a pharmaceutically acceptable salt, hydrate, solvate, stereoisomer, polymorph, tautomer, isotopically enriched derivative, or prodrug thereof; wherein ------ , $R_1$, $R_2$, $R_3$, Z, X, Y, y, x, and n are as defined herein.

In certain embodiments of Formula (I-f), wherein G is —S—, the compound is of Formula (I-f2):

(I-f2)

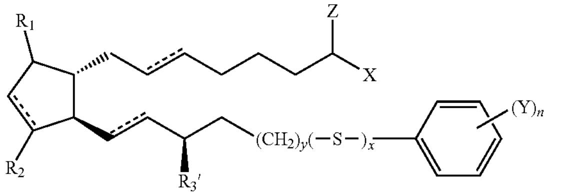

or a pharmaceutically acceptable salt, hydrate, solvate, stereoisomer, polymorph, tautomer, isotopically enriched derivative, or prodrug thereof; wherein ------ , $R_1$, $R_2$, $R_3'$, Z, X, Y, y, x, and n are as defined herein.

In certain embodiments, Z is =O. In certain embodiments, each represents a single bond. In certain embodiments, each endocyclic represents a single bond. In certain embodiments at least one exocyclic ------ represents a cis-double bond. In certain embodiments, each instance of $R_1$ and $R_2$ is —OH. In certain embodiments, each instance of $R_1$ and $R_2$ is —O(CO)$R_6$. In certain embodiments, one of $R_1$ and $R_2$ is —OH, and the other one is —O(CO)$R_6$. In certain embodiments, one of $R_3$ and $R_3'$ is —O(CO)$R_8$, and the other is hydrogen. In certain embodiments, $R_1$ is —OH, $R_2$ is —O(CO)$R_6$, one of $R_3$ and $R_3'$ is —OH, and the other is hydrogen. In certain embodiments, $R_2$ is —OH, $R_1$ is —O(CO)$R_6$, one of $R_3$ and $R_3'$ is —OH, and the other is hydrogen. In certain embodiments, each of $R_1$ and $R_2$ is —OH, and one of $R_3$ and $R_3'$ is —O(CO)$R_8$, and the other is hydrogen. In certain embodiments, each instance of $R_1$ and $R_2$ is —O(CO)$R_6$, and one of $R_3$ and $R_3'$ is —O(CO)$R_8$, and the other is hydrogen. In certain embodiments, —O(CO)$R_6$ and —O(CO)$R_8$ attached to the compound are the same group. In certain embodiments, —O(CO)$R_6$ and —O(CO)$R_8$ attached to the compound are different groups.

In certain embodiments of Formula (I-d), wherein Z is =O, each endocyclic ------ represents a single bond, and at least one exocyclic ------ represents a cis-double bond, provided is a compound of Formula (I-d3) having the following stereochemistry:

(I-d3)

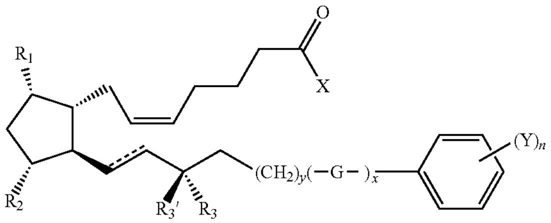

or a pharmaceutically acceptable salt, hydrate, solvate, stereoisomer, polymorph, tautomer, isotopically enriched derivative, or prodrug thereof; wherein ------ , $R_1$, $R_2$, $R_3$, $R_3$', G, Y, X, y, x, and n are as defined herein.

In certain embodiments of Formula (I-e), wherein Z is =O, each endocyclic ------ represents a single bond, and at least one exocyclic ------ represents a cis-double bond, provided is a compound of Formula (I-e3) having the following stereochemistry:

(I-e3)

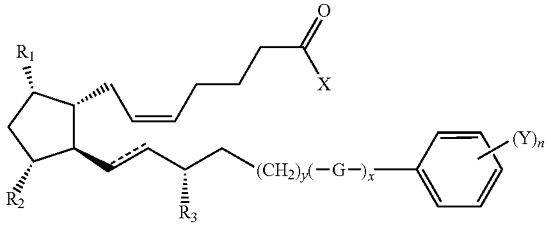

or a pharmaceutically acceptable salt, hydrate, solvate, stereoisomer, polymorph, tautomer, isotopically enriched derivative, or prodrug thereof; wherein ------ , $R_1$, $R_2$, $R_3$, G, X, Y, y, x, and n are as defined herein.

In certain embodiments of Formula (I-f), wherein Z is =O, each endocyclic ------ represents a single bond, and at least one exocyclic ------ represents a cis-double bond, provided is a compound of Formula (I-f3) having the following stereochemistry:

(I-f3)

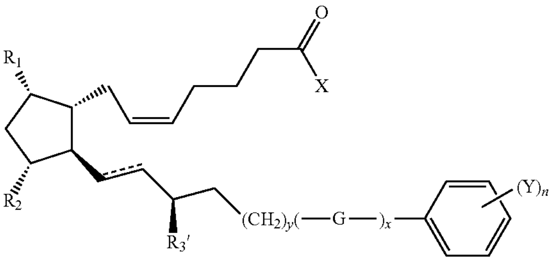

or a pharmaceutically acceptable salt, hydrate, solvate, stereoisomer, polymorph, tautomer, isotopically enriched derivative, or prodrug thereof; wherein ------ , $R_1$, $R_2$, $R_3$', G, X, Y, y, x, and n are as defined herein.

In certain embodiments of Formula (I-d3), wherein $R_1$ is —OH and $R_2$ is —O(CO)$R_6$, or wherein $R_2$ is —OH and $R_1$ is —O(CO)$R_6$, or wherein both $R_1$ and $R_2$ are —O(CO)$R_6$, provided is a compound of Formula (I-d4), (I-d5), and (I-d6) having the following stereochemistry:

(I-d4)

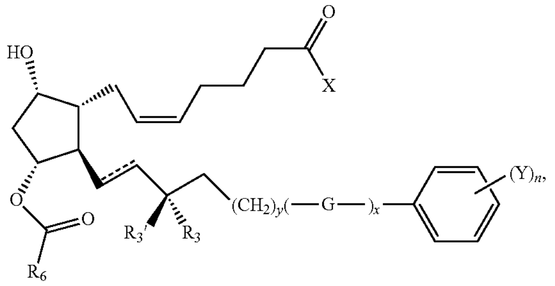

(I-d5)

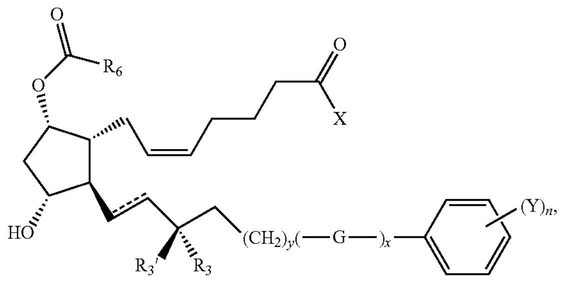

(I-d6)

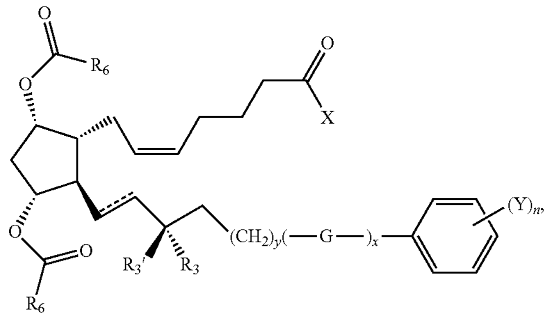

or a pharmaceutically acceptable salt, hydrate, solvate, stereoisomer, polymorph, tautomer, isotopically enriched derivative, or prodrug thereof; wherein ------ , $R_6$, $R_3$, $R_3$', G, Y, X, y, x, and n are as defined herein.

In certain embodiments of Formula (I-d3), wherein $R_3$ is —O(CO)$R_8$ or $R_3$' is —O(CO)$R_8$, provided is a compound of Formula (I-d7) and (I-d8) having the following stereochemistry:

(I-d7)

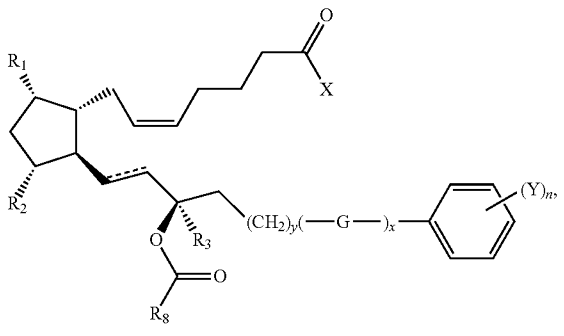

-continued (I-d8)

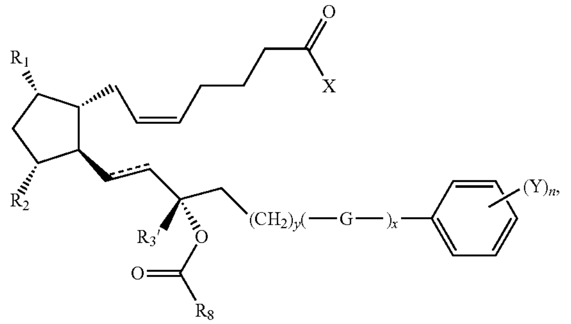

or a pharmaceutically acceptable salt, hydrate, solvate, stereoisomer, polymorph, tautomer, isotopically enriched derivative, or prodrug thereof; wherein ------ , $R_1$, $R_2$, $R_3$, $R_3'$, $R_8$, G, Y, X, y, x, and n are as defined herein.

In certain embodiments of Formula (I-d3), wherein $R_1$ and $R_2$ are each —OH and $R_3$ is —O(CO)$R_8$, or wherein $R_1$ and $R_2$ are each —OH and $R_3'$ is —O(CO)$R_8$, provided is a compound of Formula (I-d9) and (I-d10) having the following stereochemistry:

(I-d9)

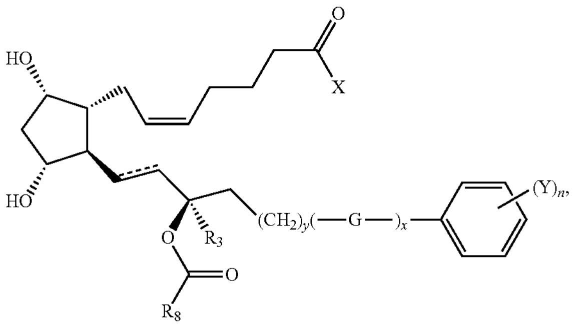

(I-d10)

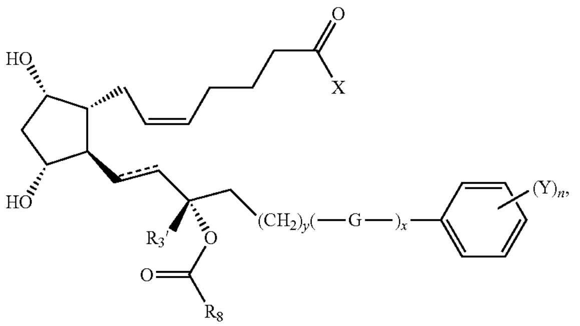

or a pharmaceutically acceptable salt, hydrate, solvate, stereoisomer, polymorph, tautomer, isotopically enriched derivative, or prodrug thereof; wherein, $R_3$, $R_3'$, $R_8$, G, Y, X, y, x, and n are as defined herein.

In certain embodiments of Formula (I-e3), wherein $R_1$ is —OH and $R_2$ is —O(CO)$R_6$, or wherein $R_2$ is —OH and $R_1$ is —O(CO)$R_6$, or wherein both $R_1$ and $R_2$ are —O(CO)$R_6$, and $R_3'$ is hydrogen and $R_3$ is —OH, provided is a compound of Formula (I-d11), (I-d12), and (I-d13) having the following stereochemistry:

(I-d11)

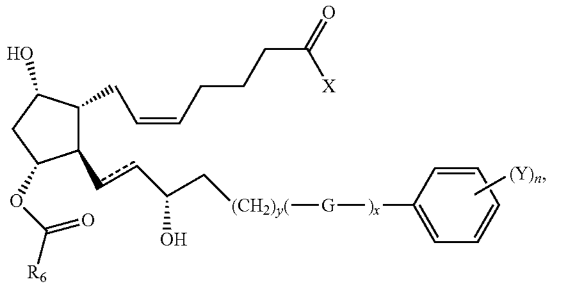

(I-d12)

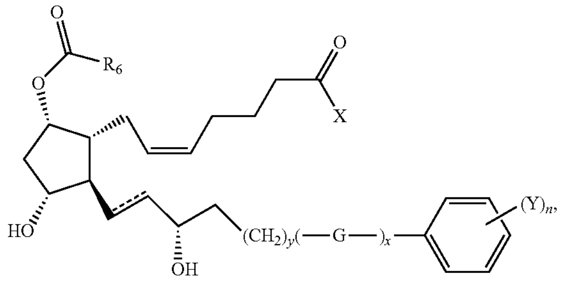

(I-d13)

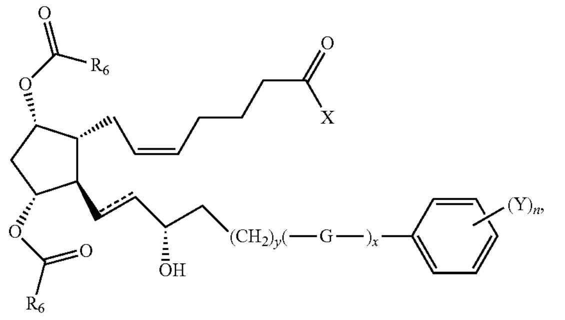

or a pharmaceutically acceptable salt, hydrate, solvate, stereoisomer, polymorph, tautomer, isotopically enriched derivative, or prodrug thereof; wherein ------ , $R_6$, $R_3$, $R_3'$, G, Y, X, y, x, and n are as defined herein.

In certain embodiments of Formula (I-d8), wherein each of $R_1$ and $R_2$ are —O(CO)$R_6$ and $R_3'$ is hydrogen, provided is a compound of Formula (I-d14) having the following stereochemistry:

(I-d14)

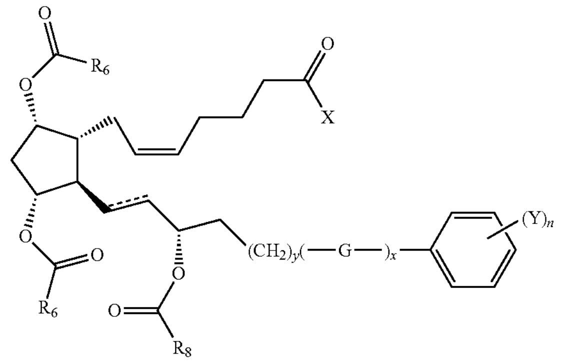

or a pharmaceutically acceptable salt, hydrate, solvate, stereoisomer, polymorph, tautomer, isotopically enriched derivative, or prodrug thereof; wherein ===== , $R_6$, $R_8$, G, Y, X, y, x, and n are as defined herein.

In certain embodiments of Formula (I-d2), wherein Z is =O, each instance of $R_1$ and $R_2$ is —OH, and each ===== represents a single bond, provided is a compound of Formula (I-g):

(I-g)

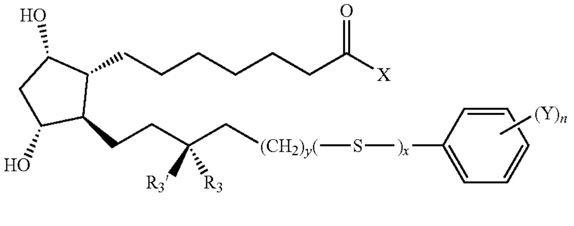

or a pharmaceutically acceptable salt, hydrate, solvate, stereoisomer, polymorph, tautomer, isotopically enriched derivative, or prodrug thereof; wherein X, Y, $R_3$, $R_3'$, y, x, and n are as defined herein.

In certain embodiments of Formula (I-d1), wherein each instance of $R_1$ and $R_2$ is —OH, and Z is =O, provided is a compound of Formula (I-h):

(I-h)

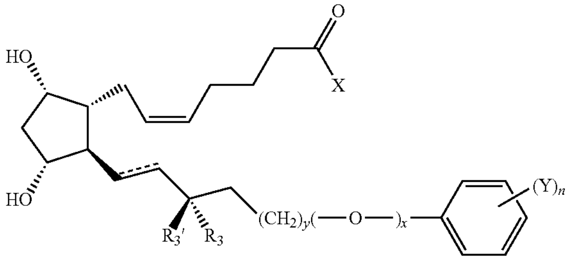

or a pharmaceutically acceptable salt, hydrate, solvate, stereoisomer, polymorph, tautomer, isotopically enriched derivative, or prodrug thereof; wherein ===== , $R_3$, $R_3'$, Y, X, y, x, and n are as defined herein.

In certain embodiments of Formula (I-h), wherein $R_3'$ is hydrogen, provided is a compound of Formula (I-i):

(I-i)

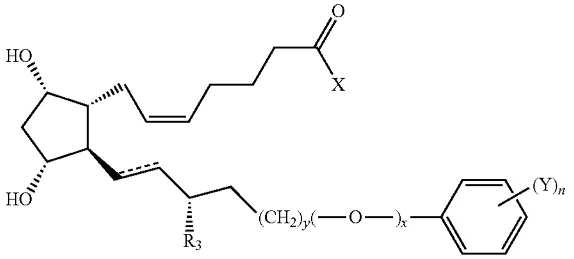

or a pharmaceutically acceptable salt, hydrate, solvate, stereoisomer, polymorph, tautomer, isotopically enriched derivative, or prodrug thereof; wherein ===== , $R_3$, Y, X, y, x, and n are as defined herein.

In certain embodiments of Formula (I-i), wherein $R_3$ is —OH, provided is a compound of Formula (I-j):

(I-j)

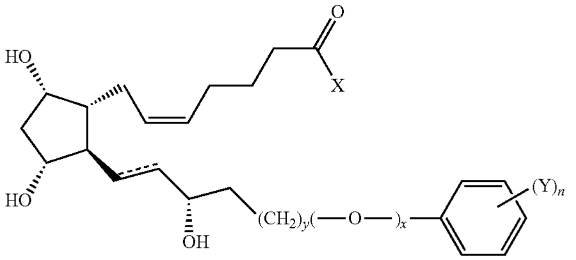

or a pharmaceutically acceptable salt, hydrate, solvate, stereoisomer, polymorph, tautomer, isotopically enriched derivative, or prodrug thereof; wherein Y, X, y, x, and n are as defined herein.

In certain embodiments of Formula (I-h), wherein $R_3$ is F and $R_3'$ is F, provided is a compound of Formula (I-k):

(I-k)

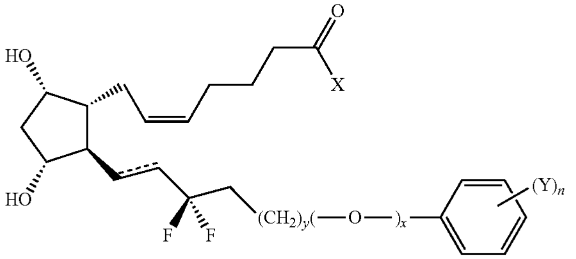

or a pharmaceutically acceptable salt, hydrate, solvate, stereoisomer, polymorph, tautomer, isotopically enriched derivative, or prodrug thereof; wherein ===== , Y, X, y, x, and n are as defined herein.

In certain embodiments of Formula (I-i), wherein $R_3$ is —O(CO)$R_8$, provided is a compound of Formula (I-o):

(I-o)

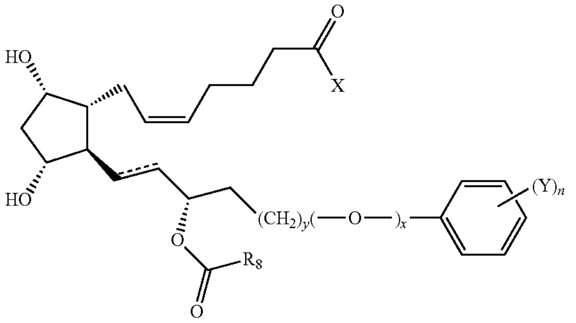

or a pharmaceutically acceptable salt, hydrate, solvate, stereoisomer, polymorph, tautomer, isotopically enriched derivative, or prodrug thereof; wherein $R_8$, Y, X, y, x, and n are as defined herein.

In certain embodiments of Formula (I), the compound of Formula (I-l):

(I-l)

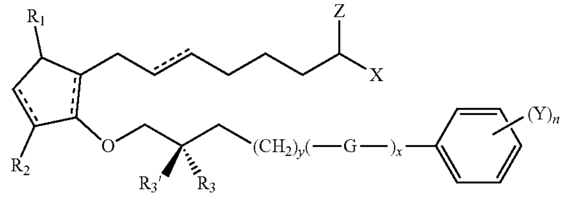

or a pharmaceutically acceptable salt, hydrate, solvate, stereoisomer, polymorph, tautomer, isotopically enriched derivative, or prodrug thereof; wherein $R_1$, $R_2$, Z, and X are as defined herein;

each instance of ------ independently represents a single bond or a double bond which can be in the cis or trans configuration;

each instance of $R_3$ and $R_3$' is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —$(CH_2)_mR_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3$' are joined to form ═O;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino;

G is —O— or —S—;

y is 0, 1, or 2;

x is 0 or 1; and n is 0 or an integer of from 1 to 5, inclusive.

In certain embodiments of Formula (I-l), wherein Z is ═O, and $R_1$ and $R_2$ are each —OH, provided is a compound of Formula (I-m):

(I-m)

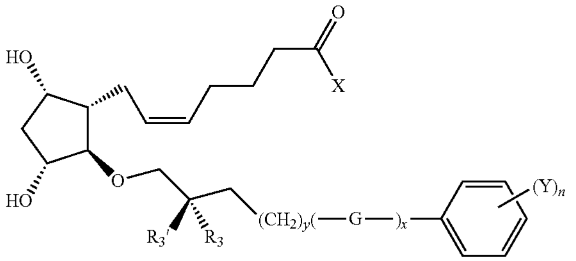

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

In certain embodiments of Formula (I-m), wherein $R_3$' is hydrogen, y is 2 and x is 0, provided is a compound of Formula (I-n):

(I-n)

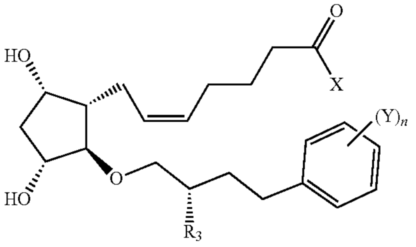

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

As generally defined above, in certain embodiments, provided is a compound of Formula (II):

(II)

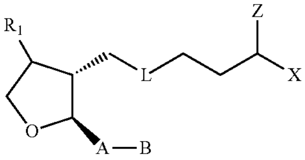

or a pharmaceutically acceptable salt, hydrate, solvate, stereoisomer, polymorph, tautomer, isotopically enriched derivative, or prodrug thereof, wherein A, B, X, Z, L, and $R_1$ are as defined herein are as defined herein.

In certain embodiments, L is a group of the formula

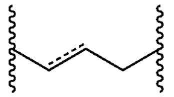

wherein ------ represents a single bond.

In certain embodiments, L is a group of the formula

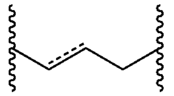

wherein ------ represents a double bond which can be in the cis or trans configuration. In certain embodiments, the double bond is in the cis configuration. In certain embodiments, the double bond is in the trans configuration In certain embodiments, L is a group of the formula

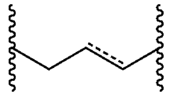

wherein ------ represents a single bond.

In certain embodiments, L is a group of the formula

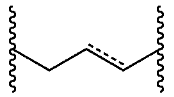

wherein ===== represents a double bond which can be in the cis or trans configuration. In certain embodiments, the double bond is in the cis configuration. In certain embodiments, the double bond is in the trans configuration In certain embodiments of Formula (II), the compound of Formula (II-a):

(II-a)

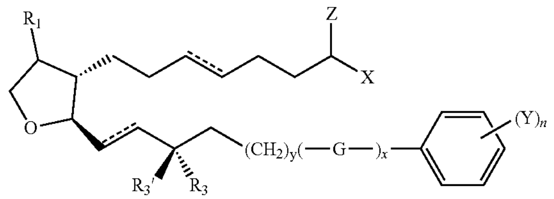

or a pharmaceutically acceptable salt, hydrate, solvate, stereoisomer, polymorph, tautomer, isotopically enriched derivative, or prodrug thereof, wherein ===== , $R_1$, Z, X, Y, G, $R_3$, $R_3$', y, x, and n are as defined herein.

In certain embodiments of Formula (II-a), wherein $R_3$' is hydrogen, the compound is of Formula (II-b):

(II-b)

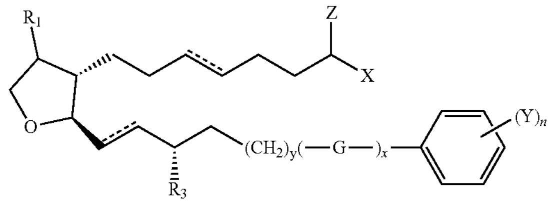

or a pharmaceutically acceptable salt, hydrate, solvate, stereoisomer, polymorph, tautomer, isotopically enriched derivative, or prodrug thereof; wherein ===== , $R_1$, $R_3$, Z, X, Y, G, y, x, and n are as defined herein.

In certain embodiments of Formula (II-a), wherein $R_3$ is hydrogen, the compound is of Formula (II-c):

(II-c)

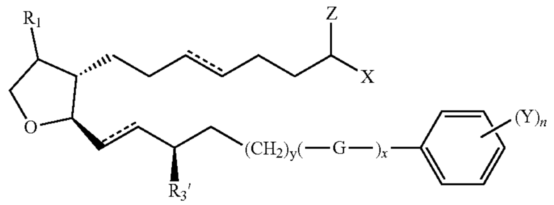

or a pharmaceutically acceptable salt, hydrate, solvate, stereoisomer, polymorph, tautomer, isotopically enriched derivative, or prodrug thereof; wherein ===== , $R_1$, $R_2$, $R_3$', Z, X, Y, G, y, x, and n are as defined herein.

In certain embodiments, G is —O—. In certain embodiments, G is —S—.

In certain embodiments of Formula (II-a), wherein G is —O—, provided is a compound of Formula (II-a1):

(II-a1)

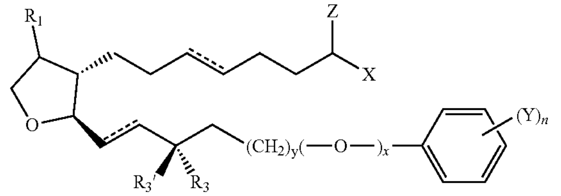

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ===== , $R_1$, $R_2$, $R_3$', Z, X, Y, y, x, and n are as defined herein.

In certain embodiments, Z is =O.

In certain embodiments at least one exocyclic ===== represents a cis-double bond.

For example, in certain embodiments of Formula (II-a1), wherein Z is =O, provided is a compound of Formula (II-d):

(II-d)

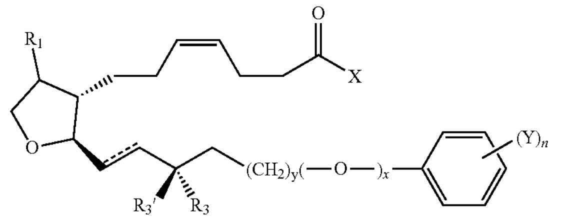

or a pharmaceutically acceptable salt, hydrate, solvate, stereoisomer, polymorph, tautomer, isotopically enriched derivative, or prodrug thereof; wherein ===== , $R_1$, $R_3$, $R_3$', Y, X, y, x, and n are as defined herein.

In certain embodiments of Formula (II-d), wherein $R_1$ is OH, $R_3$' is hydrogen, $R_3$ is —OH, y is 0, and x is 1, provided is a compound of Formula (II-e):

(II-e)

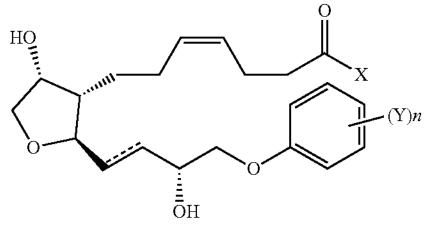

or a pharmaceutically acceptable salt, hydrate, solvate, stereoisomer, polymorph, tautomer, isotopically enriched derivative, or prodrug thereof; wherein ===== , Y, X, and n are as defined herein.

Exemplary compounds of Formula (I) include, but are not limited to:

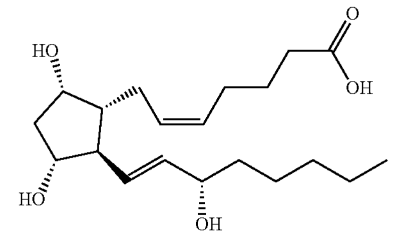 [SMILES: CCCCC[C@H](O)/C=C/[C@@H]1[C@@H](C/C=C\CCCC(=O)O)[C@@H](O)C[C@H]1O]

referred to herein as Prostaglandin F2α;

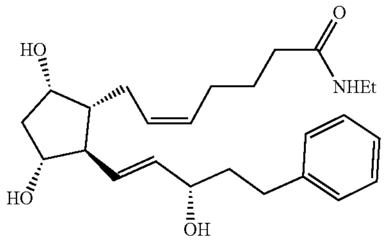

also referred to herein as bimatoprost;

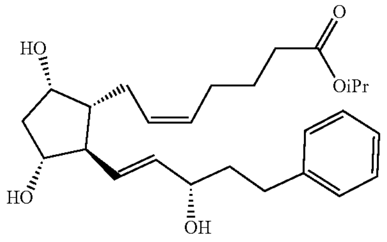 [SMILES: CC(C)OC(=O)CCC/C=C\C[C@@H]1[C@@H](/C=C/[C@@H](O)CCc2ccccc2)[C@H](O)C[C@@H]1O]

also referred to herein as bimatoprost isopropyl ester;

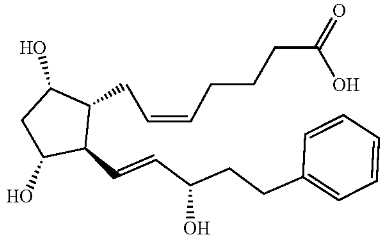 [SMILES: O=C(O)CCC/C=C\C[C@@H]1[C@@H](/C=C/[C@@H](O)CCc2ccccc2)[C@H](O)C[C@@H]1O]

also referred to herein as bimatoprost free acid;

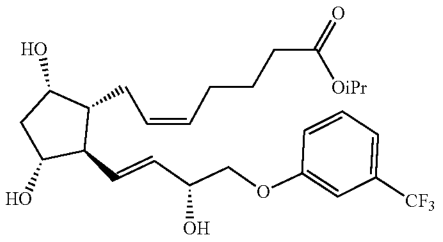 [SMILES: CC(C)OC(=O)CCC/C=C\C[C@@H]1[C@@H](/C=C/[C@@H](O)COc2cccc(C(F)(F)F)c2)[C@H](O)C[C@@H]1O]

also referred to herein as travoprost;

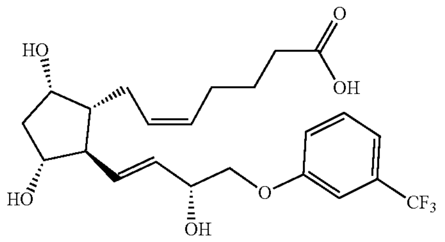

also referred to herein as travoprost free acid or fluprostenol;

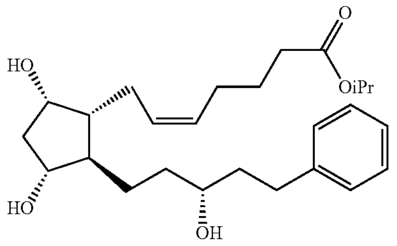 [SMILES: CC(C)OC(=O)CCC/C=C\C[C@@H]1[C@@H](CC[C@@H](O)CCc2ccccc2)[C@H](O)C[C@@H]1O]

also referred to herein as latanoprost;

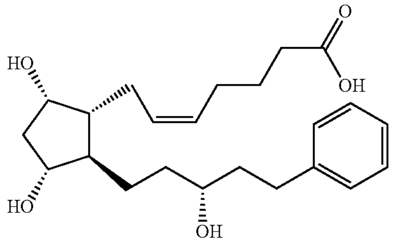 [SMILES: O=C(O)CCC/C=C\C[C@@H]1[C@@H](CC[C@@H](O)CCc2ccccc2)[C@H](O)C[C@@H]1O]

also referred to herein as latanoprost free acid;

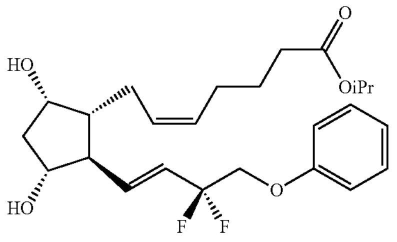

also referred to herein as tafluprost;

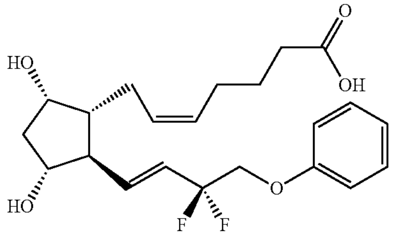

also referred to herein as tafluprost free acid or AFP-172;

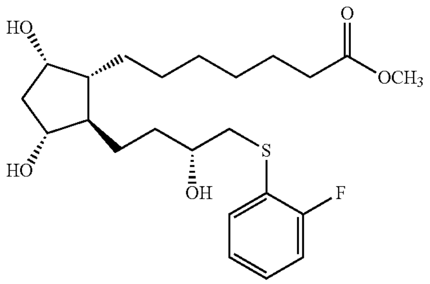 [SMILES: COC(=O)CCCCCC[C@@H]1[C@@H](CC[C@@H](O)CSc2ccccc2F)[C@H](O)C[C@@H]1O]
also referred to herein as CAY10509;
and
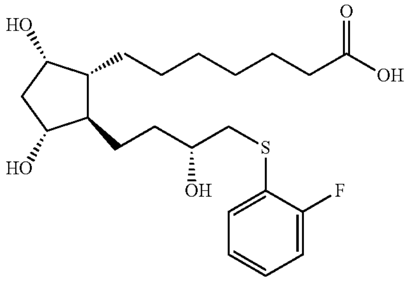 [SMILES: O=C(O)CCCCCC[C@@H]1[C@@H](CC[C@@H](O)CSc2ccccc2F)[C@H](O)C[C@@H]1O]
also referred to herein as CAY10509 free acid;
and 9-, 11-, and/or 15-ester derivatives (e.g., prodrugs) of the above, e.g., of formula:
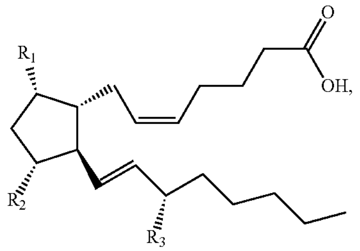
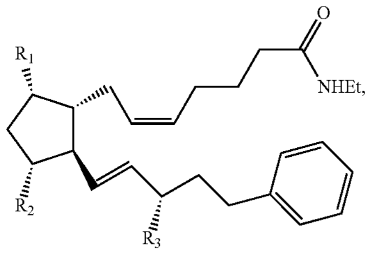
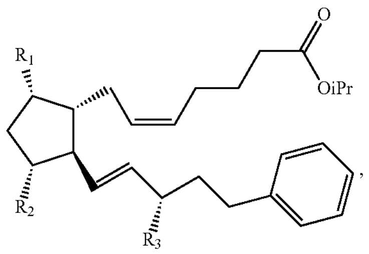
-continued
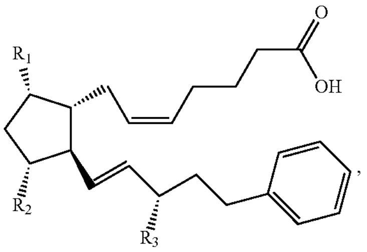
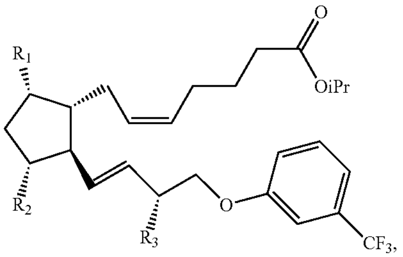
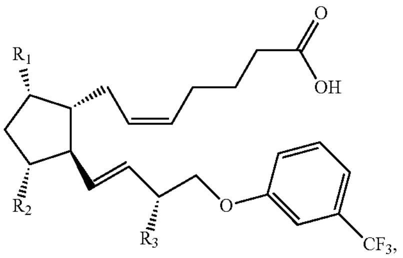
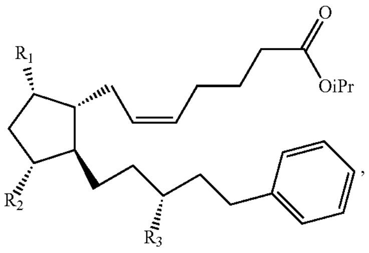
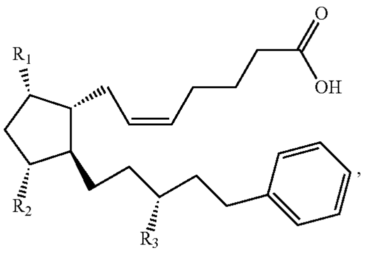
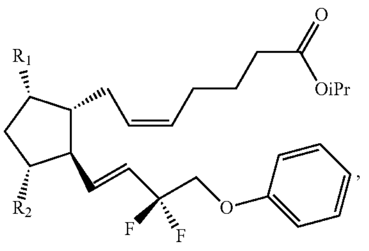

-continued

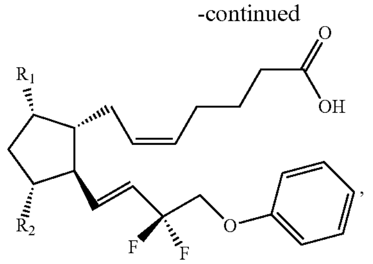

,

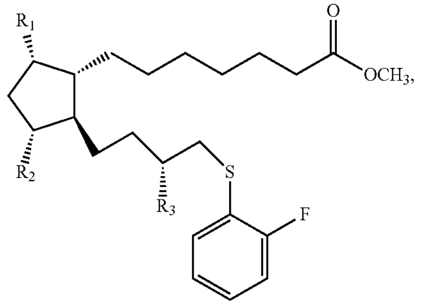

and

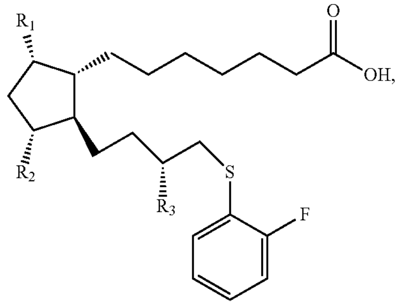

wherein:

$R_1$ is —O(CO)$R_6$ and $R_2$ is —OH, or $R_1$ is —OH, $R_2$ is —O(CO)$R_6$, or $R_1$ is —OH, $R_2$ is —OH, and $R_3$ is —O(CO)$R_5$, or $R_1$ is —OH, $R_2$ is —O(CO)$R_6$, and $R_3$ is —OH, or $R_1$ is —O(CO)$R_6$, $R_2$ is —O(CO)$R_6$, and $R_3$ is —OH, or $R_1$ is —O(CO)$R_6$, $R_2$ is —OH, and $R_3$ is —O(CO)$R_5$, or $R_1$ is —OH, $R_2$ is —O(CO)$R_6$, and $R_3$ is —O(CO)$R_8$, or $R_1$ is —O(CO)$R_6$, $R_2$ is —O(CO)$R_6$, and $R_3$ is —O(CO)$R_8$, wherein $R_6$ and $R_8$ are as defined herein, and pharmaceutically acceptable salts, hydrates, solvates, stereoisomers, polymorphs, tautomers, isotopically enriched derivatives, and prodrugs thereof. In certain embodiments, $R_5$ is —$(CH_2)_q$ $CH_3$ wherein q is 0, 1, 2, 3, 4, 5, or 6, —CH$(CH_3)_2$, —$CH_2CH(CH_3)_2$, —$CH_2C(CH_3)_3$, or —$C(CH_3)_3$. In certain embodiments, $R_6$ is —$(CF_{12})_rCH_3$ wherein r is 0, 1, 2, 3, 4, 5, or 6, —$CH(CH_3)_2$, —$CH_2CH(CH_3)_2$, —$CH_2C(CH_3)_3$, or —$C(CH_3)_3$.

In certain embodiments, the compound of Formula (I) is selected from the group consisting of latanoprost, latanoprost free acid, tafluprost, tafluprost free acid, travoprost, fluprostenol, bimatoprost, bimatoprost free acid, and pharmaceutically acceptable salts, hydrates, solvates, stereoisomers, polymorphs, tautomers, isotopically enriched derivatives, and prodrugs thereof. In certain embodiments, the compound of Formula (I) is selected from the group consisting of latanoprost, latanoprost free acid, tafluprost, tafluprost free acid, and pharmaceutically acceptable salts, hydrates, solvates, stereoisomers, polymorphs, tautomers, isotopically enriched derivatives, and prodrugs thereof. In certain embodiments, the compound of Formula (I) is selected from the group consisting of latanoprost and pharmaceutically acceptable hydrates, solvates, stereoisomers, polymorphs, tautomers, isotopically enriched derivatives, and prodrugs thereof. In certain embodiments, the compound of Formula (I) is selected from the group consisting of latanoprost free acid and pharmaceutically acceptable salts, hydrates, solvates, stereoisomers, polymorphs, tautomers, isotopically enriched derivatives, and prodrugs thereof. In certain embodiments, the compound of Formula (I) is latanoprost. In certain embodiments, the compound of Formula (I) is selected from the group consisting of tafluprost and pharmaceutically acceptable hydrates, solvates, stereoisomers, polymorphs, tautomers, isotopically enriched derivatives, and prodrugs thereof. In certain embodiments, the compound of Formula (I) is selected from the group consisting of tafluprost free acid and pharmaceutically acceptable salts, hydrates, solvates, stereoisomers, polymorphs, tautomers, isotopically enriched derivatives, and prodrugs thereof. In certain embodiments, the compound of Formula (I) is tafluprost.

Exemplary compounds of Formula (II) include, but are not limited to,

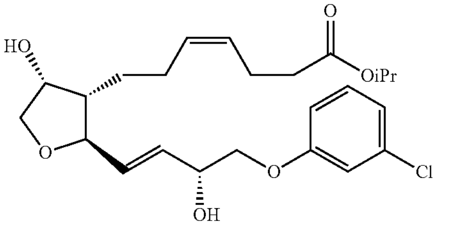 [SMILES: CC(C)OC(=O)CC/C=C\CC[C@H]1[C@@H](O)CO[C@@H]1/C=C/[C@@H](O)COc1cccc(Cl)c1]

also referred to as AL-12182;

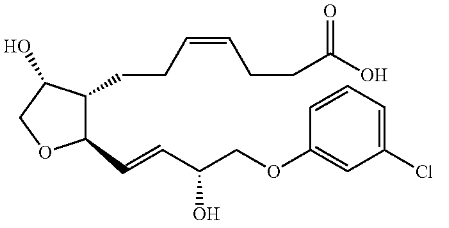 [SMILES: O=C(O)CC/C=C\CC[C@H]1[C@@H](O)CO[C@@H]1/C=C/[C@@H](O)COc1cccc(Cl)c1]

also referred to as AL-12182 free acid;

and ester derivatives (e.g., prodrugs) of the above, e.g., of formula:

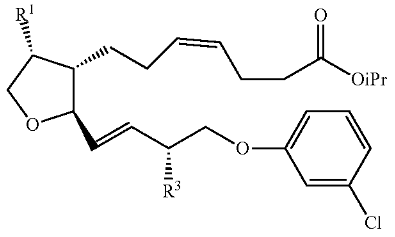

and

-continued

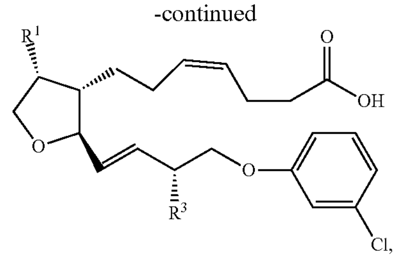

wherein:

$R_1$ is —OH and $R_3$ is —O(CO)$R_5$, or $R_1$ is —O(CO)$R_6$, and $R_3$ is —OH, or $R_1$ is —O(CO)$R_6$, and $R_3$ is —O(CO)$R_8$, wherein $R_6$ and $R_8$ are as defined herein, and pharmaceutically acceptable salts, hydrates, solvates, stereoisomers, polymorphs, tautomers, isotopically enriched derivatives, and prodrugs thereof. In certain embodiments, $R_8$ is —$(CH_2)_qCH_3$ wherein q is 0, 1, 2, 3, 4, 5, or 6, —$CH(CH_3)_2$, —$CH_2CH(CH_3)_2$, —$CH_2C(CH_3)_3$, or —$C(CH_3)_3$. In certain embodiments, $R_6$ is —$(CH_2)_rCH_3$ wherein r is 0, 1, 2, 3, 4, 5, or 6, —$CH(CH_3)_2$, —$CH_2CH(CH_3)_2$, —$CH_2C(CH_3)_3$, or —$C(CH_3)_3$.

In certain embodiments, the compound of Formula (I) or (II) is a prodrug of any one of the compounds described herein. Exemplary prodrugs include esters, amides, and/or thioamides of the parent free acid, and compounds wherein a hydroxyl group on the parent compound (e.g., a pentacyclic hydroxyl group $R_1$ and/or $R_2$ or the hydroxyl group at the $R_3$ and/or $R_3'$ position) is esterified, e.g., 9-, 11-, and/or 15-ester derivatives as described herein, e.g., wherein the ester at said position is a $C_{1-6}$ ester, e.g., 9-propionyl bimatoprost, 11-propionyl bimatoprost, 15-propionyl bimatoprost, 9-butyryl bimatoprost, 11-butyryl bimatoprost, 15-butyryl bimatoprost, and the like.

Compositions and Formulations

In certain embodiments, the present invention provides compositions for topical administration of a composition comprising a PFPRA compound, as described herein, and a fatty acid, e.g., oleic acid.

In certain embodiments, the composition further comprises an organic alcohol. In some embodiments, the composition further comprises a viscosity-enhancing agent. In certain embodiments, the composition further comprises an antioxidant. In certain embodiments, the composition is a solution. In certain embodiments, the composition is not irritating to the skin.

In some embodiments, the PFPRA compound is a compound of Formula (I) or (II), or a pharmaceutically acceptable salt, hydrate, solvate, stereoisomer, polymorph, tautomer, isotopically enriched derivative, or prodrug thereof. In some embodiments, the PFPRA compound is latanoprost, tafluprost, travoprost, or bimatoprost, or a pharmaceutically acceptable salt, hydrate, solvate, stereoisomer, polymorph, tautomer, isotopically enriched derivative, or prodrug thereof. In certain embodiments, the PFPRA compound is selected from the group consisting of latanoprost, latanoprost free acid, tafluprost, tafluprost free acid, and pharmaceutically acceptable salts, hydrates, solvates, stereoisomers, polymorphs, tautomers, isotopically enriched derivatives, and prodrugs thereof. In certain embodiments, the PFPRA compound is selected from the group consisting of latanoprost and pharmaceutically acceptable hydrates, solvates, stereoisomers, polymorphs, tautomers, isotopically enriched derivatives, and prodrugs thereof. In certain embodiments, the PFPRA compound is selected from the group consisting of latanoprost free acid and pharmaceutically acceptable salts, hydrates, solvates, stereoisomers, polymorphs, tautomers, isotopically enriched derivatives, and prodrugs thereof. In certain embodiments, the PFPRA compound is selected from the group consisting of tafluprost and pharmaceutically acceptable hydrates, solvates, stereoisomers, polymorphs, tautomers, isotopically enriched derivatives, and prodrugs thereof. In certain embodiments, the PFPRA compound is selected from the group consisting of tafluprost free acid and pharmaceutically acceptable salts, hydrates, solvates, stereoisomers, polymorphs, tautomers, isotopically enriched derivatives, and prodrugs thereof. In certain embodiments, the PFPRA compound is latanoprost. In certain embodiments, the PFPRA compound is tafluprost. In certain embodiments, the PFPRA compound hydrolyzes to an active metabolite (e.g., the free acid of latanoprost, tafluprost, travoprost, or bimatoprost) upon administration to the skin.

In some embodiments, the final concentration of the PFPRA compound provided in the composition is between about 0.0001 percent and about 1 percent (by weight), inclusive. In some embodiments, the final concentration is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 percent and about 0.5 percent, or about 0.3 and about 1 percent (by weight), inclusive. These percentages are expressed by weight of the total weight of the composition.

In some embodiments, the final concentration of the fatty acid is between about 1 percent to about 20 percent by weight, inclusive. In some embodiments, the final concentration of the fatty acid is between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, inclusive. In certain embodiments, the final concentration of the fatty acid is 1, 2, 3, 4, 5, 6, 7, 8, 9, 10, 11, 12, 13, 14, 15, 16, 17, 18, 19, or 20 percent by weight. In some embodiments, the fatty acid is oleic acid and the final concentration of the oleic acid is between about 1 percent to about 20 percent by weight, inclusive. In some embodiments, the final concentration of the oleic acid is between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, inclusive. In certain embodiments, the final concentration of the oleic acid is 1, 2, 3, 4, 5, 6, 7, 8, 9, 10, 11, 12, 13, 14, 15, 16, 17, 18, 19, or 20 percent by weight. These percentages are expressed by weight of the total weight of the composition.

In some embodiments, the composition further comprises an organic alcohol, e.g., methanol, ethanol, propanol, isopropanol, 1,3-butanediol, ethylene glycol, or propylene glycol, or mixture thereof. In some embodiments, the composition comprises a PFPRA compound, a fatty acid (e.g., oleic acid), and ethanol. In some embodiments, the composition comprises a PFPRA compound, a fatty acid (e.g., oleic acid), and propylene glycol. In some embodiments, the composition is a solution comprising a PFPRA compound, a fatty acid (e.g., oleic acid), propylene glycol, and ethanol. In certain embodiments, the composition consists essentially of the above recited components. In some embodiments, the composition comprises latanoprost, a fatty acid (e.g., oleic acid), and ethanol. In some embodiments, the composition comprises latanoprost, a fatty acid (e.g., oleic acid), and propylene glycol. In some embodiments, the composition is a solution comprising latanoprost, a fatty acid (e.g., oleic acid), propylene glycol, and ethanol. In certain embodiments, the composition consists essentially of the above recited components. In some embodiments, the composition comprises tafluprost, a fatty acid (e.g., oleic acid), and ethanol. In some embodiments, the composition comprises tafluprost, a fatty acid (e.g., oleic acid), and propylene glycol. In some embodiments, the composition is a solution comprising tafluprost, a fatty acid (e.g., oleic acid), propylene glycol, and ethanol. In certain embodiments, the composition consists essentially of the above recited components.

In some embodiments, the composition comprises an organic alcohol which acts as a base excipient (i.e., constituting the major component of the formulation, such as for example, provided in greater than 50% by weight). In some embodiments, the final concentration of the organic alcohol base excipient is between about 40 percent and about 99.5 percent by weight, inclusive. In some embodiments, the final concentration of the organic alcohol base excipient is greater than 50 percent and about 99 percent by weight, inclusive. In some embodiments, the final concentration of the organic alcohol base excipient is between about 51 percent and 60 percent, 51 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent, inclusive. In certain embodiments, the organic alcohol which acts as a base excipient is ethanol. In these embodiments, the final concentration of the ethanol base excipient is between about 51 percent and 60 percent, 51 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the composition comprises water. The water may be, for example, tap water, distilled water, or deionized water. In some embodiments, the final concentration of water is between about 0.1 percent and about 30 percent by weight, inclusive. In some embodiments, the final concentration of water is between about 0.1 percent and 25 percent, about 0.2 percent and about 20 percent, about 0.3 percent and about 15 percent, about 0.4 percent and about 10 percent, about 0.5 percent and about 8 percent, about 1 percent and about 5 percent, inclusive. In certain embodiments, the water replaces part of the organic alcohol (such as ethanol) which acts as the base component of the composition.

In some embodiments, the composition comprises glycerin, i.e., glycerol. In some embodiments, the final concentration of glycerin is between about 0.1 percent and about 30 percent by weight, inclusive. In some embodiments, the final concentration of glycerin is between about 0.1 percent and 25 percent, about 0.2 percent and about 20 percent, about 0.3 percent and about 15 percent, about 0.4 percent and about 10 percent, about 0.5 percent and about 8 percent, about 1 percent and about 5 percent, inclusive. In certain embodiments, the glycerin replaces part of the organic alcohol (such as ethanol) which acts as the base component of the composition.

In some embodiments, the composition comprises an organic alcohol which is not the base component of the composition (e.g., provided as a component in 50% or less by weight). In certain embodiments, the final concentration of the organic alcohol is between about 5 percent and about 50 percent by weight, inclusive. In some embodiments, the final concentration of the organic alcohol is between about 5 percent and 10 percent, about 5 percent and about 15 percent, about 10 percent and about 15 percent, about 10 percent and about 20 percent, about 15 percent and about 20 percent, about 15 percent and about 25 percent, about 20 percent and about 25 percent, about 20 percent and 30 percent, about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. In certain embodiments, the composition comprises an organic alcohol in 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight. In certain embodiments, the organic alcohol is propylene glycol. In these embodiments, the final concentration of the propylene glycol is between about 5 percent and 10 percent, about 5 percent and about 15 percent, about 10 percent and about 15 percent, about 10 percent and about 20 percent, about 15 percent and about 20 percent, about 15 percent and about 25 percent, about 20 percent and about 25 percent, about 20 percent and 30 percent, about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. In certain embodiments, the composition comprises propylene glycol in 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight.

In certain embodiments, the composition comprises:

(a) a PFPRA compound (e.g., latanoprost or tafluprost) in a concentration of between about 0.0001 percent and about 1 percent (by weight), such as 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 percent and about 0.5 percent, or about 0.3 and about 1 percent (by weight), inclusive; and (b) a fatty acid (e.g., oleic acid) in a concentration of between about 0.1 percent to about 20 percent by weight, such as between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, such as 1, 2, 3, 4, 5, 6, 7, 8, 9, 10, 11, 12, 13, 14, 15, 16, 17, 18, 19, or 20 percent by weight, inclusive.

In certain embodiments, the composition comprises:

(a) a PFPRA compound (e.g., latanoprost or tafluprost) in a concentration of between about 0.0001 percent and about 1 percent (by weight), such as 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 percent and about 0.5 percent, or about 0.3 and about 1 percent (by weight), inclusive;

(b) a fatty acid (e.g., oleic acid) in a concentration of between about 1 percent to about 20 percent by weight, such as between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, such as 1, 2, 3, 4, 5, 6, 7, 8, 9, 10, 11, 12, 13, 14, 15, 16, 17, 18, 19, or 20 percent by weight, inclusive; and (c) an organic alcohol (e.g., ethanol) in a concentration of between about 51 percent and 60 percent, 51 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent, inclusive.

In certain embodiments, the composition comprises:

(a) a PFPRA compound (e.g., latanoprost or tafluprost) in a concentration of between about 0.0001 percent and about 1 percent (by weight), such as 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 percent and about 0.5 percent, or about 0.3 and about 1 percent (by weight), inclusive;

(b) a fatty acid (e.g., oleic acid) in a concentration of between about 1 percent to about 20 percent by weight, such as between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, such as 1, 2, 3, 4, 5, 6, 7, 8, 9, 10, 11, 12, 13, 14, 15, 16, 17, 18, 19, or 20 percent by weight, inclusive; and (c) an organic alcohol (e.g., propylene glycol) in a final concentration of between about 5 percent and about 50 percent by weight, such as between about 5 percent and 10 percent, about 5 percent and about 15 percent, about 10 percent and about 15 percent, about 10 percent and about 20 percent, about 15 percent and about 20 percent, about 15 percent and about 25 percent, about 20 percent and about 25 percent, about 20 percent and 30 percent, about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight, inclusive.

In certain embodiments, the composition comprises:

(a) a PFPRA compound (e.g., latanoprost or tafluprost) in a concentration of between about 0.0001 percent and about 1 percent (by weight), such as 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 percent and about 0.5 percent, or about 0.3 and about 1 percent (by weight), inclusive;

(b) a fatty acid (e.g., oleic acid) in a concentration of between about 1 percent to about 20 percent by weight, such as between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, such as 1, 2, 3, 4, 5, 6, 7, 8, 9, 10, 11, 12, 13, 14, 15, 16, 17, 18, 19, or 20 percent by weight, inclusive;

(c) a first organic alcohol (e.g., ethanol) in a concentration of between about 51 percent and 60 percent, 51 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent, inclusive; and (d) a second organic alcohol (e.g., propylene glycol) in a final concentration of between about 5 percent and about 50 percent by weight, such as between about 5 percent and 10 percent, about 5 percent and about 15 percent, about 10 percent and about 15 percent, about 10 percent and about 20 percent, about 15 percent and about 20 percent, about 15 percent and about 25 percent, about 20 percent and about 25 percent, about 20 percent and 30 percent, about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight, inclusive.

In certain embodiments, the composition comprises a PFPRA compound (e.g., latanoprost or tafluprost), oleic acid in about 3% by weight, and an organic alcohol (e.g., propylene glycol or ethanol) in about 27% by weight.

In some embodiments, the composition further comprises a viscosity enhancing agent. A viscosity-enhancing agent, as used herein, is a substance which increases the viscosity of a solution or liquid/solid mixture. Exemplary viscosity enhancing agents include, but are not limited to, glycerin; cellulose derivatives (e.g., methylcellulose (MC); hydroxypropylmethylcellulose (HPMC); carboxymethylcellulose (CMC); microcrystalline cellulose (CC); ethyl cellulose;

hydroxyethyl cellulose (HEC); hydroxypropyl cellulose (HPC); cellulose); gelatin; starch; hetastarch; poloxamers; pluronics; sodium CMC; sorbitol; acacia; povidone; carbopol; polycarbophil; chitosan; alginate; chitosan glutamate; hyaluronic acid; elastin; hyaluronan; maltodextrin DE; deoxyglycocholate (GDC); polymethacrylic acid; glycols (e.g., polymethylene glycol; polyethylene glycol); cyclodextrins (e.g., sulfobutylether B cyclodextrin); sodium taurodihydrofusidate (STDHF); and N-trimethyl chitosan chloride (TMC). In certain embodiments, the viscosity enhancing agent is a cellulose derivative, e.g., hydroxypropyl cellulose (HPC). In certain embodiments, the composition comprises a viscosity enhancing agent between about 0.5% and about 5% by weight, inclusive. In certain embodiments, the composition comprises a viscosity enhancing agent in between about 0.5% and about 4%, between about 0.5% and about 3%, between about 0.5% and about 2%, between about 0.5% and about 1%, between about 0.8% and about 5%, between about 0.8% and about 4%, between about 0.8% and about 3%, between about 0.5% and about 2%, or between about 0.5% and about 1%, inclusive. In certain embodiments, the composition comprises a viscosity enhancing agent in about 0.5%, 0.6%, 0.7%, 0.8%, 0.9%, 1%, 2%, 3%, 4%, or 5% (by weight). In certain embodiments, the viscosity enhancing agent is hydroxypropyl cellulose and the composition comprises hydroxypropyl cellulose in between about 0.5% and about 4%, between about 0.5% and about 3%, between about 0.5% and about 2%, between about 0.5% and about 1%, between about 0.8% and about 5%, between about 0.8% and about 4%, between about 0.8% and about 3%, between about 0.5% and about 2%, or between about 0.5% and about 1%, inclusive. In certain embodiments, the composition comprises hydroxypropyl cellulose in about 0.5%, 0.6%, 0.7%, 0.8%, 0.9%, 1%, 2%, 3%, 4%, or 5% (by weight). In certain embodiments, the composition comprises hydroxypropylcellulose in about 1% by weight.

In certain embodiments, the composition further comprises an antioxidant, e.g., alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite. In certain embodiments, the composition comprises an antioxidant between about 0.001% and about 0.1% by weight, inclusive. In certain embodiments, the composition comprises an antioxidant in between about 0.001% and about 0.05%, 0.001% and about 0.04%, 0.001% and about 0.03%, 0.001% and about 0.02%, 0.001% and about 0.01%, inclusive. In certain embodiments, the composition comprises an antioxidant in about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1% by weight. In certain embodiments, the antioxidant is alpha tocopherol and the composition comprises alpha tocopherol in between about 0.001% and about 0.05%, 0.001% and about 0.04%, 0.001% and about 0.03%, 0.001% and about 0.02%, 0.001% and about 0.01%, inclusive. In certain embodiments, the composition comprises alpha tocopherol in about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1% by weight. In certain embodiments, the composition comprises alpha tocopherol in about 0.002% by weight.

In certain embodiments, the composition may further comprise other pharmaceutically acceptable excipients including, but not limited to, solvents, diluents or other liquid vehicles, dispersion or suspension aids, surface active agents, isotonic agents, thickening or emulsifying agents, preservatives, lubricants and the like. General considerations in the formulation and/or manufacture of topical compositions can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $^{21st}$ Edition (Lippincott Williams & Wilkins, 2005).

Compositions can be prepared, packaged, and/or sold in bulk, as a single unit dose, and/or as a plurality of single unit doses. As used herein, a "unit dose" is discrete amount of the composition comprising a predetermined amount of the PFPRA compound. The amount of the PFPRA compound is generally equal to the dosage of the PFPRA compound which would be administered to a subject and/or a convenient fraction of such a dosage such as, for example, one-half or one-third of such a dosage.

Relative amounts of the PFPRA compound, the pharmaceutically acceptable excipient, and/or any additional ingredients in a composition will vary, depending upon the identity, size, and/or condition of the subject treated and further depending upon the route by which the composition is to be administered.

Other Features of Compositions

Pharmaceutically acceptable excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as coloring agents, coating agents, perfuming agents, and sunscreens may also be present in the composition.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include lipids/natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Chlorobutanol, for example, can be used as a preservative in an ointment formulation at a concentration of 0.001% to 1% by weight (such as 0.5% per weight) of the total weight of the final composition.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

A composition of the invention can be combined with, incorporated into, and/or delivered by means of a patch or dressing, which often have the added advantage of providing controlled delivery of the PFPRA compound to the body. Alternatively or additionally, the rate can be controlled by either providing a rate controlling membrane and/or by dispersing the PFPRA compound in a polymer matrix and/or gel.

The composition may further comprise one or more of the additional ingredients described herein. In some embodiments, the additional ingredient is a sunscreen, moisturizer, colorant, antibiotic, antifungal, antiviral, antifibrotic, anti-inflammatory, anesthetic, analgesic, vasoconstrictor, vasodilator, vitamin or mineral, or antioxidant.

Although the descriptions of compositions provided herein are principally directed to compositions that are suitable for topical administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of compositions can be found, for example, in Remington: *The Science and Practice of Pharmacy* 21st ed., Lippincott Williams & Wilkins, 2005.

Still further encompassed by the invention are kits comprising a composition of the invention as described herein and instructions for use. Kits provided may comprise a provided composition and a container (e.g., a tube, vial, ampoule, bottle, syringe, and/or dispenser package, or other suitable container).

Methods of Treatment and Use

As generally described herein, the compositions described herein are contemplated useful in the reduction of subcutaneous fat in a subject in need thereof. Methods of use and treatment include therapeutic methods and cosmetic methods, as described herein. For example, in one aspect, provided is a method of reducing body fat in a subject, comprising topically administering a composition as described herein to a subject in need thereof. In another aspect, provided is a composition of the present invention for use in method of reducing body fat in a subject. In another aspect, provided use of a composition of the present invention in the manufacture of a medicament for reducing body fat in a subject. In certain embodiments, the method is a therapeutic method. In certain embodiments, the method is a cosmetic method.

Fat reduction can include reducing fat as measured by at least one of volume, size, mass, bulk, density, amount, and/or quantity. The present invention is expected to reduce fat by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%. For example, fat reduction can also include reducing fat cell amount (for example, fat cell number), reducing fat cell volume, reducing fat cell maturation, and/or dedifferentiating a fat cell.

In certain embodiments, the body fat is local, e.g., concentrated on the face, chin, neck, arms, abdomen, chest, breast, buttocks, hips, thighs, legs, and/or knees.

In certain embodiments, the subject suffers from or is likely to suffer from obesity, excess fat on the breast, excess fat on the chin, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, HIV lipodystrophy, orbital fat prolapse, age-related descent of abnormal fat, other acquired lipodystrophy, familial lipodystrophy, lipoma, lipomatosis, or Madelung disease. In certain embodiments, the subject suffers from or is likely to suffer from obesity, gynecomastia, HIV lipodystrophy, lipoma, steatoblepharon, excess eyelid fat, excess periorbital fat, or excess fat on the chin. In certain embodiments, the subject has a cosmetic condition.

In certain embodiments, the subject suffers from or is likely to suffer from excess submental fat. Thus, in one aspect, provided is a composition for use in for reducing fat in a subject suffering from excess submental fat. In another aspect, provided is a method of treating excess submental fat in a subject, comprising topically administering (e.g., applying to the submental skin of the subject) a composition as described herein to a subject in need thereof. In another aspect, provided is a composition as described herein for use in a method of treating excess submental fat in a subject. In another aspect, provided is use a composition as described herein in the manufacture of a medicament for treating excess submental fat in a subject.

In certain embodiments, the subject suffers from or is likely to suffer from steatoblepharon. Thus, in one aspect, provided is a composition for use in for reducing fat in a subject suffering from steatoblepharon. In another aspect, provided is a method of treating steatoblepharon in a subject, comprising topically administering (e.g., applying to an eyelid of the subject) a composition as described herein to a subject in need thereof. In another aspect, provided is a composition as described herein for use in a method of treating steatoblepharon in a subject. In another aspect, provided is use a composition as described herein in the manufacture of a medicament for treating steatoblepharon in a subject.

As described herein, the route of administering is topical. In certain embodiments, the administering is to a body part selected from the group consisting of the face, chin, submental region, jowls, cheeks, periorbital skin, neck, arms, abdomen, chest, breast, buttocks, hips, thighs, legs, and knees.

In certain embodiments, the subject has excess body fat as a side effect of medication (e.g., for example, cortisol and analogs, corticosteroids, megace, sulfonylureas, anti-retrovirals, antidepressants, monoamine oxidase inhibitors, selective serotonin reuptake inhibitors, oral contraceptives, insulin or a form of insulin, risperidone, clozapine, and thiazolidinediones).

In certain embodiments, the subject has excess body fat due to changes in hormonal status (e.g., as a result of physiologic changes such as pregnancy or menopause).

In certain embodiments, the subject with excess body fat is undergoing or has recently undergone smoking cessation.

In certain embodiments, the subject has body fat of cosmetic significance, for example, due to age-related orbital fat prolapse, excess submental fat, or descent of the malar fat pads.

This aspect of invention may also be useful as an adjunct to any of various kinds of surgery and/or non-invasive therapy, whether used in the pre-operative, peri-operative, or post-operative period. The invention further contemplates uses preceding abdominal, thoracic, oncologic, endocrine, neurologic, transplant, and dermatologic surgery, whereby surgical exposure may be improved; preceding or following orthopedic procedures, whereby surgical exposure as well as post-operative recovery may be improved; and preceding cosmetic procedures using lasers, another type of radiation, thermal therapy, cryotherapy, ultrasound, electrolysis, chemical treatment and the like, e.g., skin tightening, skin resurfacing, collagen remodeling, and the like.

EXAMPLES

Throughout the description, where compositions are described as having, including, or comprising specific components, it is contemplated that these compositions may also consist essentially of, or consist of, the recited components. Further, it should be understood that the order of steps or order for performing certain actions are immaterial so long as the invention remains operable. Moreover, two or more steps or actions may be conducted simultaneously. In light of the foregoing description, the specific non-limiting examples presented below are for illustrative purposes and not intended to limit the scope of the invention in any way.

Example 1

A topical composition for local reduction of subcutaneous fat was prepared as follows:

TABLE 1

| Ingredients | Amount |
|---|---|
| Latanoprost | 100 mg |
| alpha-Tocopherol | 2 mg |
| Ethanol, anhydrous | 69.9 g |
| Propylene glycol | 27 g |
| Oleic acid | 3 g |
| Hydroxypropylcellulose (e.g., Klucel ® Grade HF) | 1 g |

Neat latanoprost was dissolved in ethanol. Propylene glycol and oleic acid were added, and the resulting preparation was thoroughly mixed. Hydroxypropylcellulose was added and thoroughly mixed to yield about 100 grams of gel with a final latanoprost concentration of about 0.1% (w/w).

It was found during the course of the experiments with this and other latanoprost formulations that latanoprost (prodrug) was converted (hydrolyzed) to the active metabolite, latanoprost free acid, in the skin samples. See, e.g., Example 4.

Example 2

A composition was prepared according to Example 1. High Performance Liquid Chromatography (HPLC) verified the latanoprost concentration and lack of impurities. The composition was stored under long-term and accelerated stability conditions (25° C./60% relative humidity and 45° C./75% relatively humidity, respectively). The composition was reanalyzed and tested on HPLC at regular intervals for 6 months. Standard tests for microbial growth were also performed. At each interval, organoleptic inspection showed physical stability of the composition, and HPLC shows a stable latanoprost concentration and a lack of known degradants (e.g., latanoprost free acid, 15-keto latanoprost). Furthermore, no microbes were detected. Thus, it was concluded that the composition demonstrates excellent physical and chemical stability.

Example 3

A composition was prepared according to Example 1. The composition was subjected to various harsh environmental conditions in an attempt to cause degradation. The presence of degradants or impurities was assessed using a stability-indicating HPLC method, i.e., a method proven to detect known degradants of latanoprost. No degradation was observed following exposure to intense ultraviolet light for 4 days or elevated temperature (75° C.) for 24 hours. Furthermore, the physical characteristics of the composition were unchanged following exposure to low temperature (−20° C.) for 24 hours (e.g., there was no solidification or separation). Thus, it was concluded that the composition remains stable despite environmental stressors that can occur during the storage and distribution of a commercial product.

Example 4

Skin permeation studies were conducted with various formulations of latanoprost, ex vivo, on fresh human skin. Fresh human skin was obtained from live donors undergoing abdominoplasty and mounted on a standard (Franz-type) diffusion cell apparatus. All test articles contained 0.8% (weight/weight) of latanoprost. Each test article (8 mg) was uniformly applied to a skin surface of 0.8 $cm^2$. All formulations were tested on skin from at least two different donors. Treated skin was left open to the atmosphere to simulate clinical conditions. Receptor fluid flowed continuously over 24 hours and was collected in fractions. The amount of active drug metabolite (latanoprost free acid) in these fractions was determined by Liquid Chromatography/Tandem Mass Spectrometry. The following amounts of drug were recovered from receptor fluid over 24 hours:

TABLE 2

| Formulation | Drug mass (ng, mean) |
|---|---|
| Ethanol 70%, PG 27%, oleic acid 3% | 7120 |
| Ethanol 70%, PG 30% | 3930 |
| Ethanol 75%, DGME 25% | 1260 |
| Ethanol 75%, LL 25% | 890 |
| Ethanol 50%, LL 25%, DGME 25% | 840 |
| DMSO 99% Gel | 5850 |
| Petrolatum 70%, PG 15%, PS 15% | 2080 |
| Petrolatum 87.5%, PG 7.5%, PS 5% | 1130 |

DGME = diethylene glycol monomethyl ether,
DMSO = dimethylsulfoxide,
LL = lauryl lactate,
PG = propylene glycol,
PS = polysorbate 80

Thus, a formulation of latanoprost comprising propylene glycol and oleic acid provided superior dermal drug penetration compared to a range of other formulations and known enhancers, including DMSO, LL, and DGME. The superiority of the propylene glycol/oleic acid formulation over 99% DMSO was particularly surprising, because DMSO is considered a "universal solvent" with powerful skin penetration enhancement and delivery accelerant properties (see, e.g., Patel et al., Penetration enhancers for transdermal drug delivery system: a review, IJPI J Pharmaceut Cosmetol; 2011; 5:53-65).

Example 5

Skin permeation studies were conducted with various formulations of latanoprost 0.5%, ex vivo, on fresh human skin, as described in the foregoing example. All formulations comprised ethanol (70%) and oleic acid (1.5%, 3% or 4.5%) with the remainder essentially as propylene glycol (28.5%, 27% or 25.5%, respectively). All studies were run in duplicate. Mean 24-hour flux results were as follows:

TABLE 3

| Oleic acid content | Latanoprost Flux ($ng/cm^2/hr$) | Latanoprost Free Acid Flux ($ng/cm^2/hr$) |
|---|---|---|
| 1.5% | 5.5 | 37.7 |
| 3% | 7.4 | 60.1 |
| 4.5% | 5.4 | 55.5 |

Thus, a formulation of latanoprost comprising 3% oleic acid provided superior dermal drug penetration compared to comparable formulations comprising either 1.5% or 4.5% oleic acid. Furthermore, latanoprost (prodrug) was converted (hydrolyzed) to the active metabolite, latanoprost free acid, in the skin samples, a finding which was verified by recovery of latanoprost free acid (at large excess to latanoprost) in the dermis and receptor fluid of each sample.

Example 6

Skin permeation studies were conducted with two formulations of latanoprost 0.1% w/w, ex vivo, on fresh pig skin, by methods essentially as described in the foregoing example. All studies were run in duplicate. Mean 12-hour flux results were as follows:

TABLE 4

| Formulation | Latanoprost Flux ($ng/cm^2/hr$) | Latanoprost Free Acid Flux ($ng/cm^2/hr$) |
|---|---|---|
| 99.9% petrolatum | 0 | 9.7 |
| Ethanol 69.9%, PG 27%, oleic acid 3% | 0.24 | 26 |

Thus, a formulation of latanoprost comprising propylene glycol and 3% oleic acid provided superior dermal drug penetration compared to a formulation comprising 99.9% petrolatum.

Example 7

Skin permeation studies were conducted on compositions comprising latanoprost 0.5% in a vehicle consisting essentially of: (A) 70% ethanol, 27% PG, and 3% oleic acid; (B) 60% ethanol, 10% water, 27% PG, and 3% oleic acid; or (C) 45% ethanol, 25% water, 27% PG, and 3% oleic acid. The three vehicles were associated with similar penetration of latanoprost and latanoprost free acid.

Example 8

Skin permeation studies were conducted on compositions comprising latanoprost 0.3% in a vehicles consisting essentially of: (D) 68% ethanol, 27% PG, 3% oleic acid and 2% hydroxypropylcellulose; (E) 58% ethanol, 27% PG, 10% glycerin, 3% oleic acid and 2% hydroxypropylcellulose; (F) and 68% ethanol, 18% PG, 10% glycerin, 2% oleic acid and 2% hydroxypropylcellulose. The three vehicles were associated with similar penetration of latanoprost and latanoprost free acid.

Example 9

Formulations consisting of varying concentrations of latanoprost, PG 27%, oleic acid 3%, hydroxypropylcellulose 1%, and ethanol q.s. (all w/w) were administered to the dorsal skin (400 $cm^2$) of four Gottingen minipigs. On day 1, animals received 8 ml of a formulation comprising latanoprost 0.02% (w/w). On day 3, they received 8 ml of a formulation comprising latanoprost 0.1% (w/w). On day 5, they received 8 ml of a formulation comprising latanoprost 0.5%. Throughout the study and until day 7, animals were observed for skin condition and overall health and behavior. The formulations were well tolerated on the skin, and no adverse reactions were observed.

Example 10

In two studies, Gottingen minipigs were treated with repeat doses of latanoprost 0.1% or 0.5% in a formulation comprising 27% PG, oleic acid 3%, and HPC 1% with the remainder as ethanol (Study 1; n=3 per group); or latanoprost 0.16% or 0.8% in pluronic lecithin organogel (Study 2; n=6 per group). All animals were treated the same application rate over 10% of body surface area on the dorsal skin. Animals were monitored for skin condition, body weight, and safety. Twenty-four hours after the last dose, animals were scarified, and drug (latanoprost plus LFA) concentrations were measured in local subcutaneous fat by careful dissection of tissue, washing, homogenization, extraction, and liquid chromatography/tandem mass spectrometry (LC/MS/MS). As shown in the table below, 0.1% latanoprost in a PG/oleic acid formulation achieved drug concentration in subcutaneous fat similar to those achieved by 0.8% latanoprost in pluronic lecithin organogel. Furthermore, 0.5% latanoprost in a PG/oleic acid formulation achieved drug concentrations about 15 times higher that 0.8% latanoprost in pluronic lecithin organogel. Furthermore, the PG/oleic acid formulations achieved these results after only 10 doses, whereas the pluronic lecithin organogel results were after 42 doses. Thus, it was concluded that the formulations comprising oleic acid provided PFPRA drug delivery that was about one order of magnitude greater than pluronic lecithin organogel.

TABLE 5

| Formulation | Duration | Total drug in fat (ug/g) |
|---|---|---|
| 0.10% latanoprost 27% PG, 3% OA, 1% HPC, 68.9% ethanol | 10 days | 4 |
| 0.50% latanoprost, 27% PG, 3% OA, 1% HPC, 68.5% ethanol | 10 days | 59 |
| 0.16% latanoprost, pluronic lecithin organogel | 42 days | 1 |
| 0.80% latanoprost, pluronic lecithin organogel | 42 days | 4 |

HPC = hydroxypropylcellulose;
OA = oleic acid;
PG = propylene glycol

Example 11

Three formulations comprising ethanol, propylene glycol, and oleic acid (without active ingredients) were applied to skin on the volar forearms on healthy adult men and women (n=4). The application area was 5 cm×5 cm. Application was once daily for 7 consecutive days. Skin condition and participant experience were noted daily, with results as follows:

TABLE 6

| Formulation (all included 70% ethanol plus 1% Hydroxypropylcellulose) | Skin Condition | Participant Experience |
|---|---|---|
| PG 25.5%, oleic acid 4.5% | Normal (100%) | Well-tolerated, aesthetically pleasing |
| PG 27%, oleic acid 3% | Normal (100%) | Well-tolerated, aesthetically pleasing |
| PG 28.5%, oleic acid 1.5% | Normal (100%) | Well-tolerated, aesthetically pleasing |

PG = propylene glycol,
PS = polysorbate 80

Thus, the above formulations comprising propylene glycol and oleic acid were non-irritating when applied repeatedly to human skin.

Example 11

A composition consisting essentially of latanoprost 0.5%, ethanol 67%, propylene glycol 27%, oleic acid 3% (all w/w) was administered to the dorsal skin (10% of body surface area) of eight Gottingen minipigs, once daily for 13 weeks. An equal number of animals were treated with a placebo composition, consisting essentially of ethanol 67%, propylene glycol 27%, oleic acid 3% (all w/w). Animals were observed for safety and tolerability. The compositions were well tolerated in all animals. After 13 weeks, animals were sacrificed and dorsal skin, fat, and muscle were dissected en bloc from a standardized portion of the treatment area. As compared to animals treated with the placebo composition, there was gross atrophy, i.e., a thickness reduction of 30% to 70%, of subcutaneous fat in animals treated with the latanoprost 0.5% article.

Example 12

From the study described in Example 11, a portion of the tissue is fixed in formalin, stained with hematoxylin and eosin, and examined histopathologically. Subcutaneous fat thickness is measured systematically, for example by measuring the thickness of fat from the dermis to the panniculus carnosus using image analysis software such as ImageJ (National Institutes of Health). From another portion of the tissue, subcutaneous fat is dissected, washed, pulverized, and homogenized, with the homogenate submitted for quantification of latanoprost free acid concentration using liquid chromatography with tandem mass spectrometry (a method known in the art). It is predicted that the composition containing latanoprost will be associated with reduced subcutaneous fat thickness, as compared to control. It is further predicted that the latanoprost composition will be associated with amounts of latanoprost free acid in subcutaneous fat that are considered therapeutically effective, with reference to other in vivo experiments and in vitro assays. It is further predicted that the latanoprost composition of this example will be associated with higher tissue concentrations of latanoprost free acid and/or higher degrees of subcutaneous fat reduction compared to other formulations hitherto disclosed.

Example 13

A composition comprising 27% PG, 3% oleic acid, 2% hydroxypropylcellulose, and ethanol, and optionally comprising latanoprost, was tested in a clinical trial. Patients (n=18) applied the compositions to a 50 $cm^2$ area of skin once daily for 42 consecutive days. Patients underwent serial skin exams and local and systemic safety assessments. The compositions were well tolerated, and skin exams were unremarkable. No systemic side effects were noted.

Example 14

Different compositions, comprising latanoprost 5 mM, are tested on obese mice. Mice approximately six weeks old, all with similar baseline body mass, are randomized and prospectively treated as follows (n=5 animals per group):

TABLE 7

| Group | Compound | Formulation (w/w) |
|---|---|---|
| A | Vehicle only | Ethanol 70%, PG30% |
| B | Vehicle only | Ethanol 70%, PG 27%, oleic acid 3% |
| C | Latanoprost 5 mM | Ethanol about 69.8%, PG 30% |
| D | Latanoprost 5 mM | Ethanol about 69.8%, PG 27%, oleic acid 3% |

The dose is 0.1 cc to the right flank, daily. Mice are fed ad libitum and weighed daily for about 28 days. On or about day 28, mice are sacrificed and samples of skin with subcutaneous fat are collected for histologic examination.

It is predicted that after about 28 days, mice in Group D will show relatively less weight gain (or more weight loss) and relatively less adiposity compared to mice in any of Groups A, B, or C.

Thus, it is predicted that in a mouse model of obesity, the foregoing results show superior reduction of adiposity with a latanoprost formulation comprising ethanol, propylene glycol, and oleic acid, as compared to a comparable equimolar latanoprost formulation that is lacking oleic acid.

Example 15

The following experiment describes a randomized, placebo-controlled, double-blind trial in human subjects to test whether the safety and efficacy of a PFPRA pharmaceutical composition for reduction of submental fat. The composition can be, for example, as described in Example 1, wherein the PFPRA is latanoprost. Alternatively, the PFPRA can be tafluprost. Other alternatives within the scope of the invention can also be used.

Eligible subjects (for example, n=60) with excess submental fat are entered into a randomized double-blind study. Subjects are randomized in 1:1 fashion to receive either the active pharmaceutical composition (for example, comprising latanoprost 0.1% to 0.5% or tafluprost 0.01% to 0.1%, weight per total weight of the composition), or the corresponding inactive vehicle. Subjects are instructed to apply, once a day, a metered dose of 0.5 ml to the chin. Serial clinical assessments, photographs, and magnetic resonance imaging (MRI) scans are performed prior to the first dose and then at 6 and 12 weeks. Treatment continues for a total of 12 weeks. It is contemplated that over time, for example after 12 weeks of treatment, the pharmaceutical composition comprising latanoprost (or tafluprost) will be associated with more reduction in the depth and/or volume of submental fat, as measured by clinical assessment and/or MRI, as compared to vehicle alone.

Example 16

The following experiment describes a randomized, placebo-controlled, double-blind trial in human subjects to test whether the safety and efficacy of a PFPRA pharmaceutical composition for reduction of abdominal fat. The composition can be, for example, as described in Example 1, wherein the PFPRA is latanoprost. Alternatively, the PFPRA can be tafluprost. Other alternatives within the scope of the invention can also be used.

Eligible subjects (for example, n=60) with excess anterior abdominal fat are entered into a randomized double-blind study. Subjects are randomized in 1:1 fashion to receive either the active pharmaceutical composition (for example, comprising latanoprost 0.1% to 0.5% or tafluprost 0.01% to 0.1%, weight per total weight of the composition), or the corresponding inactive vehicle.

Subjects are instructed to apply, once a day, a metered dose, for example, of 2 ml over a 200 $cm^2$ application area on the anterior abdomen. The application area is standardized, for example, by use of a template that is centered on the umbilicus.

Serial clinical assessments, subjective patient assessments, photographs, and magnetic resonance imaging (MRI) scans are performed prior to the first dose and then, for example, at 6 and 12 weeks. Treatment continues, for example, for a total of 12 weeks.

It is contemplated that over time, for example after 6 to 12 weeks of treatment, the pharmaceutical composition comprising latanoprost (or tafluprost) will be associated with more reduction in the depth and/or volume of subcutaneous fat under the treatment area, as measured by clinical assessment, subjective patient assessment, photographs, and/or MRI, as compared to vehicle alone. It is further contemplated that subjects treated with latanoprost or tafluprost will be more satisfied with their cosmetic appearance, compared to those treated with vehicle alone.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for reducing subcutaneous fat in a subject, the method comprising topically administering to the subject a composition comprising a compound of Formula (I):

(I)

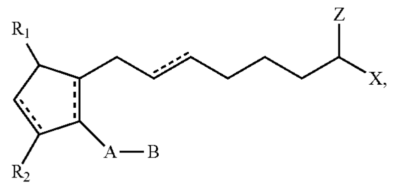

or a pharmaceutically acceptable salt thereof, wherein:

each instance of ------ independently represents a single bond or a double bond which can be in the cis or trans configuration;

A is optionally substituted $C_{1-10}$ alkylene, optionally substituted $C_{2-10}$ alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$ carbocyclyl, optionally substituted 3-8-membered heterocyclyl, optionally substituted 5-14 membered-heteroaryl, optionally substituted $C_{6-10}$ aryl, optionally substituted $C_{1-30}$ alkyl, optionally substituted $C_{2-30}$ alkenyl, or optionally substituted $C_{2-30}$ alkynyl;

X is $—OR_4$, $—SR_4$, or $—N(R_4)_2$, wherein each instance of $R_4$ is independently hydrogen, optionally substituted $C_{1-30}$ alkyl, optionally substituted $C_{2-30}$ alkenyl, optionally substituted $C_{2-30}$ alkynyl, —C(=O)$R_5$, or —C(=O)O$R_5$, wherein $R_5$ is optionally substituted $C_{1-30}$ alkyl, optionally substituted $C_{2-30}$ alkenyl, or optionally substituted $C_{2-30}$ alkynyl, or two $R_4$ groups are joined to form an optionally substituted 3-8-membered heterocyclyl or optionally substituted 5-14-membered heteroaryl ring;

Z is =O, =S, or =N$R_Z$, wherein $R_Z$ is selected from hydrogen, an amino protecting group, —OH, substituted hydroxyl, optionally substituted $C_{1-10}$ alkyl, optionally substituted $C_{2-10}$ alkenyl, optionally substituted $C_{2-10}$ alkynyl, optionally substituted $C_{3-7}$ carbocyclyl, optionally substituted 3-8-membered heterocyclyl, optionally substituted $C_{6-10}$ aryl, or optionally substituted 5-14-membered heteroaryl, or Z represents two hydrogen atoms; and one of $R_1$ and $R_2$ is =O, —OH, or a —O(CO)$R_6$ group and the other one is —OH or —O(CO)$R_6$, or $R_1$ is =O and $R_2$ is H, wherein $R_6$ is an optionally substituted $C_{1-20}$ alkyl, optionally substituted $C_{2-20}$ alkenyl, optionally substituted $C_{2-20}$ alkynyl, or —$(CH_2)_mR_7$, wherein m is 0 or an integer of between 1-10, inclusive, and $R_7$ is optionally substituted $C_{3-7}$ carbocyclyl, optionally substituted 3-8-membered heterocyclyl, optionally substituted $C_{6-10}$ aryl, or optionally substituted 5-14-membered heteroaryl; and wherein the composition further comprises a fatty acid.

2. The method of claim 1, wherein the compound of Formula (I) is of Formula (I-a):

(I-a)

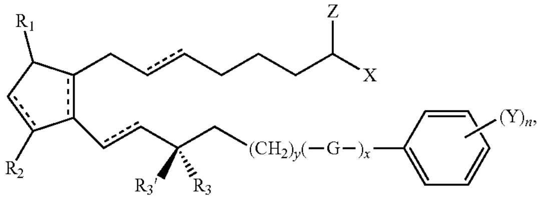

or a pharmaceutically acceptable salt thereof, wherein:

each instance of ------ independently represents a single bond or a double bond which can be in the cis or trans configuration;

each instance of $R_3$ and $R_3$' is independently hydrogen, halogen, —OH, substituted hydroxyl, or —O(CO)$R_8$, wherein $R_8$ is optionally substituted $C_{1-20}$ alkyl, optionally substituted $C_{2-20}$ alkenyl, optionally substituted $C_{2-20}$ alkynyl, or —$(CH_2)_mR_9$ wherein m is 0 or an integer between 1-10, inclusive, and $R_9$ is optionally substituted $C_{3-7}$ carbocyclyl, optionally substituted $C_{6-10}$ aryl, or optionally substituted 5-14-membered heteroaryl, or $R_3$ and $R_3$' are joined to form =O;

Y is selected from the group consisting of optionally substituted $C_{1-10}$ alkyl, $C_{1-10}$ perhaloalkyl, optionally substituted $C_{2-10}$ alkenyl, optionally substituted $C_{2-10}$ alkynyl, halo, nitro, cyano, thiol, substituted thiol, hydroxyl, substituted hydroxyl, amino, monosubstituted amino, and disubstituted amino;

G is —O— or —S—;

y is 0, 1, or 2;

x is 0 or 1; and n is 0 or an integer of from 1 to 5, inclusive.

3. The method of claim 2, wherein the compound of Formula (I-a) is of Formula (I-d3):

(I-d3)

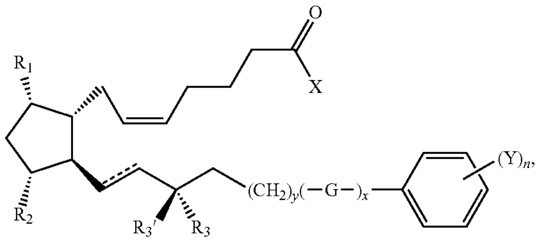

or a pharmaceutically acceptable salt thereof.

4. The method of claim 1, wherein the compound of Formula (I) is selected from the group consisting of bimatoprost, bimatoprost isopropyl ester, bimatoprost free acid, travoprost, fluprostenol, latanoprost, latanoprost free acid, tafluprost, tafluprost free acid, CAY10509, CAY10509 free acid, and pharmaceutically acceptable salts thereof.

5. The method of claim 1, wherein the concentration of the compound of Formula (I) is between about 0.05 percent and about 0.5 percent, inclusive, by weight of the total weight of the composition.

6. The method of claim 1, wherein the fatty acid is of the formula:

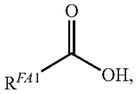

or a pharmaceutically acceptable salt thereof, wherein $R^{FA1}$ is optionally substituted $C_{10-20}$ alkyl or optionally substituted $C_{10-20}$ alkenyl.

7. The method of claim 6, wherein $R^{FA1}$ is an alkenyl group of formula (a):

(a)

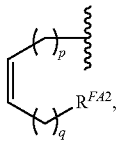

wherein:

p is an integer between 2 and 8, inclusive;

q is an integer between 1 and 8, inclusive; and $R^{FA2}$ is an optionally substituted $C_1$-$C_{10}$ alkyl, or an optionally substituted $C_2$-$C_{10}$ alkenyl;

provided the sum of carbons of formula (a) does not exceed 20.

8. The method of claim 1, wherein the fatty acid is selected from the group consisting of lauric acid, myristic acid, palmitic acid, stearic acid, myristoleic acid, palmitoleic acid, sapienic acid, oleic acid, linoleic acid, and a-linoleic acid.

9. The method of claim 1, wherein the composition comprises between about 1 percent and about 20 percent of fatty acid, inclusive, by weight of the total weight of the composition.

10. The method of claim 1, wherein the composition comprises between about 1 percent and about 5 percent of fatty acid, inclusive, by weight of the total weight of the composition.

11. The method of claim 1, wherein the composition comprises between about 2 percent and about 4 percent of fatty acid, inclusive, by weight of the total weight of the composition.

12. The method of claim 1 further comprising an organic alcohol.

13. The method of claim 12, wherein the organic alcohol is selected from the group consisting of methanol, ethanol, propanol, isopropanol, 1,3-butanediol, ethylene glycol, propylene glycol, and mixtures thereof.

14. The method of claim 13, wherein the organic alcohol is ethanol, propylene glycol, or a mixture thereof.

15. The method of claim 12, wherein the composition comprises between about 5 percent and about 50 percent of organic alcohol, inclusive, by weight of the total weight of the composition.

16. The method of claim 12, wherein the composition comprises between about 20 percent and about 30 percent of organic alcohol, inclusive, by weight of the total weight of the composition.

17. The method of claim 12, wherein the composition comprises between about 60 percent and about 80 percent of organic alcohol, inclusive, by weight of the total weight of the composition.

18. The method of claim 1 further comprising a viscosity-enhancing agent.

19. The method of claim 18, wherein the viscosity-enhancing agent is glycerin.

20. The method of claim 1, wherein the compound of Formula (I) is latanoprost.

21. The method of claim 1, wherein the fatty acid is oleic acid.

22. The method of claim 1, wherein the compound of Formula (I) is latanoprost; and the fatty acid is oleic acid.

* * * * *